US012653786B2

(12) United States Patent
Varum et al.

(10) Patent No.: US 12,653,786 B2
(45) Date of Patent: *Jun. 16, 2026

(54) PREPARATION OF SOLID DOSAGE FORMS COMPRISING ANTIBODIES BY SOLUTIONS/SUSPENSION LAYERING

(71) Applicant: Tillotts Pharma AG, Rheinfelden (CH)

(72) Inventors: Felipe Varum, Rheinfelden (CH); Laetitia Von Rochow, Rheinfelden (CH); Carmen Goetz, Rheinfelden (CH); Roberto Bravo, Rheinfelden (CH)

(73) Assignee: Tillotts Pharma AG, Rheinfelden (CH)

( * ) Notice: Subject to any disclaimer, the term of this patent is extended or adjusted under 35 U.S.C. 154(b) by 24 days.

This patent is subject to a terminal disclaimer.

(21) Appl. No.: 18/520,348

(22) Filed: Nov. 27, 2023

(65) Prior Publication Data

US 2024/0099980 A1     Mar. 28, 2024

Related U.S. Application Data

(63) Continuation of application No. 16/647,322, filed as application No. PCT/EP2018/074520 on Sep. 11, 2018, now Pat. No. 11,826,470.

(30) Foreign Application Priority Data

Sep. 20, 2017    (EP) .................................... 17192260

(51) Int. Cl.
| | |
|---|---|
| A61K 9/16 | (2006.01) |
| A61K 9/00 | (2006.01) |
| A61K 39/395 | (2006.01) |
| A61K 47/26 | (2006.01) |
| A61K 47/38 | (2006.01) |
| C07K 16/24 | (2006.01) |

(52) U.S. Cl.
CPC .......... *A61K 9/1676* (2013.01); *A61K 9/0053* (2013.01); *A61K 9/1682* (2013.01); *A61K 39/3955* (2013.01); *A61K 47/26* (2013.01); *A61K 47/38* (2013.01); *C07K 16/241* (2013.01)

(58) Field of Classification Search
None
See application file for complete search history.

(56) References Cited

U.S. PATENT DOCUMENTS

| | | |
|---|---|---|
| 5,780,028 A | 7/1998 | Graham |
| 5,900,252 A | 5/1999 | Calanchi |

| | | | |
|---|---|---|---|
| 11,826,470 B2 * | 11/2023 | Varum ............... | A61K 39/3955 |
| 2007/0026082 A1 | 2/2007 | Lizio et al. | |
| 2008/0152719 A1 | 6/2008 | Petereit | |
| 2008/0220080 A1 | 9/2008 | Petereit | |
| 2010/0239682 A1 | 9/2010 | Andremont | |
| 2011/0268808 A1 | 11/2011 | Jain et al. | |
| 2017/0121402 A1 | 5/2017 | Chtourou | |
| 2021/0030682 A1 | 2/2021 | Varum | |

FOREIGN PATENT DOCUMENTS

| | | |
|---|---|---|
| EP | 2 143 424 | 1/2010 |
| EP | 2 777 695 A1 | 9/2014 |
| JP | H05-506217 A | 9/1991 |
| JP | H07-69927 A | 3/1995 |
| JP | 2002-506018 | 2/2002 |
| JP | 2008-534530 | 8/2008 |
| WO | WO 1991/01602 | 10/1991 |
| WO | WO 1991/016042 | 10/1991 |
| WO | WO 1993/00077 | 1/1993 |
| WO | WO 1999/45903 A1 | 9/1999 |
| WO | WO 2009/076754 A1 | 6/2009 |
| WO | WO 2009/083607 A1 | 7/2009 |
| WO | WO 2008/117814 A | 7/2010 |
| WO | WO 2012/130872 A1 | 10/2012 |
| WO | WO 2014/143085 A1 | 9/2014 |
| WO | WO 2015/138200 A1 | 9/2015 |

OTHER PUBLICATIONS

Elsevier, "How to Conduct a Review", www.elsevier.com/reviewer/howtoreview (Jan. 2, 2024).
Andrew Bristol et al., "Formulation Development of SYN-004 (ribaxamase) Oral Solid Dosage Form, a ß-lactamase, to Prevent Intravenous Antibiotic-Associated Dysbiosis of the Colon", Int. J. Pharm., (Oct. 2017), vol. 534: pp. 25-34.
Morflex, Inc., "Influence of Triethyl Citrate on the Properties of Tablets Containing Coated Pellets", *Pharmaceutical Coatings Bulletin*, 102-4, 1996.
Evonik Industries AF, Technical Information Sheet for "EUDRAGIT® L 30 D-55", Darmstadt, Germany, May 2014.
Wikipedia, "Modified-Release Dosage", https://en.wikipedia.org/w/index.php?title-Modified-release_dosage&oldid=807013582 (retrieved Jul. 14, 2023).
Evonik Industries, "Eudragit: Setting benchmarks in solid oral dosage forms since 1954", Darmstadt, Germany (2010).
Evonik Industries, "Eudragit: Acrylic Polymers for Solid Oral Dosage Forms", Darmstadt, Germany (2012).

* cited by examiner

*Primary Examiner* — Aradhana Sasan
(74) *Attorney, Agent, or Firm* — Smith Patent, LLC; Chalin A. Smith

(57)     ABSTRACT

The present invention relates to a method for preparing immediate and sustained release solid dosage forms, comprising antibodies and functional fragments thereof, by solution/suspension layering, optionally coated with a delayed release coating; the solid dosage forms prepared by the method; and the use of the solid dosage forms in the topical treatment in the gastrointestinal tract of a patient.

24 Claims, 13 Drawing Sheets

| Formulation | ADA conc. susp (mg/mL) | Anti-tacking (%) | Reached loading (%) | Drying |
|---|---|---|---|---|
| Example 14 | 50 | 10% Syloid® 244 FP | 0.86 | 24h/40°C |
| Example 15 | 25 | 10% Syloid® 244 FP | 1.40 | 24h/40°C |
| Example 16 | 25 | 10% GMS | 1.53 | 24h/40°C |
| Example 17 | 25 | 20% Syloid® 244 FP | 1.24 | 24h/40°C |

| Batch | Core | Reached polymer weight gain (%) | Final adalimumab loading (%) |
|---|---|---|---|
| Comparative Example 1 | Suglets | n.a | 2.196 |
| Example 6 | Comparative example 1 | 6.89 | 2.02 |
| Example 7 | Comparative Example 1 | 14.63 | 1.85 |
| Example 8 | Comparative Example 1 | 23.14 | 1.80 |

| Batch | Plasticizer[1) | Coalescence enhancer (Lauroglycol™ 90) (%) | Curing conditions | Reached polymer weight gain (%) | Final adalimumab loading (%) |
|---|---|---|---|---|---|
| Example 9 | 25% TEC | 0 | 2h/60°C oven | 16.32 | 1.94 |
| | | | 24h/60°C oven | 17.12 | 1.93 |
| Example 10 | 25% DBS | 0 | 2h/60°C oven | 17.71 | 1.83 |
| | | | 24h/60°C oven | 16.95 | 1.84 |
| Example 11 | 25% DBS | 10 | 1h/60°C oven | 11.73 | 1.68 |
| | | | 2.5h/60°C oven | 11.38 | 1.69 |
| | | | 24h/60°C oven | 11.56 | 1.68 |

| Batch | Lauroglycol™ 90 (%), based on polymer | Reached polymer weight gain (%) | Final adalimumab loading (%) |
|---|---|---|---|
| Example 6 | 0 | 6.89 | 1.61 |
| Example 12 | 5 | 5.35 | 1.81 |

- ········· Example 6 24h curing
- ─※─ Example 12 1h curing
- ─▲─ Example 12 2h curing
- ─●─ Example 12 24h curing

PREPARATION OF SOLID DOSAGE FORMS COMPRISING ANTIBODIES BY SOLUTIONS/SUSPENSION LAYERING

PRIORITY

This application is a continuation of U.S. application Ser. No. 16/647,322 filed Mar. 13, 2020 (now U.S. Pat. No. 11,826,470), which, in turn, corresponds to the U.S. National phase of International Application No. PCT/EP2018/074520, filed Sep. 11, 2018, which, in turn, claims priority to European Patent Application No. 17.192260.2 filed Sep. 20, 2017, the contents of which are incorporated by reference herein in their entirety.

FIELD OF THE INVENTION

The present invention relates to a method for preparing immediate and sustained release solid dosage forms, comprising antibodies and functional fragments thereof, by solution/suspension layering, optionally coated with a delayed release coating; the solid dosage forms prepared by the method; and the use of the solid dosage forms in the topical treatment in the gastrointestinal tract of a patient.

BACKGROUND OF THE PRESENT INVENTION

Different pharmaceutical compositions prepared by various methods have been proposed and in some cases implemented comprising biologically active polypeptides like enzymes or hormones. Such biologically active polypeptides, in particular large polypeptides with antigen binding activity such as antibodies and functional fragments thereof, due to their intrinsic nature, are sensitive to any change in their environment, giving rise to inherent instability. Therefore, ensuring their stability and activity as well as the therapeutically efficacious release upon incorporation into a pharmaceutical composition is very challenging and yet paramount due to the prohibitive costs of such antibodies in quantities that allow their therapeutic application to a patient. Generally, this inherent instability of antibodies is independent of whether they are used to prepare a pharmaceutical composition in a liquid, gelatinous, semi-solid, solid or any other form. However, in particular for solid dosage forms, many processing steps in the preparation can be detrimental to stability and activity of an antibody or functional fragment thereof.

The use of solid dosage forms is very common for pharmaceutical compositions intended for enteral administration. Enteral administration, and especially oral administration, of solid dosage forms comprising biologically active polypeptides has become increasingly important in recent years, as it allows, besides a systemic treatment, for the topical treatment of symptoms of diseases of the gastrointestinal tract, as for example inflammatory bowel disease (IBD), colorectal cancer, diarrhea or microbial infections.

Many factors may affect the chemical and physical stability and thereby the activity of large biologically active polypeptides like antibodies and functional fragments thereof during the incorporation into a solid dosage form. Chemical instability of large polypeptides, e.g. in the form of fragmentation, oxidation, deamination, isomerization, disulfide bond formation or formation of acidic/basic species, is directly affected by excipients used in the solid dosage form, as well as by pH, physical stress and temperature during the preparation and later storage of the solid dosage form. Physical instability, e.g. in the form of denaturation, aggregation or adsorption, can result from shear stress, changes in temperature, or high pressure during preparation and later storage. For example already a moderately elevated temperature of greater than 55° C. has been shown to cause some denaturation of immunoglobulin G (IgG) thereby affecting the integrity of the polypeptide, with the antigen binding fragment (Fab) being part of the polypeptide most sensitive to the elevated temperature (Vermeer et al., Biophys J., 2000 January, 78(1): 394-404). Biological instability, e.g. in the form of proteolytic digestion or post-translational modification, can result from the exposure to proteases and other enzymes, as well as other biological factors able to affect the integrity of large polypeptides. The processing of large biologically active polypeptides, such as antibodies and functional fragments thereof, in order to incorporate them into solid dosage forms, therefore poses major challenges, in particular with regard to the choice of individual excipients as well as with regard to the processing parameters. In addition to directly affecting stability and activity of the large biologically active polypeptide, the choice of method for preparing the solid dosage form will also affect the properties of the resulting solid dosage form, i.e. its stability, integrity, quality and dissolution behavior.

Solid dosage forms can be prepared by drug layering. For example drug layering using powder layering can be used to apply a coating comprising an active agent to a core. Drug layering using powder layering involves layering a core with a powder, e.g. comprising an active agent, for example in a pan coater, using a binding liquid. Methods for drug layering using powder layering are known in the art and are disclosed for example in U.S. Pat. Nos. 9,107,804, 6,354,728 or WO 2005/115340. The powder layering process, however, is time consuming requiring many repetitions. Powder layering has other disadvantages including occurrence of the agglomerations of the cores, uneven surface of the resulting layered cores and low loading of the active agent. Furthermore, powder layering requires that the protein (antibody is previously spray-dried or lyophilized, which adds further manufacturing steps.

Drug layering using solution/suspension layering (or coating) on the other hand involves depositing a substance dissolved or dispersed in a solvent on the surface of a substrate. One way of depositing a substance on a substrate is using spray coating, for example by air-suspension coating or fluidized-bed spray coating. In fluidized-bed spray coating one or more substances are dissolved or dispersed in a liquid carrier in the form of a solvent. This solution or dispersion is then sprayed onto a substrate, e.g. an inert core (sucrose or microcrystalline cellulose spheres, etc.) suspended in a fluidized bed of a fluidized-bed spray coater. Fluidized-bed spray coating is known in the art for use in applying a functional coating to a core unit, the core unit optionally comprising an active agent. A functional coating in this context may refer to a seal coating, for example to protect the core from mechanical and chemical stress, or a modified release coating, for example to modify the timing or rate of release of an active agent contained in the core (e.g. a sustained release coating or a delayed release coating). Such methods for applying a functional coating by fluidized-bed spray coating are disclosed for example in WO 2004/062577, EP 1 684 729, WO 2005/046561 or WO2005/115340.

Drug layering using solution/suspension layering allows the preparation of solid dosage forms with uniform size distribution and smooth surface morphology. Compared to other methods for preparing solid dosage forms, like powder layering, drug layering using spray coating thereby has the potential to ensure consistent and reproducible drug dissolution, which is particularly desirable for sustained release solid dosage forms. Methods for drug layering using solution/suspension layering of an active agent in the form of smaller molecules with low sensitivity to physical and chemical stresses are known in the art and include for example those disclosed in EP 1 643 977, WO 2004/062577, EP 1 037 968 or EP 1 643977 and commercial products like Sporanox® or Entocort®.

These methods of drug layering using solution/suspension layering known in the art tend to be unsuitable for the use with antibodies and functional fragments thereof. In particular processing parameters including inlet air temperature, agitation, flow rate, atomizing pressure and drying temperature may affect stability and activity of the antibody or functional fragment thereof used. Moreover, the antibody or functional fragment thereof can be incompatible with certain excipients used. Finally the mass ratio of active agent to excipients used in the coating solutions in these methods may be very low, and thus not allowing a sufficient amount of a large biologically active polypeptide, like an antibody and functional fragment thereof, to be deposited on a substrate for oral or rectal administration of a therapeutically effective dose of the antibody and functional fragment thereof to a human patient using a solid dosage form. Importantly, in particular for antibodies and functional fragments thereof a high concentration in solution or suspension is often detrimental for stability and activity of the antibody and functional fragment thereof.

In IBD, like ulcerative colitis or Crohn's disease, for the inflamed colonic mucosa to be exposed to an antibody concentration effective for topical treatment, the antibody must retain sufficient stability and activity until it is taken up by the target mucosa. In order to minimize antibody degradation in the colonic luminal fluids (Yadav et al., International Journal of Pharmaceutics, 2016. 502(1-2): p. 181-187), a slow and controlled release of antibodies or functional fragments thereof from a solid dosage form is desirable. This would ensure the release of the antibody or functional fragment thereof from the solid dosage form at a rate that allows the effective uptake into mucosa and a continuous provision of antibody or functional fragment thereof over several hours and up to a day. Moreover, it would allow the treatment of a greater target area of inflamed mucosa, as it would allow the solid dosage form to release antibodies or functional fragments thereof while moving along the inside of the gastrointestinal tract. However, the recovery of antibodies or functional fragments from solid dosage forms may be further diminished by the use of polymers suitable for a prolonged release of the antibody or functional fragment thereof (i.e. sustained release polymeric binders).

Gastrointestinal transit, in particular, colonic transit of solid dosage forms shows a wide inter- and intra-individual variability (Varum et al., Int. J. Pharm., 2010. 395(1-2): p. 26-36). Furthermore, IBD such as ulcerative colitis or Crohn's disease can also influence transit time. It has been shown that in some cases colonic transit is prolonged in ulcerative colitis, in the areas proximal to the inflamed mucosa. Thus a dosage form will stay in those areas longer, before reaching the inflamed mucosa. If the antibody is not provided in a stable enough form this could mean premature antibody degradation leading to reduced levels of antibody reaching the distal colonic mucosa. On the other hand, transit through the inflamed area can be accelerated in some cases, which further complicates the design of a dosage form for an efficient antibody delivery to the ileum and large intestine.

Due to the biopharmaceutical advantages of multiparticulates over single units, such as longer colonic transit than single units and wider spread of dose in multiple small units (Varum et al., Int. J. Pharm., 2010. 395(1-2): p. 26-36), a multiparticulate drug delivery system would be a preferred choice. Single units of such a multiparticulate drug delivery system could be designed to achieve sustained antibody release.

Thus, there is a need for a method for preparing a solid dosage form by drug layering comprising antibodies or functional fragments thereof that minimizes loss of biological activity of the antibody or functional fragment thereof used for the preparation of the solid dosage form. In particular, the method should minimize processing time of the solid dosage form, preserve stability and activity of the antibody or functional fragment thereof during individual steps of the preparation, allow release over a short or a prolonged period of time, and reduce interactions of the antibody or functional fragment thereof with other ingredients of the solid dosage form that limits antibody recovery.

SUMMARY OF THE PRESENT INVENTION

After testing various processing conditions and excipients the present inventors found an advantageous method for preparing a solid dosage form comprising at least one antibody or functional fragment thereof by drug layering. This method ensures a fast and straight forward preparation of the solid dosage form, preserves stability and activity of the antibodies or functional fragments thereof used for the preparation and ensures that an optimal amount of the antibody or functional fragment thereof can be recovered from the solid dosage form upon dissolution in a controlled manner. Moreover, the method allows for the preparation of a sustained release solid dosage form that ensures a sustained and controlled release from the solid dosage form over a defined period of time, e.g. over the course of a day; for the preparation of a delayed release oral dosage form that prevents release before a target site in the gastrointestinal tract of a patient.

Thus, the present invention provides a novel method for preparing a solid dosage form, comprising as an active agent at least one antibody or functional fragment thereof, prepared by drug layering. The present invention relates to the subject matter defined in the following items 1 to 161:

[1] A method for preparing a solid dosage form comprising i) an inert core unit; and ii) a drug coating comprising at least one antibody or functional fragment thereof as active agent, a buffer and at least one polymeric binder, deposited on the inert core unit by drug layering; the method comprising the steps of
a) preparing an active agent coating liquid, comprising the at least one antibody or functional fragment thereof, the buffer and the at least one polymeric binder as an aqueous solution or suspension;
b) layering the inert core unit with the active agent coating liquid using spray coating, preferably fluidized-bed spray coating; and
c) drying the wet drug layered inert core unit, simultaneously with step b), or after step b) has been completed, to give rise to a dried solid dosage form.
[2] Method according to item 1, wherein during step a) the at least one antibody or functional fragment thereof in the form of a powder is added to an aqueous solution or suspension, before or after the at least one polymeric binder is added.

[3] Method according to item 1 or 2, wherein the at least one antibody or functional fragment thereof is dissolved in the active agent coating liquid of step a).

[4] Method according to any of items 1 to 3, wherein the active agent coating liquid is an aqueous suspension where 100% of the solvent used is water.

[5] Method according to any of the above items, wherein during step b) fluidized-bed spray coating or pan spray coating is used, preferably fluidized-bed spray coating.

[6] Method according to any of the above items, wherein the active agent coating liquid is sprayed onto the inert core unit using a top-spray or bottom-spray fluidized-bed spray coater.

[7] Method according to any of the above items, wherein the active agent coating liquid comprises 0.01-100 mg/ml, preferably 0.1-50 mg/ml, more preferably 0.5-50 mg/ml, even more preferably 1-50 mg/ml, even more preferably 1-30 mg/ml, even more preferably 1-25 mg/ml, even more preferably 5-25 mg/ml, most preferably about 25 mg/ml, alternatively most preferably about 15 mg/ml, of the at least one antibody or functional fragment thereof.

[8] Method according to any of the above items, wherein the active agent coating liquid comprises 5-300 wt.-%, preferably 20-200 wt.-%, more preferably 50-150 wt.-%, even more preferably 50-115 wt.-%, even more preferably 85-115 wt.-%, most preferably about 90-105 wt.-%, alternatively most preferably about 45-60 wt.-%, of the at least one antibody or functional fragment thereof, relative to the total weight of the polymeric binder solids in the active agent coating liquid.

[9] Method according to any of the above items, wherein the active agent coating liquid comprises:
   i) 0.001-10 wt.-%, preferably 0.01-7 wt.-%, more preferably 0.05-5 wt.-%, even more preferably 0.1-3.5 wt.-%, even more preferably 0.5-2.5 wt.-%, most preferably about 1.4 wt.-%, alternatively most preferably about 4.7 wt.-%, of the at least one antibody or functional fragment thereof;
   ii) 0.1-20 wt.-%, preferably 0.5-10 wt.-%, more preferably 1-5 wt.-%, even more preferably 1-3 wt.-%, even more preferably 2-3 wt.-%, most preferably about 2.5 wt.-%, polymeric binder, alternatively most preferably about 7-7.5 wt.-%, polymeric binder; and
   iii) 0-5 wt.-%, preferably 0.01-3 wt.-%, more preferably 0.1-2 wt.-%, even more preferably 0.1-1 wt.-%, even more preferably 0.2-0.6 wt.-%, most preferably about 0.25 wt.-%, anti-tacking agent.

[10] Method according to item 9, wherein the active agent coating liquid comprises:
   i) 0.5-5 wt.-% antibody or functional fragment thereof;
   ii) 1-5 wt.-% polymeric binder; and
   iii) 0-1.25 wt.-% anti-tacking agent.

[11] Method according to item 9, wherein the active agent coating liquid comprises:
   i) 0.5-2.5 wt.-% antibody or functional fragment thereof;
   ii) 1-3 wt.-% polymeric binder; and
   iii) 0.2-0.6 wt.-% anti-tacking agent.

[12] Method according to item 9, wherein the active agent coating liquid comprises:
   i) about 2.5 wt.-% antibody or functional fragment thereof;

ii) about 2.5 wt.-% polymeric binder; and
   iii) about 0.25 wt.-% anti-tacking agent.

[13] Method according to item 9, wherein the active agent coating liquid comprises:
   i) about 1.5 wt.-% antibody or functional fragment thereof;
   ii) about 2.5 wt.-% polymeric binder; and
   iii) about 0.25 wt.-% anti-tacking agent.

[14] Method according to item 9, wherein the active agent coating liquid comprises:
   i) 0.01-5 wt.-% antibody or functional fragment thereof;
   ii) 0.5-10 wt.-% polymeric binder; and
   iii) 0.01-5 wt.-% anti-tacking agent.

[15] Method according to item 9, wherein the active agent coating liquid comprises:
   i) 0.5 wt.-% antibody or functional fragment thereof;
   ii) 1-3 wt.-% polymeric binder; and
   iii) 0.2-0.6 wt.-% anti-tacking agent.

[16] Method according to any of the above items, wherein the active agent coating liquid comprises 0.01-20 wt.-%, preferably 0.1-10 wt.-%, more preferably 0.5-5 wt.-%, even more preferably 1-5 wt.-%, most preferably about 4.5 wt.-%, alternatively most preferably about 15 wt.-%, buffer.

[17] Method according to any of the above items, wherein during the spray coating the atomising air pressure at the spray nozzle is lower than 200 kPa, preferably 100 kPa, more preferably from 10 to 100 kPa, even more preferably from 10 to 50 kPa, even more preferably from 25 to 50 kPa, even more preferably about 25 kPa.

[18] Method according to any of the preceding items, wherein a fluidized-bed spray coater is used and wherein in the spray coater the inlet air temperature is lower than 65° C., preferably from 25° C. to 60° C., more preferably from 35° C. to 55° C., even more preferably from 40° C. to 50° C., even more preferably from 42° C. to 50° C.

[19] Method according to any of the preceding items, wherein the active agent coating liquid comprises 0.1-20 wt.-%, preferably 0.5-10 wt.-%, more preferably 0.5-5 wt.-%, even more preferably 1-5 wt.-%, even more preferably 1-3 wt.-%, even more preferably about 2.5 wt.-%, alternatively most preferably about 7-7.5 wt.-%, polymeric binder.

[20] Method according to any of the preceding items, wherein the inert core unit is an inert pellet, mini-tablet, tablet, granule, core, bead, mini sphere or sphere.

[21] Method according to any of the preceding items, wherein the inert core unit comprises a monosaccharide, disaccharide, oligosaccharide, polysaccharide, silica, tartaric acid, calcium carbonate, or a combination thereof as a main component.

[22] Method according to any of the preceding items, wherein the inert core unit is a pellet with a sphericity degree of at least 0.6, preferably at least 0.7, more preferably at least 0.8, even more preferably at least 0.9, even more preferably at least 0.95.

[23] Method according to any of the preceding items, wherein the inert core unit is a pellet with a median particle size of 50-10000 µm, preferably 100-3000 µm, more preferably 350-2000 µm, even more preferably 500-1500 µm, most preferably 700-1200 µm.

[24] Method according to any of the preceding items, wherein the inert core unit is a pellet with a particle size distribution such that at least 85% of the pellets have a particle size of 50-3000 µm, preferably 100-1500 µm, more preferably 350-1400 μm, even more preferably 500-1200 μm, most preferably 700-1200 μm.

[25] Method according to any of the preceding items, wherein the inert core unit is a pellet comprising a sphere consisting of microcrystalline cellulose, sucrose, starch, mannitol, calcium carbonate, silica, tartaric acid, lactose, or a combination thereof.

[26] Method according to any of the preceding items, wherein the inert core unit is a pellet comprising a sphere consisting of microcrystalline cellulose.

[27] Method according to any of the preceding items, wherein the inert core unit is pharmacologically inactive and comprises a monosaccharide, disaccharide, oligosaccharide, polysaccharide, silica, tartaric acid or a combination thereof as a main component.

[28] Method according to any of items 1 to 27, wherein the inert core unit is a pellet in the form of a sphere consisting of microcrystalline cellulose, sucrose, starch mannitol, calcium carbonate, silica, tartaric acid, lactose, or a combination thereof, preferably microcrystalline cellulose.

[29] Method according to any of the preceding items, wherein the inert core unit is pharmaceutically inactive.

[30] Method according to any of items 1 to 26, wherein the inert core unit comprises at least one active agent.

[31] Method according to item 30, wherein the at least one active agent is in the form of at least one antibody or functional fragment thereof.

[32] Method according to item 31, wherein the at least one antibody or functional fragment thereof is the same or different from the at least one antibody in the drug coat.

[33] Method according to any of items 30 to 32, wherein the at least one active agent of the inert core unit is released simultaneously with the at least one antibody in the drug coating, upon immersion of the solid dosage form in an aqueous environment.

[34] Method according to any of items 30 to 32, wherein the release of the at least one active agent of the inert core unit starts later and/or with a faster/slower release rate than the at least one antibody or functional fragment thereof in the drug coating, upon immersion of the solid dosage form in an aqueous environment.

[35] Method according to any of items 20 to 35, wherein the pellet comprises a coating deposited on the sphere (e.g. a seal coating).

[36] Method according to any of the preceding items, wherein the polymeric binder in the drug coating is selected from hydroxypropyl methylcellulose (HPMC); methylcellulose (MC); polyvinylpyrrolidone (PVP); hydroxypropyl cellulose (HPC); macrogol poly (vinylalcohol) grafted copolymer (e.g. Kollidon® IR); and combinations thereof; preferably HPMC or MC; more preferably HPMC.

[37] Method according to any of the preceding items, wherein the polymeric binder in the drug coating is suitable for an immediate release drug coating.

[38] Method according to any of the preceding items, wherein the wet drug layered inert core unit is dried simultaneously with step b), preferably using the inlet air flow of a fluidized bed.

[39] Method according to item 38, wherein the inlet air has a temperature of up to 65° C., preferably up to 60° C., more preferably up to 55° C., more preferably 40 to 50° C., even more preferably about 45° C.

[40] Method according to any of items 1 to 35, wherein the polymeric binder in the drug coating comprises at least one sustained release polymeric binder.

[41] Method according to item 40, wherein the polymeric binder in the drug coating is suitable for a sustained release drug coating.

[42] Method according to item 40 or 41 wherein the at least one sustained release polymeric binder is added to the active agent coating liquid in the form of an aqueous suspension (aqueous dispersion).

[43] Method according to any of items 40 or 42, wherein the wet drug layered inert core unit is dried after step b) has been completed.

[44] Method according to item 43, wherein the drying temperature is not higher than 65° C., preferably not higher than 60° C., more preferably not higher than 55° C., and the drying is carried out preferably in an oven or in a fluidized bed equipment, more preferably a large-scale fluidized bed equipment.

[45] Method according to item 43 or 44, wherein the wet drug layered inert core unit is dried for 30 min to 30 h, preferably about 30 min to 24 h.

[46] Method according to any of items 40 to 45, wherein the at least one sustained release polymeric binder is selected from the group consisting of poly(ethyl acrylate, methyl methacrylate) 2:1 (e.g. Eudragit® NM 30D, Eudragit® NE 30D); poly(ethyl acrylate, methyl methacrylate, trimethylammonioethyl methacrylate chloride) 1:2:0.1 (e.g. Eudragit® RS 30D); poly(ethyl acrylate, methyl methacrylate, trimethylammonioethyl methacrylate chloride) 1:2:0.2 (e.g. Eudragit® RL 30D); ethylcellulose (e.g. Surelease® or Aquacoat® ECD), polyvinyl acetate (e.g. Kollicoat® SR 30D); and combinations thereof.

[47] Method according to any of items 40 to 46, wherein the ratio of the at least one sustained release polymeric binder to the at least one antibody or functional fragment thereof (w/w) modifies the release rate of the at least one antibody or functional fragment thereof, such that a higher ratio results in a slower release rate.

[48] Method according to any of items 40 to 47, wherein the at least one sustained release polymeric binder (S) and the at least one antibody or functional fragment thereof (A) are present in the active agent coating liquid in a ratio S/A (w/w) of 0.5 to 100, preferably 10 to 30, more preferably 15 to 25.

[49] Method according to any of the above items, wherein the active agent coating liquid further comprises an anti-tacking agent.

[50] Method according to item 49, wherein the anti-tacking agent is selected from colloidal silica dioxide, mesoporous silica, glycerolmonostearate (GMS), stearic acid, magnesium stearate and talc, preferably mesoporous silica or GMS, more preferably mesoporous silica.

[51] Method according to item 49 or 50, wherein the active agent coating liquid relative to the total weight of the polymeric binder solids comprises 0.1-50 wt.-%, preferably 1-30 wt.-%, more preferably 10-20 wt.-%, or 5-50 wt.-%, anti-tacking agent.

[52] Method according to any of the above items, wherein the active agent coating liquid further comprises a plasticizer.

[53] Method according to item 52, wherein the plasticizer is selected from the group consisting of triethyl citrate (TEC), polyethylene glycol, acetyl triethyl citrate, butyl citrate, polysorbates, 1,2-polyproppylene glycol and dibutyl sebacate (DBS).

[54] Method according to item 52 or 53, wherein the active agent coating liquid comprises 5-35 wt.-%, preferably 10-30 wt.-%, more preferably about 20-25 wt.-%, plasticizer, relative to the total weight of the polymeric binder solids in the active agent coating liquid.

[55] Method according to any of the above items, wherein the active agent coating liquid comprises a coalescence enhancer.

[56] Method according to item 55, wherein the coalescence enhancer is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, fatty alcohols such as cetyl alcohol or oleyl alcohol, sodium glycolate, sodium de(s)oxycholate, polyethylene glycol, polypropylene glycol, alkyl poly (ethylene oxide), alkyl glycoside, alkyl polyglucoside, octyl glucoside, decyl maltoside, propylene glycol monolaurate (e.g. Lauroglycol 90), and combinations thereof, preferably a polysorbate, such as polysorbate 20, 28, 40, 60, 65, 80, 81 and 85; a poloxamer, such as poloxamer 124, 181, 188, 237, 331, 338 and 407; an alkyl polyglucoside (e.g., octyl glucoside and decyl maltoside); or propylene glycol monolaurate (e.g. Lauroglycol 90); more preferably propylene glycol monolaurate (e.g. Lauroglycol 90).

[57] Method according to item 55 or 56, wherein the active agent coating liquid comprises 1-20 wt.-%, preferably 2-15 wt.-%, more preferably 5-10 wt.-%, coalescence enhancer, relative to the total weight of the sustained release polymeric binder solids in the active agent coating liquid.

[58] Method according to any of the above items, wherein the buffer (buffer salt) is selected from the group consisting of acetate buffer, citrate buffer, histidine buffer, succinate buffer, phosphate buffer, hydroxymethylaminomethane (TRIS) buffer, and combinations thereof, preferably a buffer at a pH compatible with the at least one antibody or functional fragment thereof, alternatively preferably a buffer at a physiological pH.

[59] Method according to any of the above items, wherein the solid dosage form is a pellet, bead, sphere, mini sphere, granule, tablet or mini tablet, preferably a pellet.

[60] Method according to any of the preceding items, wherein the drug coating after step c) has an average thickness of 0.5-300 μm, preferably 0.5-100 μm, more preferably 1-50 μm, even more preferably 1-30 μm.

[61] Method according to any of the preceding items, wherein the drug coated and dried solid dosage form after step c) comprises 0.01-25 wt.-%, preferably, 0.05-15 wt.-%, more preferably 0.1-10 wt.-%, even more preferably 0.5-5 wt.-%, even more preferably 0.7-3 wt.-%, even more preferably 0.9-2.5 wt.-%, of the at least one antibody or functional fragment thereof.

[62] Method according to any of the preceding items, wherein the drug coating comprises 0.5-60 wt.-% antibody or functional fragment thereof, 1-90 wt.-% binder, 0.001-70 wt.-% buffer and 0-20 wt.-% anti-tacking agent; preferably 5-50 wt.-% antibody or functional fragment thereof, 10-90 wt.-% binder, 0.1-60 wt.-% buffer and 0-15 wt.-% anti-tacking agent; more preferably 10-50 wt.-% antibody or functional fragment thereof, 20-85 wt.-% binder, 0.1-60 wt.-% buffer and 0.5-10 wt.-% anti-tacking agent; most preferably 20-50 wt.-% antibody or functional fragment thereof, 30-80 wt.-% binder, 1-60 wt.-% buffer and 0-8 wt.-% anti-tacking agent, relative to the total weight of the dried drug coating.

[63] Method according to any of the preceding items, further comprising, after step c), the step of
d) applying at least one additional coating in the form of a sustained release coating, by layering the solid dosage form of step c) with a sustained release coating liquid using spray coating, preferably fluidized-bed spray coating, and then drying the wet layered solid dosage form, preferably using a fluidized-bed or an oven.

[64] Method according to item 63, wherein the sustained release coating liquid comprises at least one sustained release polymer selected from the group consisting of poly(ethyl acrylate, methyl methacrylate) 2:1 (e.g. Eudragit® NM 30D, Eudragit® NE 30D); poly(ethyl acrylate, methyl methacrylate, trimethylammonioethyl methacrylate chloride) 1:2:0.1 (e.g. Eudragit® RS 30D); poly(ethyl acrylate, methyl methacrylate, trimethylammonioethyl methacrylate chloride) 1:2:0.2 (e.g. Eudragit® RL 30D); ethylcellulose (e.g. Surelease® or Aquacoat® ECD), polyvinyl acetate (eg. Kollicoat® SR 30D); and combinations thereof.

[65] Method according to item 63 or 64, wherein the solid dosage form after step d) comprises a polymer weight gain of 1-35 wt.-%, preferably 2.5-25 wt.-%, e.g. 4.5-25 wt.-%, 5-20 wt.-%, or 10-20 wt.-%, relative to the solid dosage form before step d).

[66] Method according to any of items 63 to 65, wherein the sustained release coating liquid comprises 0.1-20 wt.-%, preferably 1-15 wt.-%, more preferably 2-10 wt.-%, even more preferably 5-10 wt.-%, even more preferably 6-9 wt.-%, e.g. about 7-9 wt.-%, about 6-8.5 wt.-%, 6.5-8 wt.-%, about 7-7.5 wt.-%, or about 8 wt.-%, sustained release polymer, relative to the total weight of the sustained release coating liquid.

[67] Method according to any of items 63 to 66, wherein in step d) during drying the fluidized bed or the oven has a temperature of 40 to 65° C., preferably about 40 to 60° C.

[68] Method according to any of items 63 to 67, wherein the sustained release coating liquid further comprises an anti-tacking agent.

[69] Method according to any of items 63 to 68, wherein the sustained release coating liquid further comprises a plasticizer.

[70] Method according to any of items 63 to 69, wherein the plasticizer is selected from the group consisting of triethyl citrate (TEC), polyethylene glycol, acetyl triethyl citrate, butyl citrate, polysorbates, 1,2-polyproppylene glycol and dibutyl sebacate (DBS).

[71] Method according to any of items 63 to 70, wherein the sustained release coating liquid comprises 5-35 wt.-%, preferably 10-30 wt.-%, more preferably about 20-25 wt.-%, plasticizer, relative to the total weight of the sustained release polymer solids in the sustained release coating liquid.

[72] Method according to any of items 63 to 71, wherein the sustained release coating liquid comprises a coalescence enhancer.

[73] Method according to any of items 63 to 72, wherein the coalescence enhancer is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, fatty alcohols such as cetyl alcohol or oleyl alcohol, sodium glycolate, sodium de(s)oxycholate, polyethylene glycol, polypropylene glycol, alkyl poly(ethylene oxide), alkyl glycoside, alkyl polyglucoside, octyl glucoside, decyl maltoside, propylene glycol monolaurate (e.g. Lauroglycol 90), and combinations thereof, preferably a polysorbate, such as polysorbate 20, 28, 40, 60, 65, 80, 81 and 85; a poloxamer, such as poloxamer 124, 181, 188, 237, 331, 338 and 407; an alkyl polyglucoside (e.g., octyl glucoside and decyl maltoside); or propylene glycol monolaurate (e.g. Lauroglycol 90); more preferably propylene glycol monolaurate (e.g. Lauroglycol™ 90).

[74] Method according to any of items 63 to 73, wherein the sustained release coating liquid comprises 1-20 wt.-%, preferably 2-15 wt.-%, more preferably 5-10 wt.-%, coalescence enhancer, relative to the total weight of the sustained release polymer solids in the sustained release coating liquid.

[75] Method according to any of items 63 to 74, wherein during step d) in the spray coater the inlet air temperature is not higher than 65° C., preferably 35-60° C. and the atomising pressure at the nozzle is 25-100 kPa.

[76] Method according to any of items 63 to 75, wherein the at least one sustained release polymer is poly(ethyl acrylate, methyl methacrylate, trimethylammonioethyl methacrylate chloride) 1:2:0.1 (e.g. Eudragit® RS 30D) or poly(ethyl acrylate, methyl methacrylate, trimethylammonioethyl methacrylate chloride) 1:2:0.2 (e.g. Eudragit® RL 30D) or mixtures thereof and wherein the wet layered solid dosage form is dried in the fluidized bed or the oven, at 35 to 45° C., preferably about 40° C., for 30 min to 30 h, preferably 30 min to 24 h.

[77] Method according to item 76, wherein the sustained release coating liquid comprises about 6-8.5 wt.-%, preferably 6.5 to 8 wt.-%, more preferably about 7-7.5 wt.-%, polymer, relative to the total mass of the sustained release coating liquid.

[78] Method according to any of items 76 to 77, wherein during spray coating the inlet air temperature is about 40° C.

[79] Method according to any of items 76 to 78, wherein during the spray coating the atomising air pressure at the spray nozzle is about 25 to 100 kPa, preferably 25 to 50 kPa.

[80] Method according to any of items 76 to 79, wherein the solid dosage form after step d) comprises a polymer weight gain of 16.5-20 wt.-%, preferably about 19 wt.-%, relative to the solid dosage form before step d), and no coalescence enhancer.

[81] Method according to item 76 to 79, wherein the sustained release coating liquid comprises 5-10 wt.-% coalescence enhancer, relative to the total weight of the sustained release polymer solids in the sustained release coating liquid.

[82] Method according to item 81, wherein the coalescence enhancer is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, fatty alcohols such as cetyl alcohol or oleyl alcohol, sodium glycolate, sodium de(s)oxycholate, polyethylene glycol, polypropylene glycol, alkyl poly(ethylene oxide), alkyl glycoside, alkyl polyglucoside, octyl glucoside, decyl maltoside, propylene glycol monolaurate (e.g. Lauroglycol™ 90), and combinations thereof, preferably a polysorbate, such as polysorbate 20, 28, 40, 60, 65, 80, 81 and 85; a poloxamer, such as poloxamer 124, 181, 188, 237, 331, 338 and 407; an alkyl polyglucoside (e.g., octyl glucoside and decyl maltoside); or propylene glycol monolaurate (e.g. Lauroglycol™ 90); more preferably propylene glycol monolaurate (e.g. Lauroglycol™ 90).

[83] Method according to item 81 or 82, wherein the solid dosage form after step d) comprises a polymer weight gain of 3-10 wt.-%, preferably about 5-20 wt.-%, sustained release coating, relative to the solid dosage form before step d).

[84] Method according to any of items 81 to 83, wherein the wet solid dosage form is dried at about 40° C.

[85] Method according to any of items 81 to 84, wherein the sustained release coating further comprises an anti-tacking agent.

[86] Method according to item 85, wherein the anti-tacking agent is mesoporous silica.

[87] Method according to item 85 or 86, wherein the sustained release coating comprises 5-25 wt.-%, preferably about 10 wt.-%, anti-tacking agent, relative to the total weight of the sustained release polymer solids in the sustained release coating liquid.

[88] Method according to any of items 76 to 87, wherein the sustained release coating further comprises a plasticizer, and wherein the plasticizer preferably is DBS or TEC, more preferably TEC.

[89] Method according to item 88, wherein the sustained release coating comprises 5-35 wt.-%, preferably 15-25 wt.-%, more preferably about 20 wt.-%, plasticizer, relative to the total weight of the sustained release polymer solids in the sustained release coating liquid.

[90] Method according to any of items 63 to 75, wherein the at least one sustained release polymer is ethylcellulose aqueous dispersion, and wherein the wet layered solid dosage form is dried at 55 to 65° C., preferably about 60° C., for up to 30 h, preferably 30 min to 24 h, more preferably about 30 min to 24 h.

[91] Method according to item 90, wherein the sustained release coating liquid comprises (w/w) 6-9 wt.-%, preferably about 8 wt.-%, polymer, relative to the total mass of the sustained release coating liquid.

[92] Method according to item 90 or 91 wherein during the spray coating a fluidized-bed coater is used and wherein the inlet air temperature preferably is about 55 to 60° C.

[93] Method according to any of items 90 to 92, wherein during the spray coating the atomising air pressure at the spray nozzle is 25 to 100 kPa, preferably about 25 to 50 kPa.

[94] Method according to any of items 90 to 93, wherein the solid dosage form after step d) comprises a polymer weight gain of 3-30 wt.-%, preferably about 15-25 wt.-%, sustained release coating, relative to the solid dosage form before step d), and no coalescence enhancer.

[95] Method according to any of items 90 to 94, wherein the sustained release coating liquid comprises 5 to 15 wt.-%, preferably about 10 wt.-%, coalescence enhancer, relative to the total weight of the sustained release polymer solids in the sustained release coating liquid.

[96] Method according to item 95, wherein the coalescence enhancer is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, fatty alcohols such as cetyl alcohol or oleyl alcohol, sodium glycolate, sodium de(s)oxycholate, polyethylene glycol, polypropylene glycol, alkyl poly(ethylene oxide), alkyl glycoside, alkyl polyglucoside, octyl glucoside, decyl maltoside, propylene glycol monolaurate (e.g. Lauroglycol™ 90), and combinations thereof, preferably a polysorbate, such as polysorbate 20, 28, 40, 60, 65, 80, 81 and 85; a poloxamer, such as poloxamer 124, 181, 188, 237, 331, 338 and 407; an alkyl polyglucoside (e.g., octyl glucoside and decyl maltoside); or propylene glycol monolaurate (e.g. Lauroglycol™ 90); more preferably propylene glycol monolaurate (e.g. Lauroglycol™ 90).

[97] Method according to any of items 95 or 96, wherein the solid dosage form after step d) comprises a polymer weight gain of 3-20 wt.-%, relative to the solid dosage form before step d).

[98] Method according to any of items 95 to 97, wherein the wet solid dosage form is dried at about 60° C. for 30 min to 24 h, preferably for 30 min to 10 h.

[99] Method according to any of items 90 to 98, wherein the sustained release coating further comprises a plasticizer.

[100] Method according to item 99, wherein the plasticizer is TEC or DBS, preferably DBS.

[101] Method according to any of items 90 to 100, wherein the sustained release coating comprises 5-35 wt.-%, preferably 10-25 wt.-%, more preferably about 25 wt.-%, plasticizer, relative to the total weight of the sustained release polymer solids in the sustained release coating liquid.

[102] Method according to any of items 40 to 101 wherein the sustained release coating, or the sustained release polymeric binder in the drug coating, gives rise to a release profile for the at least one antibody or fragment thereof, where a sustained release with a substantially constant release rate of at least 80%, preferably at least 90%, of the at least one antibody or fragment thereof in the solid dosage form is achieved over 4-30 h, preferably 8-24 h, more preferably 16-24 h, even more preferably 24 h, upon continuously immersing the solid dosage form in an aqueous solution under continuous agitation.

[103] Method according to any of items 40 to 102, wherein the amount of sustained release coating relative to the total weight of the solid dosage form after step d), or the amount of the sustained release polymeric binder in the drug coating relative to the total weight of the drug coating, directly correlates with the rate of release of the at least one antibody or functional fragment thereof from the solid dosage form, such that a higher amount of sustained release coating or a higher amount of sustained release polymeric binder in the drug coating results in a slower release rate.

[104] Method according to any of the preceding items, wherein the active agent coating liquid in step a) and/or the sustained release coating liquid in step d) comprise at least one surfactant.

[105] Method according to item 104, wherein the active agent coating liquid and/or the sustained release coating liquid comprise 0.005 to 2.0 wt.-%, 0.01 to 1 wt.-%, more preferably 0.05 to 0.8 wt.-%, even more preferably about 0.1 to 0.5 wt.-% surfactant.

[106] Method according to item 104 or 105, wherein the surfactant is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, cetyl alcohol, oleyl alcohol, sodium glycolate, sodium de(s)oxycholate, polyethylene glycol, polypropylene glycol, alkyl poly(ethylene oxide), alkyl glycoside, alkyl polyglucoside, octyl glucoside, decyl maltoside, and combinations thereof.

[107] Method according to any of the preceding items, wherein the active agent coating liquid in step a) and/or the sustained release coating liquid in step d) comprise at least one further excipient selected from antioxidants, humectants, protective colloids, dyes, fillers, protease inhibitors, permeation enhancers, and combinations thereof.

[108] Method according to any of the preceding items, wherein the solid dosage form comprises an amount of the at least one antibody or functional fragment thereof that allows the administration of a therapeutically effective dose of the at least one antibody or functional fragment thereof as a single unit dose.

[109] Method according to any of the preceding items, wherein the functional antibody fragment is a Fab fragment, a F(ab')2 fragment, a Fab' fragment, an scFv, a dsFv, a VHH, a diabody, a triabody, a tetrabody, an Fc fusion protein or a minibody.

[110] Method according to any of the preceding items, wherein the at least one antibody or functional fragment thereof is selected from antibodies specific to tumor necrosis factor alpha (TNFα) and functional fragments thereof, antibodies specific to α4β7 integrin and functional fragments thereof, antibodies specific to CD3, CD4 or CD20 and functional fragments thereof, antibodies specific to interleukin 6 (IL-6), interleukin 12 (IL-12), interleukin 13 (IL-13), interleukin 23 (IL-23) or to their receptors and functional fragments thereof, antibodies specific to CXCL10/IP-10 and functional fragments thereof, and antibodies specific to p40 protein subunit and functional fragments thereof.

[111] Method according to any of the preceding items, wherein the antibody or functional fragment thereof is suitable for use in the treatment of an inflammatory bowel disease (IBD), like Crohn's disease or ulcerative colitis.

[112] Method according to any of the preceding items, wherein the at least one antibody or functional fragment thereof is selected from infliximab, adalimumab, etanercept, certolizumab pegol, golimumab, visilizumab, eldelumab, abrilumab, canakinumab, tocilizumab, ustekinumab, natalizumab, etrolizumab, priliximab, vedolizumab and functional fragments thereof; from anti-TNFα antibodies or functional fragments thereof with light chain variable domains and/or heavy chain variable domains comprising complementarity-determining regions (CDRs) with amino acid sequences as disclosed in claim 2 of PCT/EP2017/056218, in claim 2 of PCT/EP2017/056246, in claim 2 of PCT/EP2017/056237 and/or in claim 2 of PCT/EP2017/056227, as originally filed; from anti-TNFα antibodies or functional fragments thereof comprising a heavy chain variable domain amino acid sequence and/or a light chain variable domain amino acid sequence according to claim 4 of PCT/EP2017/056218, claims 5 and 6 of PCT/EP2017/056246, claims 5 and 6 of PCT/EP2017/056237, and/or claim 4 of PCT/EP2017/056227, as originally filed; and combinations thereof.

[113] Method according to any of the preceding items, wherein the antibody or functional fragment thereof is selected from antibodies specific to TNFα and functional fragments thereof.

[114] Method according to item 113, wherein the antibody specific to TNFα or functional fragment thereof is selected from infliximab, adalimumab, etanercept, certolizumab pegol, golimumab and functional fragments thereof; from anti-TNFα antibodies or functional fragments thereof with light chain variable domains and/or heavy chain variable domains comprising complementarity-determining regions (CDRs) with amino acid sequences as disclosed in claim 2 of PCT/EP2017/056218, in claim 2 of PCT/EP2017/056246, in claim 2 of PCT/EP2017/056237 and/or in claim 2 of PCT/EP2017/056227, as originally filed; from anti-TNFα antibodies or functional fragments thereof comprising a heavy chain variable domain amino acid sequence and/or a light chain variable domain amino acid sequence according to claim 4 of PCT/EP2017/056218, claims 5 and 6 of PCT/EP2017/056246, claims 5 and 6 of PCT/EP2017/056237, and/or claim 4 of PCT/EP2017/056227, as originally filed; and combinations thereof.

[115] Method according to any of the preceding items, wherein at any time during steps a) and c) the temperature of the at least one antibody or functional fragment thereof is lower than the melting temperature (Tm) of the at least one antibody or functional fragment thereof.

[116] Method according to any of the preceding items, wherein at any time during steps a) and c) the temperature of the antibody or functional fragment thereof is lower than 65° C., preferably not higher than 60° C., more preferably not higher than 55° C., more preferably about 45 to 50° C.

[117] Method according to any of items 63 to 116, wherein step d) is carried out at a temperature not higher than 65° C., preferably not higher than 60° C.

[118] Method according to any of items 63 to 117, wherein step d) is carried out at a temperature lower than the melting temperature (Tm) of the at least one antibody or functional fragment thereof in the solid dosage form.

[119] Method according to any of items 63 to 116, wherein at any time during steps a) and d) the temperature of the at least one antibody or functional fragment thereof is lower than the melting temperature (Tm) of the at least one antibody or functional fragment thereof.

[120] Method according to any of items 63 to 119, wherein during step d) an ethylcellulose aqueous dispersion is used and wherein step d) is carried out at a temperature lower than 65° C., preferably not higher than 60° C.

[121] Method according to any of items 63 to 119, wherein during step d) poly(ethyl acrylate, methyl methacrylate, trimethylammonioethyl methacrylate chloride) 1:2:0.1 (e.g. Eudragit® RS 30D) or poly(ethyl acrylate, methyl methacrylate, trimethylammonioethyl methacrylate chloride) 1:2:0.2 (e.g. Eudragit® RL 30D) or mixtures thereof aqueous dispersion is used and wherein step d) is carried out at a temperature lower than 55° C., preferably not higher than 50° C., more preferably not higher than 45° C.

[122] Method according to any of the preceding items, wherein the solid dosage form is a sustained release dosage form, allowing a sustained release of the at least one antibody or functional fragment thereof over a time period of at least 5 h, preferably at least 10 h, more preferably at least 12 h, even more preferably at least 15 h, even more preferably at least 20 h, most preferably at least 24 h, upon continuously immersing the solid dosage form in an aqueous solution under continuous agitation.

[123] Method according to any of the preceding items, wherein after drying in step c), or after step d) if at least one additional coating in the form of a sustained release coating is applied as step d), the moisture in the solid dosage form is less than 10 wt.-%, preferably less than 8 wt.-%, more preferably less than 5 wt.-%, even more preferably less than 3 wt.-%, even more preferably less than 1.5 wt.-% most preferably less than 1 wt.-%, relative to the total weight of the solid dosage form after step c) or after step d), respectively.

[124] Method according to any of the above items, wherein the solid dosage form is intended for oral administration.

[125] Method according to any one of the preceding items, further comprising, after step c), or after step d) if at least one additional coating in the form of a sustained release coating is applied as step d), the step of applying at least one additional coating in the form of a delayed release coating, and wherein the solid dosage form is for oral administration.

[126] Method according to item 125, wherein the delayed release coating is applied by spray coating, preferably fluidized-bed spray coating.

[127] Method according to item 125 or 126, wherein the delayed release coating comprises at least one component selected from coating materials that disintegrate pH-dependently; coating materials that disintegrate time-dependently; coating materials that disintegrate due to enzymatic triggers in the intestinal environment; and combinations thereof.

[128] Method according to item 127, wherein
   the coating materials that disintegrate pH-dependently are selected from poly vinyl acetate phthalate; cellulose acetate trimellitate; hydroxypropyl methylcellulose phthalate HP-50, HP-55 or HP-55S; cellulose acetate phthalate; hydroxypropyl methylcellulose acetate succinate (HPMCAS); poly(methacrylic acid, ethyl acrylate) 1:1 (Eudragit® L100-55, Eudragit® L30D-55); poly(methacrylic acid, methyl methacrylate) 1:1 (Eudragit® L-100, Eudragit® L12.5); poly(methacrylic acid, methyl methacrylate) 1:2 (Eudragit® S-100, Eudragit® S12.5, Eudragit® FS30D), and combinations thereof;
   the coating materials that disintegrate time-dependently are selected from poly(ethyl acrylate, methyl methacrylate) 2:1 (e.g. Eudragit® NM 30D); poly(ethyl acrylate, methyl methacrylate, trimethylammonioethyl methacrylate chloride) 1:2:0.1 (e.g. Eudragit® RS 30D); ethylcellulose (e.g. Surelease® or Aquacoat® ECD); poly(ethyl acrylate, methyl methacrylate, trimethylammonioethyl methacrylate chloride) 1:2:0.2 (e.g. Eudragit® RL 30D); polyvinyl acetate (eg. Kollicoat® SR 30D); and combinations thereof; and
   the coating materials that disintegrate due to enzymatic triggers in the intestinal environment are selected from chondroitin sulfate; cyclodextrin; pectin; guar gum; chitosan; inulin; lactulose; raffinose; stachyose; alginate; dextran; xanthan gum; locust bean gum; arabinogalactan; amylose; pullulan; carrageenan; scleroglucan; chitin; curdulan; levan; amylopectin; starch; resistant starch; azo compounds being degraded by azo bonds splitting bacteria; and combinations thereof.

[129] Method according to any of items 125 to 128, wherein the delayed release coating comprises a combination of at least one coating material that disintegrates pH-dependently and at least one coating material that disintegrates due to enzymatic triggers in the intestinal environment.

[130] Method according to any one of items 125 to 129, wherein the delayed release coating comprises a combination of at least one enteric polymer, preferably poly(methacrylic acid, methyl methacrylate) 1:2 (e.g. Eudragit® S), and at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, preferably resistant starch.

[131] Method according to any one of items 125 to 130, wherein the delayed release coating comprises i) an inner coating comprising a partially neutralized enteric polymer adjusted to pH 8, e.g. partially neutralized poly(methacrylic acid, methyl methacrylate 1:2 (Eudragit® S) adjusted to pH 8, and containing a buffer salt, and ii) an outer coating comprising a combination of at least one enteric polymer, preferably poly(methacrylic acid, methyl methacrylate) 1:2 (Eudragit® S), and at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, preferably resistant starch.

[132] Method according item 130 or 131, wherein the at least one component, e.g. the combination of the at least one enteric polymer, preferably poly(methacrylic acid, methyl methacrylate) 1:2 (e.g. Eudragit® S), and the at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, preferably resistant starch, is dispersed in an organic solvent, a mixture of organic solvents or a mixture of at least one organic solvent and water, which is applied to the solid dosage form, e.g. by spray coating, preferably fluidized-bed spray coating.

[133] Method according item 132, wherein the combination is dispersed in a mixture of at least one organic solvent and water, prepared by mixing a enteric polymer dissolved in an organic solvent with an aqueous re-dispersion of the at least one polysaccharide

[134] Method according to any one of items 125 to 133, wherein the delayed release coating is applied by spray coating, preferably fluidized-bed spray coating.

[135] Method according to any one of items 125 to 134, comprising a delayed release coating for targeted release of the at least one antibody or functional fragment thereof starting in the terminal ileum, the ileocolonic region, the ascending colon, transverse colon or the descending colon.

[136] Method according to any of the preceding items wherein the fraction of total content of antibody or functional fragment thereof present in the solid dosage form as dimers and other aggregates does not exceed by more than 15%, preferably 12%, more preferably 10%, even more preferably 8%, even more preferably 7%, even more preferably 5%, even more preferably 3%, 2%, or 1.5%, the fraction of total antibody or functional fragment thereof present as dimers and other aggregates at the time of adding the antibody or functional fragment thereof to the active agent coating liquid.

[137] Method according to any of the preceding items wherein the fraction of total content of antibody or functional fragment thereof present in the solid dosage form as fragments of the full-length antibody or functional fragment thereof does not increase substantially compared to the time of adding the antibody or functional fragment thereof to the active agent coating liquid.

[138] Method according to any of the preceding items wherein the fraction of total content of antibody or functional fragment thereof present in the solid dosage form as fragments of the full-length antibody or functional fragment thereof does not exceed by more than 15%, preferably 12%, more preferably 10%, even more preferably 8%, even more preferably 7%, even more preferably 5%, even more preferably 3%, 2%, or 1.5%, the fraction of total content of antibody or functional fragment thereof present as fragments of the full-length antibody or functional fragment thereof at the time of adding the antibody or functional fragment thereof to the active agent coating liquid.

[139] Method according to any of the preceding items, wherein the solid dosage form comprises an immediate release drug coating, allowing the recovery of at least 70%, preferably at least 80%, more preferably at least 90%, even more preferably at least 95%, even more preferably at least 97%, even more preferably at least 99%, of the at least one antibody or functional fragment thereof from the drug coating within 1 h of continuously immersing a solid dosage form, with the drug coating as the outermost coating, in an aqueous solution under continuous agitation.

[140] Method according to any of the preceding items, wherein the polymeric binder in the drug coating comprises at least one sustained release polymeric binder, allowing the recovery of at least 40%, preferably at least 50%, more preferably at least 60%, even more preferably at least 70%, even more preferably at least 80%, even more preferably at least 85%, even more preferably at least 90%, even more preferably at least 93%, most preferably at least 95%, of the at least one antibody or functional fragment thereof from the drug coating within 4 h, or 6 h, or 8 h, or 10 h, or 12 h, or 14 h, or 16 h, or 18 h, or 20 h, or 22 h, or 24 h, or 26 h, or 28 h, or 30 h, etc., of continuously immersing the solid dosage form in an aqueous solution under continuous agitation.

[141] Method according to any of the previous items, comprising the further step of providing a multiparticulate drug delivery system, e.g. a sachet/stick pack, straw device (XStraw®), tablet/mini tablet or a capsule, preferably comprising a total amount of the at least one antibody or functional fragment thereof suitable for oral administration to a human patient.

[142] A solid dosage form obtainable by the method of any one of items 1 to 141.

[143] Solid dosage form according to item 142 for use in the topical treatment of a gastrointestinal disease, preferably an IBD, colorectal cancer, small intestine cancer, celiac disease, a gastrointestinal infections (e.g. Clostridium difficile infection), more preferably an IBD.

[144] Solid dosage form for use according to item 143, wherein the IBD is Crohn's disease or ulcerative colitis.

[145] Solid dosage form according to any one of items 142 to 144 for use in the topical treatment in the terminal ileum, the ileocolonic region, the ascending colon, transverse colon or the descending colon of a patient.

[146] A multiparticulate drug delivery system, comprising multiple solid dosage forms, each of the solid dosage forms obtainable by the method of any one of items 1 to 141, wherein the multiparticulate drug delivery system preferably is a sachet/stick pack, a straw device (XStraw®), capsule, or tablet/mini tablet.

[147] A multiparticulate drug delivery system comprising a plurality of solid dosage form units, each solid dosage form unit comprising i) an inert core unit, and ii) a drug coating comprising at least one antibody or functional fragment thereof, a buffer and at least one polymeric binder, and optionally an anti-tacking agent and/or a surfactant, and each solid dosage form unit preferably having a predetermined axis and the same predetermined cross-sectional profile, wherein at least 80% by number of those solid dosage form units, preferably 90%, more preferably 95%, have a median aspect ratio between 0.7 and 1.7, the aspect ratio being defined as solid dosage form unit length along the predetermined axis divided by the smallest cross-sectional dimension.

[148] A multiparticulate drug delivery system according to item 147, wherein the median aspect ratio is above 0.8, preferably above 0.9, and below 1.6, preferably below 1.5, more preferably 1.4, even more preferably below 1.3, even more preferably below 1.2, most preferably about 1.

[149] Multiparticulate drug delivery system according to item 147 or 148, wherein the solid dosage form units have a span of aspect ratio of less than 0.9, preferably less than 0.8, more preferably less than 0.7, even more preferably less than 0.6, most preferably less than 0.5.

[150] Multiparticulate drug delivery system according to any of items 147 to 149, allowing the recovery of at least 80%, preferably at least 85%, more preferably at least 93%, even more preferably at least 95%, even more preferably at least 97%, even more preferably at least 98%, of the at least one antibody or functional fragment thereof from the solid dosage form units.

[151] Multiparticulate drug delivery system according to any of items 147 to 150, allowing the recovery of at least 80%, preferably at least 85%, more preferably at least 93%, even more preferably at least 95%, even more preferably at least 97%, even more preferably at least 98%, of the at least one antibody or functional fragment thereof from the solid dosage form units, within 30 min, or 1 h, or 2 h, of continuously immersing the solid dosage form in an aqueous solution under continuous agitation (immediate release).

[152] Multiparticulate drug delivery system according to any of items 147 to 150, wherein the solid dosage form units comprised in the multiparticulate drug delivery system are sustained release solid dosage form units.

[153] Multiparticulate drug delivery system according to any of items 150 or 152, allowing the recovery of at least 80%, preferably at least 85%, more preferably at least 93%, even more preferably at least 95%, even more preferably at least 97%, even more preferably at least 98%, of the at least one antibody or functional fragment thereof from the solid dosage form units, within 4 h, or 6 h, or 8 h, or 10 h, or 12 h, or 14 h, or 16 h, or 18 h, or 20 h, or 22 h, or 24 h, or 26 h, or 28 h, or 30 h, or 32 h, or 34 h, or 36 h, etc., of continuously immersing the solid dosage form in an aqueous solution under continuous agitation (sustained release).

[154] Multiparticulate drug delivery system according to any of items 147 to 153, wherein the solid dosage form units comprise the antibody or functional fragment thereof, buffer and at least one polymeric binder in a drug coating which is applied to an inert core unit by spray coating.

[155] Multiparticulate drug delivery system according to any of items 147 or 154, wherein the solid dosage form units comprise at least one additional coating in the form of a sustained release coating, and wherein the sustained release coating preferably has the properties as defined in any one of items 64 to 75.

[156] Multiparticulate drug delivery system according to any of items 147 or 155, wherein the solid dosage form units are solid dosage forms prepared by drug layering according to the method of any one of items 1 to 141.

[157] Multiparticulate drug delivery system according to any of items 147 to 156, wherein the multiparticulate drug delivery system is prepared from multiple solid dosage form units by compression, encapsulation.

[158] Multiparticulate drug delivery system according to any one of items 147 to 157, wherein the at least one antibody or functional fragment thereof is as defined in any one of items 109-114; and/or wherein the buffer is as defined in item 58; and/or wherein the at least one polymeric binder is as defined in any one of items 36-37 and 46-48, and/or wherein the optional anti-tacking agent and/or surfactant and/or further additives is/are as defined in any one of items 49-50, 52-53, 55-56 and 106.

[159] Multiparticulate drug delivery system according to any one of items 147 to 158, wherein the single dosage form units have the properties as defined in any one of items 61, 62 and 108.

[160] Multiparticulate drug delivery system according to any of items 147 to 159, wherein the multiparticulate drug delivery system or the individual solid dosage form units further comprise a delayed release coating, which is applied as a further coating, and wherein the delayed release coating preferably is as define in any one of items 126 to 135.

[161] A solid dosage form consisting of a single dosage form unit comprised in the multiparticulate drug delivery system according to any one of items 147 to 160.

BRIEF DESCRIPTION OF THE DRAWINGS

FIG. 5A presents a batch summary. FIG. 5B shows adalimumab release from Eudragit® RS 30D coated pellets (Example 6, 7 and 8) in citrate-TRIS pH 7 buffer in comparison to immediate release adalimumab layered pellets (Comparative Example 1). Results are expressed as mean of 3 replicates with corresponding standard deviation. FIG. 5C shows the relative adalimumab aggregation and fragmentation profile of dissolution samples from Example 8 pellets in comparison to the adalimumab standard.

FIG. 9A-B showed that adalimumab integrity is kept and adalimumab is able to bind to TNFα. For comparison reasons the results of total protein quantification (B) and ELISA (E) are represented in FIG. 9A-B.

DETAILED DESCRIPTION OF THE PREFERRED EMBODIMENTS

Figure 1A:
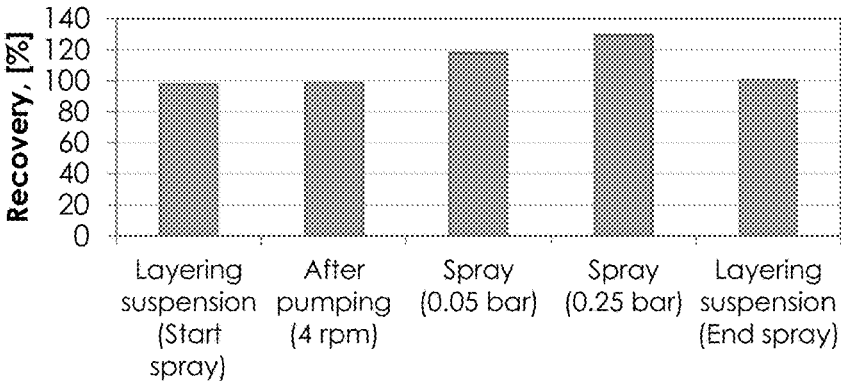
FIGS. 1A-1C provide a composition summary of coating suspensions and process effects on adalimumab. The effect of some process variables on adalimumab in an HPMC-Syloid® 244 FP suspension containing 5 mg/mL adalimumab was assessed in terms of total protein content, aggregation and fragmentation (FIG. 1A to 1C). No significant increase in dimer content (FIG. 1B) in comparison to the positive control (1.0 mg/mL standard) was observed for the samples collected during the process. Similarly no significant increase of fragments was seen in comparison to the positive control (FIG. 1C)

The present invention relates to a method for preparing a solid dosage form comprising i) an inert core unit; and ii) a drug coating comprising at least one antibody or functional fragment thereof as active agent, a buffer and at least one polymeric binder, deposited on the inert core unit by drug layering; the method comprising the steps of a) preparing an active agent coating liquid, comprising the at least one antibody or functional fragment thereof, the buffer and the at least one polymeric binder, as an aqueous solution or suspension; b) layering the inert core unit with the active agent coating liquid using spray coating, preferably fluid-ized-bed spray coating; and c) drying the wet drug layered inert core unit, simultaneously with step b), or after step b) has been completed, to give rise to a dried solid dosage form.

The term "solid dosage form" as used herein may be understood to be equivalent to "solid pharmaceutical dosage form" or "pharmaceutical composition formulated into a solid dosage form" and includes for example pellets, cap-sules, granules, tablet, mini tablets and the like. In one embodiment of the present invention the solid dosage form is a pellet, sphere mini sphere, bead, granule, tablet or mini tablet. In a preferred embodiment of the present invention the solid dosage form is a pellet. Multiple solid dosage forms of the present invention may be combined into a single-unit formulation, for example in the form of a tablet, hard gelatin capsule, sachet, caplet, or pill.

The term "inert core unit" as used herein is not particu-larly limited. The term "inert core unit" as used herein may be understood to mean inert pellet, mini tablet, tablet, granule, core, bead, mini sphere or sphere, which consists of one or more of soluble or insoluble inert materials and the like, which are all pharmacologically inactive. Alternatively, the term "inert core unit" may be understood to mean an inert pellet, mini-tablet, tablet, granule, core, bead, mini sphere or sphere already comprising at least one active agent. If the inert core unit comprises at least one active agent, the at least one active agent preferably is in the form of at least one antibody or functional fragment thereof. This at least one antibody or functional fragment thereof com-prised in the inert core unit may be the same or different from the one in the drug coat. The inert core unit may be optionally seal coated to increase the strength of the core to withstand the mechanical pressures during processing.

The inert core unit is "inert" in relation to the at least one antibody or functional fragment thereof in the drug coating. That is, it does not reduce stability and activity of the at least one antibody or functional fragment thereof in the drug coating under the conditions used during preparation of the solid dosage form by the inventive method, its storage and later administration and dissolution.

The term "about", as used herein, indicates the value or range of a given quantity can include quantities ranging within 10% of the stated value or range, or optionally within 5% of the value or range, or in some embodiments within 1% of the value or range. In an embodiment where the inert core unit comprises at least one active agent, the solid dosage form prepared by the inventive method may be designed to release the active agent in the inert core unit simultaneously with the at least one antibody or functional fragment thereof in the drug coating, or may be designed to release at different rates and/or times. According to one embodiment of the present invention the active agent in the inert core unit is released simultaneously with the at least one antibody or functional fragment thereof in the drug coating. According to another embodiment of the present invention the active agent in the inert core unit is not released simultaneously with the at least one antibody or functional fragment thereof in the drug coating. For example, if the active agent in the inert core unit is not released simultaneously with the at least one antibody or functional fragment thereof in the drug coating, its release may start later and/or with a faster/slower release rate than the at least one antibody or functional fragment thereof in the drug coating.

An inert core unit may be a pellet, mini pellet, sphere, mini sphere, granule, bead, mini tablet or tablet, e.g. pre-pared from a mixture of excipients and optionally active agents by compression, extrusion-spheronization or encap-sulation. In one embodiment of the present invention, the inert core unit comprises a monosaccharide, disaccharide, oligosaccharide, polysaccharide, silica, tartaric acid, cal-cium carbonate, or a combination thereof as a main com-ponent. In a specific embodiment, the inert core unit com-prises microcrystalline cellulose, sucrose, starch, mannitol, calcium carbonate, silica, tartaric acid, lactose, or a combi-nation thereof as a main component. In another embodiment of the present invention, the inert core unit is pharmaco-logically inactive and comprises a monosaccharide, disac-charide, oligosaccharide, polysaccharide, silica, tartaric acid, calcium carbonate, or a combination thereof, prefer-ably microcrystalline cellulose, sucrose, starch, mannitol, calcium carbonate, silica, tartaric acid, lactose, or a combi-nation thereof, as a main component. "Main component" in this context refers to an inert core unit comprising at least 50 wt.-%, preferably at least 70 wt.-%, more preferably at least 90 wt.-%, even more preferably at least 95 wt.-%, of said component. As used in the context of the inert core unit above, "wt.-%" refers to the weight percent of a substance relative to the weight of the inert core unit.

Generally, unless otherwise indicated, "wt.-%" as used herein, refers to the weight percent of a substance relative to the total weight of the overall solid dosage form. In some cases where indicated, "wt.-%" may refer to the weight percent of a substance relative to the weight of the solid dosage form after a specifically indicated step in the prepa-ration thereof.

In one embodiment the inert core unit is a pellet. The pellet may have a median particle size of 50-10000 μm, preferably 100-3000 μm, more preferably 350-2000 μm, even more preferably 500-1500 μm, most preferably 700-1200 μm. In another embodiment, the inert core unit is a pellet with a particle size distribution such that at least 85% of the pellets have a particle size of 50-3000 μm, preferably 100-1500 μm, more preferably 350-1400 μm, even more preferably 500-1200 μm, most preferably 700-1200 μm.

The shape of the pellet is not particularly limited. In one embodiment, the inert core unit is a pellet with a sphericity degree of at least 0.6, preferably at least 0.7, more preferably at least 0.8, even more preferably at least 0.9, even more preferably at least 0.95. In a preferred embodiment the inert core unit is a pellet comprising a sphere. The term "sphere" as used herein refers to a particle with a sphericity degree of at least 0.8. The sphere may be coated with a coating deposited on the sphere, e.g. a seal coated. The sphere may consist of microcrystalline cellulose, sucrose, starch, man-nitol, calcium carbonate, silica, tartaric acid, lactose or a combination thereof. In another embodiment the inert core unit is a pellet consisting of a sphere consisting of microc-rystalline cellulose, sucrose, starch, mannitol, calcium car-bonate, silica, tartaric acid, lactose or a combination thereof, preferably microcrystalline cellulose. Examples of commer-cially available inert core units include CELLETS® (Phar-matrans-Sanaq AG) and SUGLETS® sugar spheres (Color-con® Ldt).

The term "drug coating" as used herein refers to a coating or coat, comprising at least one active agent, in the form of at least one antibody or functional fragments thereof, which is deposited onto the inert core unit. The term "coating" or "coat" as used herein, refers to a film comprising one or more layers. A specific coating can be separated from the inert core unit, or further coatings that may be applied separately, by its distinct physicochemical properties. Consequently, the drug coating can be separated from the inert core unit and further coatings that may be applied separately after the drug coating, by its distinct physicochemical properties.

The term "antibody", in the context of the present invention, refers to "immunoglobulin" (Ig), which is defined as a protein belonging to the class IgG, IgM, IgE, IgA, or IgD (or any subclass thereof), and includes all conventionally known antibodies and functional fragments thereof. The at least one antibody or functional fragment thereof used for the present invention is an active agent, i.e. the at least one antibody or functional fragment thereof is incorporated into the solid dosage form due to the pharmacological activity of the antibody or functional fragment thereof in a patient.

In the context of the present invention, a "functional fragment" of an antibody/immunoglobulin is defined as antigen-binding fragment or other derivative of a parental antibody that essentially maintains the properties of such a parental antibody. An "antigen-binding fragment" of an antibody/immunoglobulin is defined as a fragment (e.g., a variable region of an IgG) that retains the antigen-binding region. An "antigen-binding region" of an antibody typically is found in one or more hypervariable region(s) of an antibody, i.e., the CDR-1, -2, and/or -3 regions. "Antigen-binding fragments" according to the invention include the domain of a F(ab')$_2$ fragment and a Fab fragment. "Functional fragments" of the invention include Fab fragment, F(ab')$_2$ fragment, Fab' fragment, scFv, dsFv, VHH, diabody, triabody, tetrabody, Fc fusion protein and minibody. The F(ab')$_2$ or Fab domain may be engineered to minimize or completely remove the intermolecular disulphide interactions that occur between the CH1 and CL domains. The antibodies or functional fragments thereof used for the present invention may be part of bi- or multifunctional constructs.

Fab fragments can be obtained as the purified digestion products after digestion of an antibody with a cysteine proteinase like papain (EC 3.4.22.2). F(ab')$_2$ fragments can be obtained as the purified digestion products after digestion of an antibody with pepsin (EC 3.4.23.1) or IdeS (Immunoglobulin degrading enzyme from *Streptococcus pyogenes*; EC 3.4.22). Fab' fragments can be obtained from F(ab')$_2$ fragments in mild reducing conditions, whereby each F(ab')$_2$ molecule gives rise to two Fab' fragments. An scFv is a single chain Fv fragment in which the variable light ("V$_L$") and variable heavy ("V$_H$") domains are linked by a peptide bridge.

A "diabody" is a dimer consisting of two fragments, each having variable regions joined together via a linker or the like (hereinafter referred to as diabody-forming fragments), and typically contain two V$_L$s and two V$_H$s. Diabody-forming fragments include those consisting of V$_L$ and V$_H$, V$_L$ and V$_L$, V$_H$ and V$_H$, etc., preferably V$_H$ and V$_L$. In diabody-forming fragments, the linker joining variable regions is not specifically limited, but preferably short enough to avoid noncovalent bonds between variable regions in the same fragment. The length of such a linker can be determined as appropriate by those skilled in the art, but typically 2-14 amino acids, preferably 3-9 amino acids, especially 4-6 amino acids are used. In this case, the V$_L$ and V$_H$ encoded on the same fragment are joined via a linker short enough to avoid noncovalent bonds between the V$_L$ and V$_H$ on the same chain and to avoid the formation of single-chain variable region fragments so that dimers with another fragment can be formed. The dimers can be formed via either covalent or noncovalent bonds or both between diabody-forming fragments.

Moreover, diabody-forming fragments can be joined via a linker or the like to form single-chain diabodies (sc(Fv)$_2$). By joining diabody-forming fragments using a long linker of about 15-20 amino acids, noncovalent bonds can be formed between diabody-forming fragments existing on the same chain to form dimers. Based on the same principle as for preparing diabodies, polymerized antibodies such as trimers or tetramers can also be prepared by joining three or more diabody-forming fragments.

In one embodiment, the functional fragment in the solid dosage form prepared by the inventive method is a Fab fragment, a F(ab')$_2$ fragment, a Fab' fragment, an scFv, a dsFv, a VHH, a diabody, a triabody, a tetrabody, an Fc fusion protein or a minibody. Preferred functional fragments used in the present invention are Fab fragments, F(ab')$_2$ fragments, Fab' fragments, scFv and diabodies.

The antibody or functional fragment thereof used in the inventive method for the preparation of the solid dosage form is not particularly limited. In one embodiment, the antibody or functional fragment thereof is an antibody. In another embodiment of the present invention, the antibody or functional fragment thereof is functional fragment as defined above. The antibody or functional fragment thereof may further comprise one or more modifications, e.g. in the form of added or substituted residues, that improve stability, specificity or targeting. These may include any such modifications that are known in the art.

The antigen against which the antibody or functional fragment is directed i.e. the immunogen, peptide, protein, or other molecular structure to which the antibody or functional fragment thereof can specifically bind, is not limited. In its most general form (and when no defined reference is mentioned), "specific to" or "specific binding" refers to the ability of the antibody or functional fragment thereof to discriminate between the target of interest and an unrelated biomolecule (e.g. for antibodies specific to human TNFα to discriminate between human TNFα and an unrelated biomolecule), as determined, for example, in accordance with specificity assay methods known in the art. Such methods comprise, but are not limited to, Western blots and enzyme-linked immunosorbent assay (ELISA) tests. For example, a standard ELISA assay can be carried out. Typically, determination of binding specificity is performed by using not a single reference biomolecule, but a set of about three to five unrelated biomolecules, such as milk powder, BSA, transferrin or the like. In one embodiment of the present invention the antibody or functional fragment thereof is suitable for use in the treatment of an inflammatory bowel disease (IBD), e.g. Crohn's disease or ulcerative colitis. In another embodiment of the present invention the antibody or functional fragment thereof is suitable for use in the topical treatment in the ileum or large intestine of the gastrointestinal tract of a patient.

In a further embodiment of the present invention the antibody or functional fragment thereof is selected from antibodies specific to tumor necrosis factor alpha (TNFα) and functional fragments thereof, antibodies specific to α4β7 integrin and functional fragments thereof, antibodies specific to CD3, CD4 or CD20 and functional fragments thereof, antibodies specific to interleukin 6 (IL-6), interleukin 12 (IL-12), interleukin 13 (IL-13), interleukin 23 (IL-23) or to their receptors and functional fragments thereof, antibodies specific to CXCL10/IP-10 and functional fragments thereof, and antibodies specific to p40 protein subunit and functional fragments thereof. In yet another embodiment of the present invention the antibody or functional fragment thereof is selected from infliximab, adalimumab, etanercept, certolizumab pegol, golimumab, visilizumab, eldelumab, abrilumab, canakinumab, tocilizumab, ustekinumab, natalizumab, etrolizumab, priliximab, vedolizumab and functional fragments thereof.

In one embodiment of the present invention, the antibody or functional fragment thereof in the solid dosage form prepared by the inventive method specifically binds to TNFα. The terms "anti-TNFα antibody", "TNFα antibody" and "antibody specific to TNFα" as used herein are interchangeable. In one embodiment, specific binding refers to the ability of the antibody or fragment to discriminate between human TNFα and human TNFβ. In a preferred embodiment of the present invention the TNFα antibody or functional fragment thereof is a TNFα antibody. In an alternatively preferred embodiment of the present invention the TNFα antibody or functional fragment thereof is a functional fragment of a TNFα antibody.

Several monoclonal antibodies against TNFα have been described in the prior art. Meager et al. (Hybridoma, 6, 305-311, 1987) describe murine monoclonal antibodies against recombinant TNFα. Fendly et al. (Hybridoma, 6, 359-370, 1987) describe the use of murine monoclonal antibodies against recombinant TNFα in defining neutralising epitopes on TNF. Furthermore, in international patent application WO 92/11383, recombinant antibodies, including CDR-grafted antibodies, specific for TNFα are disclosed. U.S. Pat. No. 5,919,452 discloses anti-TNFα chimeric antibodies and their use in treating pathologies associated with the presence of TNFα. Further anti-TNFα antibodies are disclosed in Stephens et al. (Immunology, 85, 668-674, 1995), GB-A-2 246 570, GB-A-2 297 145, U.S. Pat. No. 8,673,310, US 2014/0193400, EP 2 390 267 B1, U.S. Pat. Nos. 8,293,235, 8,697,074, WO 2009/155723 A2 and WO 2006/131013 A2.

Currently approved anti-TNFα antibodies include (i) infliximab, a chimeric IgG anti-human monoclonal antibody (Remicade®); (ii) etanercept, a TNFR2 dimeric fusion protein, with an IgG1 Fc (Enbrel®); (iii) adalimumab, a fully human monoclonal antibody (mAb) (Humira®), (iv) certolizumab, a PEGylated Fab fragment (Cimzia®) and (v) golimumab, a human IgGIK monoclonal antibody (Simponi®). Moreover, various biosimilars are in development. Therefore, in one embodiment of the present invention, the antibody or functional fragment thereof is selected from infliximab, adalimumab, etanercept, certolizumab pegol and golimumab or functional fragments thereof. In another embodiment of the present invention, the antibody or functional fragment thereof is an anti-TNFα antibody or functional fragment thereof as disclosed in PCT applications PCT/EP2017/056218, PCT/EP2017/056246, PCT/EP2017/056237 and PCT/EP2017/056227 as originally filed. In yet another embodiment of the present invention, the at least one antibody or functional fragment thereof is an anti-TNFα antibody or functional fragment thereof with a light chain variable domain and/or a heavy chain variable domain comprising complementarity-determining regions (CDRs) with amino acid sequences as disclosed in PCT applications PCT/EP2017/056218, PCT/EP2017/056246, PCT/EP2017/056237 and PCT/EP2017/056227, as originally filed.

In a preferred embodiment of the present invention, the at least one antibody or functional fragment thereof is an anti-TNFα antibody or functional fragment thereof with a light chain variable domain and/or a heavy chain variable domain comprising one or more CDRs with amino acid sequences as disclosed in SEQ ID NO:7, 9, 12, 14, 24 and 25 of PCT/EP2017/056218, in SEQ ID NO:7-11 and 6 of PCT/EP2017/056246, in SEQ ID NO:7-12 of PCT/EP2017/056237, in SEQ ID NO:1-4, 7 and 6 of PCT/EP2017/056227, and combinations thereof. In another preferred embodiment of the present invention, the at least one antibody or functional fragment thereof is an anti-TNFα antibody or functional fragment thereof with a light chain variable domain and a heavy chain variable domain comprising CDRs with amino acid sequences as disclosed in claim 2 of PCT/EP2017/056218, in claim 2 of PCT/EP2017/056246, in claim 2 of PCT/EP2017/056237 and/or in claim 2 PCT/EP2017/056227, as originally filed. In yet another preferred embodiment of the present invention, the at least one anti-TNFα antibody or functional fragment thereof is selected from the group consisting of anti-TNFα antibodies or functional fragments thereof comprising a heavy chain variable domain amino acid sequence and/or a light chain variable domain amino acid sequence according to claim 4 of PCT/EP2017/056218, claims 5 and 6 of PCT/EP2017/056246, claims 5 and 6 of PCT/EP2017/056237, claim 4 of PCT/EP2017/056227, and combinations thereof.

The drug coating comprises a buffer. The nature of the buffer is not particularly limited and includes all buffers that ensure stability and activity of antibodies and functional fragments thereof in solution. In one embodiment of the present invention, the buffer is selected from the group consisting of acetate buffer; citrate buffer; histidine buffer; succinate buffer; phosphate buffer; hydroxymethylaminomethane (TRIS) buffer; and combinations thereof.

The polymeric binder used in the inventive method for the preparation of the solid dosage form is not particularly limited. Examples of polymeric binder suitable for the present invention include hydroxypropyl methylcellulose (HPMC); hydroxypropyl cellulose (HPC), methylcellulose (MC); polyvinylpyrrolidone (PVP); macrogol poly(vinylalcohol) grafted copolymer (eg. Kollidon® IR); poly(ethyl acrylate, methyl methacrylate) 2:1 (e.g. Eudragit® NM 30D or Eudragit® NE 30D); poly(ethyl acrylate, methyl methacrylate, trimethylammonioethyl methacrylate chloride) 1:2:0.1 (e.g. Eudragit® RS 30D); poly(ethyl acrylate, methyl methacrylate, trimethylammonioethyl methacrylate chloride) 1:2:0.2 (e.g. Eudragit® RL 30D); ethylcellulose (e.g. Surelease® or Aquacoat® ECD); polyvinyl acetate (eg. Kollicoat® SR 30D); and combinations thereof. The polymeric binder may be provided in any form that allows dissolving or dispersing the polymeric binder in the aqueous solution or suspension. In a preferred embodiment of the present invention, the polymeric binder is provided as an aqueous solution or dispersion (suspension).

In one embodiment of the present invention, the polymeric binder in the drug coating is suitable for an immediate release drug coating. Thus, the drug coating of the solid dosage form prepared by the method of the present invention using the polymeric binders suitable for an immediate release coating gives rise to an immediate release of the at least one antibody or functional fragment thereof from the dosage form. As used herein, the term "immediate release" is meant to describe a drug coating in which more than 60%, preferably more than 70%, more preferably more than 80%, even more preferably more than 90%, most preferably 95%, of the antibody or functional fragment thereof is released from the drug coating after 2 h, preferably after 1 h, even more preferably after 0.5 h, of exposure to an aqueous environment.

The term an "aqueous environment" as used in the context of the present invention may refer to a solution or suspension of which a large part is water. This includes intestinal fluid.

To measure the amount of antibody or functional fragment released from a drug coating as the outermost coating of a solid dosage form into an aqueous solution, the drug layer deposited on an inert core can be immersed in a defined volume of aqueous solution (preferably buffered) for a defined period of the time under continuous agitation of the aqueous solution and the resulting concentration of the at least one antibody or functional fragment thereof in the aqueous solution can be determined and compared to the initial amount applied during the layering process, considering the process efficiency and weight gain. The term an "aqueous solution" as used herein may refer to solution or suspension of which a large part is water (e.g. more than 30 wt.-%, preferably more than 40 wt.-%, preferably more than 50 wt.-%, preferably more than 60 wt.-%, most preferably more than 70 wt.-% of water). For dissolution testing the aqueous solution may preferably comprise a buffer. Similarly, the release from a solid dosage form with additional coatings deposited onto the drug coating, e.g. a sustained release coating or a delayed release coating, can be determined. Means to determine an antibody concentration in an aqueous solution are known in the art and include for example measuring the absorbance at 280 nm or using a colorimetric, reagent-based protein assay like the Bradford assay or by ELISA.

It is to be understood that throughout the present disclosure, whenever referring to dissolution of, or recovery of antibodies or functional fragments thereof from, a solid dosage form/multiparticulate drug delivery system (as in the section just above and below), e.g. by continuously immersing a solid dosage form/multiparticulate drug delivery system in an aqueous (buffer) solution under continuous (constant) agitation, for example the following standard testing setup, or a related standard testing setup known to the person skilled in the art, can be used: The release of the at least one antibody or functional fragment thereof can be evaluated using a standard dissolution apparatus I (baskets), II (paddle), III (reciprocating cylinder) or apparatus IV (flow through cell), where the buffer (i.e. aqueous buffer solution) is equilibrated at 37° C. The buffer volume used for dissolution testing can be adapted for instance using mini-vessels in the apparatus I or II to allow reduction of volume required and to be more bio-relevant. Release of antibodies or functional fragments thereof during dissolution can be quantified offline by an ELISA method.

In one embodiment of the present invention, the drug coating is an immediate release drug coating, allowing the recovery of at least 70%, preferably at least 80%, more preferably at least 90%, even more preferably at least 95%, even more preferably at least 97%, even more preferably at least 99%, of the at least one antibody or functional fragment thereof from the drug coating within 1 h of continuously immersing a solid dosage form, with the drug coating as the outermost coating, in an aqueous solution (e.g. at a temperature of 25° C. or higher (e.g. 25-40° C., preferably about 37° C.)) under continuous agitation of the aqueous solution.

Polymeric binders suitable for an immediate release coating comprise hydroxypropyl methylcellulose (HPMC); Hydroxypropyl cellulose (HPC), methylcellulose (MC); polyvinylpyrrolidone (PVP); macrogol poly(vinylalcohol) grafted copolymer (eg. Kollidon® IR). Preferably, the polymeric binder suitable for the immediate release coating is selected from HPMC, MC, and combinations thereof, preferably HPMC.

In another embodiment of the present invention, the polymeric binder in the drug coating comprises at least one sustained release polymeric binder. The at least one sustained release polymeric binder is not particularly limited as long as it ensures a sustained release from the drug coating, and as long as it does not affect stability, activity and solubility of the at least one antibody or functional fragment thereof. The term "sustained release" is known in the art. As used herein, the term "sustained release" may be used to describe a release of the active agent from a drug coating or a solid dosage form, such that a substantial fraction of antibody or functional fragment thereof is release from the drug coating or the solid dosage form upon exposure to a aqueous environment over a prolonged period of time, e.g. over at least 6 h, preferably at least 10 h, more preferably at least 14 h, even more preferably at least 18 h, most preferably at least 24 h.

In one embodiment of the present invention, the polymeric binder in the drug coating comprises at least one sustained release polymeric binder, allowing the recovery of at least 40%, preferably at least 50%, more preferably at least 60%, even more preferably at least 70%, even more preferably at least 80%, even more preferably at least 85%, even more preferably at least 90%, even more preferably at least 93%, most preferably at least 95%, of the at least one antibody or functional fragment thereof from the drug coating within a defined time period (e.g. 4 h, or 6 h, or 8 h, or 10 h, or 12 h, or 14 h, or 16 h, or 18 h, or 20 h, or 22 h, or 24 h, or 26 h, or 28 h, or 30 h, or 32 h, etc.) of continuously immersing the solid dosage form in an aqueous solution (e.g. at a temperature of 25° C. or higher (e.g. 25-40° C., preferably about 37° C.)) under continuous agitation. In a preferred embodiment of the present invention, the polymeric binder in the drug coating comprises at least one sustained release polymeric binder, allowing a sustained release of the at least one antibody or functional fragment thereof over a time period of at least 5 h, preferably at least 10 h, more preferably at least 15 h, even more preferably at least 20 h, most preferably at least 24 h, etc., upon continuously immersing the solid dosage form in an aqueous solution under continuous agitation of the aqueous solution. In an alternatively preferred embodiment of the present invention, the polymeric binder in the drug coating comprises at least one sustained release polymeric binder, allowing a sustained release of the at least one antibody or functional fragment thereof over a time period of at least 8 h, at least 10 h, at least 12 h, at least 14 h, or at least 16 h upon continuously immersing the solid dosage form in an aqueous solution under continuous agitation.

In particular for conditions that affect a section of the gastrointestinal tract, including the ileum and large intestine, such as Crohn's Disease and ulcerative colitis, a sustained release solid dosage form of an active biological agent in the form of an antibody or functional fragment thereof, exhibiting limited systemic absorption can be desirable.

For a sustained release coating, at least one sustained release polymeric binder may be used as a polymeric binder. However more than one, e.g. two, three or four, sustained release polymeric binder can be used as polymeric binder of the active agent coating liquid.

Sustained release polymeric binder suitable for the present invention comprise poly(ethyl acrylate, methyl methacrylate) 2:1 (e.g. Eudragit® NM 30D or Eudragit® NM 30D); poly(ethyl acrylate, methyl methacrylate, trimethyl-ammonioethyl methacrylate chloride) 1:2:0.1 (e.g. Eudragit® RS 30D); poly(ethyl acrylate, methyl methacrylate, trimethylammonioethyl methacrylate chloride) 1:2:0.2

(e.g. Eudragit® RL 30D); ethylcellulose (e.g. Surelease® or Aquacoat® ECD), polyvinyl acetate (eg. Kollicoat® SR 30D); and combinations thereof. In one embodiment of the present invention the at least one sustained release polymeric binder is selected from the group consisting of poly (ethyl acrylate, methyl methacrylate) 2:1 (e.g. Eudragit® NM 30D or Eudragit® NE 30D); poly(ethyl acrylate, methyl methacrylate, trimethylammonioethyl methacrylate chloride) 1:2:0.1 (e.g. Eudragit® RS 30D); poly(ethyl acrylate, methyl methacrylate, trimethylammonioethyl methacrylate chloride) 1:2:0.2 (e.g. Eudragit® RL 30D); ethylcellulose (e.g. Surelease® or Aquacoat® ECD), polyvinyl acetate (eg. Kollicoat® SR 30D); and combinations thereof.

The inventive method, in its most general form, comprises as first step, step a), preparing an active agent coating liquid, comprising the at least one antibody or functional fragment thereof, the buffer and the at least one polymeric binder, as an aqueous solution or suspension. The individual components of the active agent coating liquid, i.e. at least one antibody or functional fragment thereof, the buffer and the at least one polymeric binder, as defined above, may be provided in any form that allows bringing them into aqueous solution or suspension. For example the individual component may be provided as powders, granules or suspended or dissolved in a solvent, and can then be dissolved or dispersed in the aqueous solution or suspension.

The term "aqueous solution or suspension" as used herein refers to a solution or suspension, wherein at least 60%, preferably at least 70%, more preferably at least 80%, even more preferably at least 90%, even more preferably at least 95%, 97%, 98%, 99%, or 99.5%, even more preferably at least 99.9%, most preferably 100%, of the solvent used is water. In one embodiment of the present invention, the active agent coating liquid is an aqueous solution or suspension wherein 100% of the solvent used is water.

The manner in which the at least one antibody or functional fragment thereof is introduced into the active agent coating liquid is not particularly limited. For example, the antibody or functional fragment thereof can be added as a powder comprising particles containing antibodies or functional fragments thereof, e.g. as a lyophilized, spray dried, air dried or vacuum dried powder, and thereby directly reconstitute the antibody or functional fragment thereof in the active agent coating liquid. The term "powder" as used in this context is to be understood in its broadest meaning, including fine particles as well as larger particles and granules. Alternatively, the antibody or functional fragment thereof can be added already in solution, e.g. as part of a buffered aqueous solution.

In one embodiment of the present invention the at least one antibody or functional fragment thereof is provided as a powder which is added to the active agent coating liquid. It has been found that by adding the at least one antibody or functional fragment thereof as a powder to the active agent coating liquid, a higher concentration of the at least one antibody or functional fragment thereof in the active agent coating liquid can be achieved, which ensures a high concentration of the at least one antibody or functional fragment thereof in the drug coating, thereby minimizing processing time and exposure to external stresses for the solid dosage form. In a preferred embodiment, the at least one antibody or functional fragment thereof is dissolved in the active agent coating liquid of step a).

The concentration of the antibody or functional fragment thereof in the active agent coating liquid is not particularly limited as at long as a target loading of the at least one antibody or functional fragment thereof on the solid dosage form can be reached, and as long as stability, activity and minimal irreversible interactions with other components of the active agent coating liquid are ensured for the at least one antibody or functional fragment thereof. In one embodiment of the present invention, the active agent coating liquid comprises 0.01-100 mg/ml, preferably 0.1-50 mg/ml, more preferably 0.5-50 mg/ml, even more preferably 1-50 mg/ml, even more preferably 1-30 mg/ml, even more preferably 1-25 mg/ml, even more preferably 5-25 mg/ml, most preferably about 25 mg/ml, alternatively most preferably about 15 mg/ml, of the at least one antibody or functional fragment thereof. In another embodiment of the present invention, the active agent coating liquid comprises 0.001-15 wt.-%, preferably 0.001-10 wt.-%, more preferably 0.01-7 wt.-%, even more preferably 0.05-5 wt.-%, even more preferably 0.1-3.5 wt.-%, even more preferably about 0.5-2.5 wt.-%, most preferably about 1.4 wt.-%, alternatively most preferably about 4.7 wt.-%, of the at least one antibody or functional fragment thereof. In an alternative embodiment of the present invention, the active agent coating liquid comprises 5-300 wt.-%, preferably 20-200 wt.-%, more preferably 50-150 wt.-%, even more preferably 50-115 wt.-%, even more preferably 85-115 wt.-%, most preferably about 90-105 wt.-%, alternatively most preferably about 45-60 wt.-%, of the at least one antibody or functional fragment thereof, relative to the total weight of the polymeric binder solids in the active agent coating liquid.

In an alternative embodiment of the present invention, the concentration of the antibody in the active agent coating liquid is such as to result in an amount of antibody or functional fragment thereof in the solid dosage form prepared by the method of the present invention that allows the administration of a therapeutically effective dose of the at least one antibody or functional fragment thereof as a single unit dose, for example in the form of a tablet or capsule comprising multiple solid dosage forms (e.g. in the form of multiple pellets, beads or granules). The term "administration" relates to the manner and form in which the composition comes into first contact with the body of a patient. The solid dosage form prepared by the inventive method can be administered orally or in any other way that results in the accumulation of the solid dosage form at the intended site of local application and/or absorption into body tissue. Preferably the solid dosage form of the present invention is intended for oral administration. A "therapeutically effective dose" is the amount of the at least one antibody or functional fragment thereof required to provide the desired therapeutic effect. The exact amount may vary for different antibodies or functional fragments thereof and/or for individual patients, but can be determined by one skilled in the art.

The active agent coating liquid comprises a buffer. The nature of the buffer is not particularly limited and includes all buffers that ensure stability and activity of antibodies and functional fragments thereof in solution. In one embodiment of the present invention, the buffer is selected from the group consisting of acetate buffer; citrate buffer; histidine buffer; succinate buffer; phosphate buffer; hydroxymethylaminomethane (TRIS) buffer; and combinations thereof; preferably a buffer at a certain pH where a given antibody is stable. The buffer may be present in the active agent coating suspension in any amount that ensures stability and activity of antibodies and functional fragments thereof in solution. In one embodiment of the present invention, the buffer is present in the active agent coating suspension comprises 0.01-20 wt.-%, preferably 0.1-10 wt.-%, more preferably 0.5-5 wt.-%, even more preferably 1-5 wt.-%, most preferably about 4.5 wt.-%, alternatively most preferably about 15 wt.-%, buffer.

The polymeric binder as defined above may be used in any form that allows dissolution or dispersion in the active agent coating liquid. In one embodiment of the present invention, the polymeric binder is added to the aqueous solution or suspension as solids e.g. in the form of a powder or granules. In another embodiment, the polymeric binder is already in solution or suspension, preferably as part of an aqueous solution or suspension, and is added as such to the active agent coating liquid. If the polymeric binder is suitable for immediate release, the polymeric binder will have a high solubility in an aqueous environment. Consequently, the polymeric binder in a form suitable for dissolution or dispersion will be easily dissolved or dispersed in the active agent coating liquid. If the polymeric binder comprises at least one sustained release polymeric binder, the at least one sustained release polymeric binder may be used in any form that allows dissolution or dispersion in the active agent coating liquid. According to a preferred embodiment, the at least one sustained release polymeric binder is added to the active agent coating liquid in the form of an aqueous suspension (aqueous dispersion).

The amount of polymeric binder in the active agent coating liquid is not particularly limited as long as the active agent coating liquid can be used for processing by spray coating, and at the same time for the at least one antibody or functional fragment thereof stability, activity and minimal irreversible interaction with other components of the active agent coating liquid are ensured. In one embodiment of the present invention, the active agent coating liquid comprises a concentration of polymeric binder that maximizes processing speed (i.e. spray rate), while minimizing clogging of the tubing and the spray nozzle. In another embodiment of the present invention, the active agent coating liquid comprises 0.1-20 wt.-%, preferably 0.5-10 wt.-%, more preferably 0.5-5 wt.-%, even more preferably 1-5 wt.-%, even more preferably 1-3 wt.-%, most preferably about 2.5 wt.-% (preferred embodiment where the drug coating is an immediate release drug coating), alternatively most preferably about 7-7.5 wt.-% (preferred embodiment where the drug coating is a sustained release drug coating) polymeric binder.

According to one embodiment of the present invention, the active agent coating liquid in step a) comprises at least one anti-tacking agent. An anti-tacking agent can improve the handling of the active agent coating solution. An anti-tacking agent may be particularly beneficial for polymeric binders like hydroxypropyl methylcellulose (HPMC); hydroxypropyl cellulose (HPC), methylcellulose (MC); polyvinylpyrrolidone (PVP); macrogol poly(vinylalcohol) grafted copolymer (eg. Kollidon® IR), poly(ethyl acrylate, methyl methacrylate) 2:1 (e.g. Eudragit® NM 30D or Eudragit® NE 30D); poly(ethyl acrylate, methyl methacrylate, trimethylammonioethyl methacrylate chloride) 1:2:0.1 (e.g. Eudragit® RS 30D); poly(ethyl acrylate, methyl methacrylate, trimethylammonioethyl methacrylate chloride) 1:2:0.2 (e.g. Eudragit® RL 30D); ethylcellulose (e.g. Surelease® or Aquacoat® ECD), polyvinyl acetate (e.g. Kollicoat® SR 30D). The anti-tacking agent to be used in the active agent coating liquid is not particularly limited. In one embodiment of the present invention, the anti-tacking agent is selected from colloidal silica dioxide, mesoporous silica, glycerolmonostearate (GMS), stearic acid, magnesium stearate and talc, preferably mesoporous silica or GMS, more preferably mesoporous silica. The amount of anti-tacking agent to be used in the active agent coating liquid is not particularly limited. In one embodiment of the present invention, the active agent coating liquid comprises 0.1-50 wt.-%, preferably 1-30 wt.-%, more preferably 10-20 wt.-% or 5-50 wt.-%, anti-tacking agent, relative to the total weight of the polymeric binder solids in the active agent coating liquid.

In another embodiment of the present invention the active agent coating liquid comprises i) 0.001-10 wt.-%, preferably 0.01-7 wt.-%, more preferably 0.05-5 wt.-%, even more preferably 0.1-3.5 wt.-%, even more preferably 0.5-2.5 wt.-%, most preferably about 1.4 wt.-%, alternatively most preferably about 4.7 wt.-%, of the at least one antibody or functional fragment thereof; ii) 0.1-20 wt.-%, preferably 0.5-10 wt.-%, more preferably 1-5 wt.-%, even more preferably 1-3 wt.-%, even more preferably 2-3 wt.-%, most preferably about 2.5 wt.-% (preferred embodiment where the drug coating is an immediate release drug coating), alternatively most preferably about 7-7.5 wt.-% (preferred embodiment where the drug coating is a sustained release drug coating), polymeric binder; and iii) 0-5 wt.-%, preferably 0.01-3 wt.-%, more preferably 0.1-2 wt.-%, even more preferably 0.1-1 wt.-%, even more preferably 0.2-0.6 wt.-%, most preferably about 0.25 wt.-%, anti-tacking agent. In a further embodiment, the active agent coating liquid comprises i) 0.5-5 wt.-% antibody or functional fragment thereof; ii) 1-5 wt.-% polymeric binder; and iii) 0-1.25 wt.-% anti-tacking agent.

In a preferred embodiment, the active agent coating liquid comprises i) 0.5-2.5 wt.-% antibody or functional fragment thereof; ii) 1-3 wt.-% polymeric binder; and iii) 0.2-0.6 wt.-% anti-tacking agent. In an alternatively preferred embodiment, the active agent coating liquid comprises i) about 2.5 wt.-% antibody or functional fragment thereof; ii) about 2.5 wt.-% polymeric binder; and iii) about 0.25 wt.-% anti-tacking agent. In another alternatively preferred embodiment, the active agent coating liquid comprises i) about 1.5 wt.-% antibody or functional fragment thereof; ii) about 2.5 wt.-% polymeric binder; and iii) about 0.25 wt.-% anti-tacking agent. The embodiments in this paragraph are particularly preferable, if the at least one polymeric binder is suitable for immediate release.

In an alternative embodiment the active agent coating liquid comprises i) 0.01-5 wt.-% antibody or functional fragment thereof; ii) 0.5-20 wt.-% polymeric binder; and iii) 0-5 wt.-% anti-tacking agent. In another alternative embodiment the active agent coating liquid comprises i) 0.1-2 wt.-% antibody or functional fragment thereof; ii) 2-15 wt.-% polymeric binder; and iii) 0-1 wt.-% anti-tacking agent. The embodiments in this paragraph are particularly preferable, if the at least one polymeric binder comprises at least one sustained release polymeric binder.

It has been found by the present inventors that by using a polymeric binder comprising at least one sustained release polymeric binder in the drug coating, the release of the at least one antibody or functional fragment thereof from the drug coating in an aqueous environment can be modified to give rise to a sustained release profile. By adjusting the ratio of the at least one sustained release polymeric binder to the at least one antibody or functional fragment thereof (w/w) in the active agent coating liquid, the release rate of the at least one antibody or functional fragment thereof can be modified, such that a higher ratio results in a slower release rate. Thereby the release rate of the at least one antibody or functional fragment thereof from the drug coating can be adapted to individual requirements of the antibody or functional fragment thereof used, the site of release and the condition to be treated by the solid dosage form. Therefore, in one embodiment of the present invention, the at least one sustained release polymeric binder (S) and the at least one antibody or functional fragment thereof (A) are present in the active agent coating liquid in a ratio S/A (w/w) of 0.5 to 100, preferably 0.5 to 50, more preferably 1 to 30, even more preferably 5 to 30, even more preferably 10 to 30, even more preferably 15 to 25, alternatively 0.5 to 200.

According another embodiment of the present invention, the active agent coating liquid in step a) comprises at least one plasticizer. The present inventors found that a plasticizer, in particular when the polymeric binder comprises at least one sustained release polymeric binder, can considerably improve the properties of the resulting drug coating, including the integrity of the resulting drug coating and an improved sustained release profile. The plasticizer to be used in the active agent coating liquid is not particularly limited. In one embodiment of the present invention, the plasticizer is selected from the group consisting of triethyl citrate, polyethylene glycol, acetyl triethyl citrate, butyl citrate, polysorbates, 1,2-polyproppylene glycol, (TEC) and dibutyl sebacate (DBS). In a preferred embodiment of the present invention, the plasticizer is selected from the group consisting of triethyl citrate (TEC) and dibutyl sebacate (DBS). The amount of plasticizer to be used in the active agent coating liquid is not particularly limited. In one embodiment of the present invention, the active agent coating liquid comprises 5-35 wt.-%, preferably 10-30 wt.-%, more preferably about 20-25 wt.-%, plasticizer, relative to the total weight of the polymeric binder solids in the active agent coating liquid.

Moreover, it has been found by the present inventors that for solid dosage forms where a slow and constant sustained release, e.g. over a time period of 20 h or 24 h or longer, is desirable, a hydrophobic plasticizer like DBS (compared to a more hydrophilic plasticizer) gives very advantageous results, giving rise to a slow and more constant release of the at least one antibody or functional fragment thereof in the drug layer. Therefore, according to one embodiment of the present invention, where the polymeric binder comprises at least one sustained release polymeric binder, the plasticizer in the active agent coating liquid is DBS.

According to yet another embodiment of the present invention, the active agent coating liquid in step a) comprises at least one coalescence enhancer. A coalescence enhancer, in particular when the polymeric binder comprises at least one sustained release polymeric binder, may considerably improve the properties of the resulting drug coating, including the integrity of the resulting drug coating and an improved sustained release profile. The coalescence enhancer to be used in the active agent coating liquid is not particularly limited. According to one embodiment of the present invention, the coalescence enhancer to be used in the sustained release coating liquid is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, fatty alcohols such as cetyl alcohol or oleyl alcohol, sodium glycolate, sodium de(s)oxycholate, polyethylene glycol, polypropylene glycol, alkyl poly(ethylene oxide), alkyl glycoside, alkyl polyglucoside, octyl glucoside, decyl maltoside, propylene glycol monolaurate (e.g. Lauroglycol™ 90), and combinations thereof. In a preferred embodiment of the present invention, the coalescence enhancer is propylene glycol monolaurate (e.g. Lauroglycol™ 90). The amount of coalescence enhancer to be used in the active agent coating liquid is not particularly limited. In one embodiment of the present invention, the active agent coating liquid comprises 1-20 wt.-%, preferably 2-15 wt.-%, more preferably 5-10 wt.-%, coalescence enhancer, relative to the total weight of the sustained release polymeric binder solids in the active agent coating liquid.

According to one embodiment the active agent coating liquid in step a) and/or the sustained release coating liquid in step d) comprise(s) at least one surfactants. The surfactant may be present in the active agent coating liquid and/or the sustained release coating liquid in a concentration 0.005 to 2.0 wt.-%, 0.01 to 1 wt.-%, more preferably 0.05 to 0.8 wt.-%, even more preferably about 0.1 to 0.5 wt.-% surfactant. Suitable surfactants for the active agent coating liquid in step a) and/or the sustained release coating liquid in step d) are selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, cetyl alcohol, oleyl alcohol, sodium glycolate, sodium de(s)oxycholate, polyethylene glycol, polypropylene glycol, alkyl poly(ethylene oxide), alkyl glycoside, alkyl polyglucoside, octyl glucoside, decyl maltoside, and combinations thereof.

The active agent coating liquid in step a) and/or the sustained release coating liquid in step d) of the method of the present invention may optionally comprise at least one further excipient. The term "excipient," as used herein, refers to a non-therapeutic agent added to the formulation to provide a desired consistency, viscosity or stabilizing effect. According to one embodiment of the present invention the at least one further excipients is selected from pharmaceutically acceptable excipients like antioxidants, humectants, protective colloids, dyes, fillers, protease inhibitors, permeation enhancers, and combinations thereof. According to a specific embodiment of the present invention the active agent coating liquid in step a) comprises at least one fillers, the at least one filler being preferably selected from the group consisting of dextrose, mannitol, sorbitol, xylitol, trehalose, sucrose, amino acids such as arginine, histidine, glycine, alanine, lysine, proline, leucine, glutamic acid, serine, aspartic acid and asparagine, and respective salts thereof, The active agent coating liquid may comprise for example 0.01-30 wt.-%, 0.1-20 wt.-%, or 0.5-10 wt.-% of the at least one filler relative to the total solid content in the active agent coating liquid.

The individual components of step a) can be blended to give rise to the active agent coating liquid by any conventional mixing device. Such mixing devices are known in the art and include for example a paddle mixer, magnetic stirring mixer. The mixing device may be an integral part of the spray coater used for step b).

In step b) of the inventive method, the inert core unit is layered with the active agent coating liquid using spray coating. In this step for example a fluidized-bed spray coater or a pan coater can be used. According to a preferred embodiment of the present invention a fluidized-bed spray coater is used. The use of a fluidized-bed spray coater for spray coating an inert core unit is known in the art. It has been found by the present inventors that during spray coating controlling temperature and pressure to which the active agent coating liquid is exposed to, as well as processing time is critical for preserving activity and stability of the at least one antibody or functional fragment thereof. Thus, it is beneficial for the at least one antibody or functional fragment thereof in the solid dosage form prepared by the inventive method, if parameters and conditions used during spray coating are carefully controlled.

Therefore, according to one embodiment of the present invention, during the spray coating in step b) the atomising air pressure at the spray nozzle is lower than 200 kPa, preferably is lower than 100 kPa, more preferably from 10 to 100 kPa, even more preferably from 10 to 50 kPa, even more preferably from 25 to 50 kPa. In another embodiment of the present invention, the spray coater is set to a temperature lower than the melting temperature (Tm) of the least one antibody or functional fragment thereof. The above is understood to mean that in case more than one antibody or functional fragment are included the active agent coating liquid, the temperature is to be lower than the melting temperature (Tm) of the antibody or functional fragment thereof with the lowest Tm. In yet another embodiment of the present invention, the spray coater is set to a temperature lower than 65° C., preferably from 25° C. to 60° C., more preferably from 35° C. to 55° C., even more preferably from 40° C. to 50° C., even more preferably from 42° C. to 50° C. In yet another embodiment of the present invention, a fluidized-bed spray coater is used and in the fluidized-bed spray coater the inlet air temperature is lower than 65° C., preferably from 25° C. to 60° C., more preferably from 35° C. to 55° C., even more preferably from 40° C. to 50° C., even more preferably from 42° C. to 50° C. The "the inlet air temperature" or "inlet temperature" is temperature of the air, which is used to fluidize the bed. Consequently, the inlet air temperature together with the spraying rate determines the temperature in the spraying chamber and thus the temperature to which the antibody or functional fragment thereof in the coating liquid is exposed during spray coating.

The fluidized-bed spray coater to be used for the present invention is not particularly limited. Fluidized-bed spray coater are known in the art and include for example fluidized-bed equipment developed and commercialized by GEA Group, Glatt GmbH, Freund-Vector Corporation and Inora Pharmaceutical Machinery Co. In one embodiment of the present invention the active agent coating liquid is sprayed onto the inert core unit using a bottom-spray fluidized-bed spray coater. In another embodiment of the present invention, the active agent coating liquid is sprayed onto the inert core unit using a top-spray fluidized-bed spray coater. Additional parameters in the context of a top-spray fluidized-bed spray coater, which are may be adjusted to the benefit of the inventive method include a container agitation frequency; nozzle position; pump flow rate; spraying rate; and inlet air velocity.

According to step c) of the method of the present invention, the wet drug layered inert core unit is dried, either simultaneously with step b), or after step b) has been completed, to give rise to the dried solid dosage form. The term "wet drug layered inert core unit" refers to the inert core unit, which has been layered with the active agent coating liquid using spray coating, but which retains sufficient solvent from the active agent coating liquid that the applied drug coating is still wet. During drying the solvent on the wet drug layered inert core unit is removed. Means to dry wet drug layered inert core unit are known in the art, and include for example a fluidized bed, a drying cabinet or an oven.

The term "dried" or "dry" when referring to a solid dosage form (e.g. as in "dried solid dosage form") means a solid dosage form containing preferably less than 10%, more preferably less than 7%, even more preferably less than 5%, even more preferably less than 3%, even more preferably less than 2% and most preferably less than 1.5% residual solvent content. Residual solvent can be determined by measuring the moisture of the solid dosage form. Thus, preferably the inventive solid dosage form after step c), or after step d) if an additional coating in the form of a sustained release coating is applied after step c), contains less than 10% moisture, preferably less than 7% moisture, more preferably less than 5% moisture, even more preferably less than 3% moisture, even more preferably less than and most preferably less than 1.5% moisture. One method for determining the moisture of any given solid dosage form is the Loss on Drying (LOD) technique. For example the amount of moisture contained in solid dosage form can be gravimetrically measured using LOD at 105° C. for 1 hour.

The activity and stability of antibodies and functional fragments thereof as used for the present invention are very sensitive to external stress like temperature fluctuations and particularly to elevated temperatures. Therefore, in accordance with the method of the present invention the temperature during drying is such as to protect the activity and stability of the antibodies and functional fragments thereof and at the same time allow efficient drying of the wet drug layered inert core unit.

According to one embodiment of the present invention, the wet drug layered inert core unit is dried simultaneously with step b). The wet drug layered inert core unit can be dried simultaneously with step b) using the inlet air flow of the fluidized bed. According to the present invention, simultaneous drying of the wet drug layered inert core unit is particularly suitable for immediate release drug coatings, i.e. drug coatings wherein the at least one polymeric binder is suitable for immediate release as defined above. Simultaneous drying of the wet drug layered inert core units has the advantage of reducing processing time by combining spray coating and drying of the inert core unit in one step. According to one embodiment of the present invention, where, preferably a fluidized-bed spray coater is used and, the wet drug layered inert core units are dried simultaneously with step b), the inlet air has a temperature of up to 65° C., preferably up to 60° C., more preferably up to 55° C., more preferably 40 to 50° C.

According to another embodiment of the present invention, the wet drug layered inert core unit is dried after step b) has been completed. It has been found by the present inventors that for drug coatings comprising at least one sustained release polymeric binder, which are intended for sustained release in an aqueous environment, drying the wet drug layered inert core unit after step b) has been completed improves the sustained release profile of the resulting drug coating due to polymeric coating curing. Therefore according a preferred embodiment of the present invention, the wet drug layered inert core unit, which is dried after step b) has been completed, comprises at least one sustained release polymeric binder.

Moreover, the present inventors surprisingly found that if the polymeric binder in the drug coating comprises at least one sustained release polymeric binder, drying the wet drug layered inert core after step b) in a fluidized-bed equipment or an oven set at a given temperature drastically improves the dissolution behavior of the resulting drug coating, giving rise to an improved sustained release profile of the at least one antibody or functional fragment thereof from the drug coating in an aqueous environment. The term "oven" as used herein is to be understood in its broadest meaning, i.e. a chamber used for heating and drying, and also includes for example the term "drying cabinet". Suitable ovens or drying cabinets for the purpose of the inventive method are known in the art. Suitable fluidized bed equipment for the purpose of the inventive method is known in the art, and includes for example large-scale fluidized-bed equipment. The temperature at which the wet drug layered inert core unit is dried, if dried after step b) has been completed is not particularly limited as long as it preserves stability and activity of the at least one antibody or functional fragment thereof comprised in the drug coating. A temperature of not higher than 65° C., during drying after step b) has been completed, has been found to allow the wet drug layered inert core unit, comprising at least one sustained release polymeric binder, to be dried sufficiently to give rise to an optimal sustained release profile, while preserving stability and activity of the at least one antibody or functional fragment thereof in the drug coating. Therefore, according to one embodiment of the present invention, the temperature is not higher than 65° C., preferably not higher than 60° C., more preferably not higher than 55° C., during the drying of the wet drug layered inert core unit, comprising at least one sustained release polymeric binder. In another embodiment of the present invention, during the drying of the wet drug layered inert core unit, comprising at least one sustained release polymeric binder, the temperature is lower than the melting temperature (Tm) of the least one antibody or functional fragment thereof. The above is understood to mean that in case more than one antibody or functional fragment are included the wet drug layered inert core unit, the temperature is to be lower than the melting temperature (Tm) of the antibody or functional fragment thereof with the lowest Tm. The wet drug layered inert core unit may be dried until a dry solid dosage form is obtained. The solid dosage form is dry, when a large proportion of the solvent used in the active agent coating liquid has been removed by evaporation. In one embodiment of the present invention the solid dosage form is understood to be dry, when the residual solvent content of the solid dosage form is preferably less than 15%, more preferably less than 10% even more preferably less than 7%, even more preferably less than 5%, most preferably less than 3%, 2%, 1% or 0.5%, relative to the total weight of the solid dosage form. According to a preferred embodiment of the present invention, the wet drug layered inert core unit, comprising at least one sustained release polymeric binder, is dried for up to 30 h, more preferably for about 30 min to 24 h. The drying may further be assisted by vacuum.

According to one embodiment, the inventive method further comprises, after step c), the step of d) applying at least one additional coating in the form of a sustained release coating, by layering the solid dosage form of step c) with a sustained release coating liquid using spray coating, preferably fluidized-bed spray coating, and then drying the wet layered solid dosage form using an oven or a fluidized-bed equipment.

The at least one sustained release polymer to be used in step d) is not particularly limited as long as it ensures a sustained release of the at least one antibody or functional fragment thereof from the solid dosage form. For the sustained release coating, at least one sustained release polymer may be used as a polymer. However more than one, e.g. two, three or four, sustained release polymers can be used as polymers of the sustained release coating liquid.

Sustained release polymers suitable for the sustained release coating of step d) of the present invention comprise poly(ethyl acrylate, methyl methacrylate) 2:1 (e.g. Eudragit® NM 30D, Eudragit® NE 30D); poly(ethyl acrylate, methyl methacrylate, trimethylammonioethyl methacrylate chloride) 1:2:0.1 (e.g. Eudragit® RS 30D); poly (ethyl acrylate, methyl methacrylate, trimethylammonioethyl methacrylate chloride) 1:2:0.2 (e.g. Eudragit® RL 30D); ethylcellulose (e.g. Surelease® or Aquacoat® ECD), polyvinyl acetate (eg. Kollicoat® SR 30D). In one embodiment of the present invention the at least one sustained release polymer is selected from the group consisting of poly(ethyl acrylate, methyl methacrylate) 2:1 (e.g. Eudragit® NM 30D, Eudragit® NE 30D); poly(ethyl acrylate, methyl methacrylate, trimethylammonioethyl methacrylate chloride) 1:2:0.1 (e.g. Eudragit® RS 30D); poly(ethyl acrylate, methyl methacrylate, trimethylammonioethyl methacrylate chloride) 1:2:0.2 (e.g. Eudragit® RL 30D); ethylcellulose (e.g. Surelease® or Aquacoat® ECD), polyvinyl acetate (e.g. Kollicoat® SR 30D); and combinations thereof. In a preferred embodiment of the present invention the sustained release polymers is provided in the form of an aqueous dispersion.

The concentration of sustained release polymer in the sustained release coating liquid of step d) is not particularly limited as long as it allows application of the sustained release coating liquid to the drug layered inert core unit using spray coating; and as long as the resulting sustained release coating gives rise to a sustained release profile for the at least one antibody or functional fragment thereof in the drug coating upon exposure of the solid dosage form, comprising the sustained release coating deposited over the drug coating, to an aqueous environment. In one embodiment of the present invention, the sustained release coating liquid comprises a concentration of polymer that maximizes processing speed (i.e. spray rate), while minimizing clogging of the tubing and the spray nozzle. In a preferred embodiment of the present invention the sustained release coating liquid comprises 0.1-20 wt.-%, preferably 1-15 wt.-%, more preferably 2-10 wt.-%, even more preferably 5-10 wt.-%, even more preferably 6-9 wt.-%, e.g. about 7-9 wt.-%, about 6-8.5 wt.-%, 6.5-8 wt.-%, about 7-7.5 wt.-%, or about 8 wt.-%, sustained release polymer, relative to the total weight of the sustained release coating liquid.

The amount of sustained release coating deposited on the drug coated inert core unit has been found to affect the sustained release profile, such that a higher amount of sustained release coating slows down the release of the at least one antibody or functional fragment thereof from the solid dosage form in an aqueous environment. According to one embodiment of the present invention, the solid dosage form after step d) comprises a polymer weight gain of 1-35 wt.-%, preferably 2.5-25 wt.-%, e.g. 4.5-25 wt.-%, 5-20 wt.-%, or 10-20 wt.-%, relative to the solid dosage form before step d).

The sustained release coating liquid is applied to the dried solid dosage form of step c) (i.e. the drug coated inert core unit) using spray coating, preferably fluidized-bed spray coating. With regard to the general parameters for spray coating in general and fluidized-bed spray coating in particular it is referred to the parameters and settings described above for step b) of the inventive method. In one embodiment of the present invention during step d), using a fluidized-bed coater, in the fluidized-bed coater the inlet air temperature is not higher than 65° C., preferably 35-60° C., more preferably 45-55° C. and/or the atomizing pressure at the nozzle is 10-100 kPa, preferably 10-100 kPa, more preferably 25-100 kPa.

The temperature at which the wet layered solid dosage form is dried in the oven or in the fluidized-bed, is not particularly limited as long as stability and activity of the at least one antibody or functional fragment thereof comprised in the drug coating are preserved and the temperature ensures sufficient that the resulting dosage form is dry. A temperature of not higher than 65° C., preferably of about 40-60° C., has been found to allow the wet layered solid dosage form, comprising the at least one sustained release polymer, to be dried sufficiently to give rise to an optimal sustained release profile, while preserving stability and activity of the at least one antibody or functional fragment thereof in the drug coating. Therefore, according to one embodiment of the present invention, the temperature of the oven or the fluidized-bed is not higher than 65° C., preferably about 40-60° C., during the drying of the wet layered solid dosage form of step d), comprising at least one sustained release polymer.

The wet layered solid dosage form may be dried until a dry solid dosage form comprising the drug coating and over the drug layer a sustained release coating, is obtained. The sustained release coating of the solid dosage form is dry, when a large proportion of the solvent used in the sustained release coating liquid applied to the dried solid dosage form of step c) has been removed by evaporation. In one embodiment of the present invention the sustained release coating of step d) is understood to be dry, when the residual solvent content of the solid dosage form is preferably less than 15%, more preferably less than 10% even more preferably less than 7%, even more preferably less than 5%, most preferably less than 3%, 2%, 1% or 0.5%, relative to the total weight of the solid dosage form.

According to one embodiment of the present invention, the sustained release coating liquid further comprises an anti-tacking agent. The anti-tacking agent is preferably one selected from the group listed above for the active agent coating liquid, and is preferably present in the sustained release coating liquid in an amount of 0.5-50 wt.-%, preferably 1-30 wt.-%, more preferably 5-20 wt.-%, even more preferably about 10 wt.-%, relative to the total amount of polymer solids. In particular if the sustained release polymer is poly(ethyl acrylate, methyl methacrylate, trimethylammonioethyl methacrylate chloride) 1:2:0.1 (e.g. Eudragit® RS 30D), poly(ethyl acrylate, methyl methacrylate, trimethyl-ammonioethyl methacrylate chloride) 1:2:0.2 (e.g. Eudragit® RL 30D), a combination thereof, and the like, an anti-tacking agent, e.g. in an amount of 10 wt.-% relative to the total amount of polymer solids in the coating liquid, can minimize agglomeration.

According another embodiment of the present invention, the sustained release coating liquid in step d) comprises at least one plasticizer. The use of plasticizer, can considerably improve the properties of the resulting sustained release coating, including the integrity of the resulting sustained release coating and the sustained release profile. The type of plasticizer included in the sustained release coating liquid, can affect the sustained release profile in an aqueous environment.

The plasticizer to be used in the sustained release coating liquid is not particularly limited. In a preferred embodiment of the present invention, the plasticizer is selected from the group consisting of triethyl citrate (TEC), polyethylene glycol, acetyl triethyl citrate, butyl citrate, polysorbates, 1,2-polyproppylene glycol and dibutyl sebacate (DBS), preferably DBS. The amount of plasticizer to be used in the sustained release coating liquid is not particularly limited. In one embodiment of the present invention, the sustained release coating liquid comprises 5-35 wt.-%, preferably 10-30 wt.-%, more preferably about 20-25 wt.-%, plasticizer, relative to the total weight of the sustained release polymer solids in the sustained release coating liquid.

It has been found by the present inventors that for solid dosage forms where a slow and constant sustained release, e.g. over a time period of 20 h or 24 h, is desirable, a hydrophobic plasticizer like DBS (compared to a more hydrophilic plasticizer) gives very advantageous results, giving rise to a slow and more constant sustained release of the at least one antibody or functional fragment thereof from the drug layer. Therefore, according to one embodiment of the present invention, the plasticizer in the sustained release coating liquid is DBS.

According to yet another embodiment of the present invention, the sustained release coating liquid in step d) comprises at least one coalescence enhancer. It has been found by the present inventors that the presence of a coalescence enhancer like propylene glycol monolaurate in the sustained release coating liquid can considerably improve the properties of the resulting sustained release coating, including the integrity of the resulting sustained release coating and an improved sustained release profile. Moreover, the presence of a coalescence enhancer like propylene glycol monolaurate in the sustained release coating liquid can considerably reduce the drying time necessary to give rise to the solid dosage form, thereby reducing processing time and costs. If a coalescence enhancer is included in the sustained release coating liquid, the resulting sustained release coating can result in a much more constant release rate of the at least one antibody or functional fragment thereof in the drug layer, e.g. over the course of 24 hours in an aqueous environment. Finally, the presence of a coalescence enhancer in the sustained release coating liquid can considerably reduce the amount of sustained release coating necessary to give rise to comparably slow release and a comparable release profile of the at least one antibody or functional fragment thereof as when no coalescence enhancer is present, due to its positive influence on film drying when using polymeric aqueous dispersions.

The coalescence enhancer to be used in the sustained release coating liquid is not particularly limited. According to one embodiment of the present invention, the coalescence enhancer to be used in the sustained release coating liquid is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, fatty alcohols such as cetyl alcohol or oleyl alcohol, sodium glycolate, sodium de(s)oxycholate, polyethylene glycol, polypropylene glycol, alkyl poly(ethylene oxide), alkyl glycoside, alkyl polyglucoside, octyl glucoside, decyl maltoside, propylene glycol monolaurate (e.g. Lauroglycol™ 90), and combinations thereof. In a preferred embodiment of the present invention, the coalescence enhancer to be used in the sustained release coating liquid is propylene glycol monolaurate (e.g. Lauroglycol™ 90). The amount of coalescence enhancer to be used in the sustained release coating liquid is not particularly limited. In one embodiment of the present invention, the sustained release coating liquid comprises 1-20 wt.-%, preferably 2-15 wt.-%, more preferably 5-10 wt.-%, coalescence enhancer, relative to the total weight of the sustained release polymer solids in the sustained release coating liquid.

In one embodiment of the present invention, the sustained release coating of step d), allows the recovery of at least 60%, preferably at least 70%, more preferably at least 80%, even more preferably at least 90%, even more preferably at least 95%, even more preferably at least 97%, even more preferably at least 98%, even more preferably at least 99%, most preferably at least 99.5%, of the at least one antibody or functional fragment thereof from the solid dosage form, in a sustained release, within a defined time period (e.g. 4 h, or 6 h, or 8 h, or 10 h, or 12 h, or 14 h, or 16 h, or 18 h, or 20 h, or 22 h, or 24 h, or 26 h, or 28 h, or 30 h, or 32 h, etc.) of continuously immersing the solid dosage form in an aqueous solution under continuous agitation of the aqueous solution. In another embodiment of the present invention, the sustained release coating of step d), allows the recovery of at least 60%, preferably at least 70%, more preferably at least 80%, even more preferably at least 90%, even more preferably at least 95%, even more preferably at least 97%, even more preferably at least 98%, even more preferably at least 99%, most preferably at least 99.5%, of the at least one antibody or functional fragment thereof from the solid dosage form, within a defined time period (e.g. 4 h, or 6 h, or 8 h, or 10 h, or 12 h, or 14 h, or 16 h, or 18 h, or 20 h, or 22 h, or 24 h, or 26 h, or 28 h, or 30 h, or 32 h, etc.) of continuously immersing the solid dosage form in an aqueous solution under continuous agitation of the aqueous solution, in a sustained release with a substantially constant release rate over at least 8 h, preferably at least 12 h, more preferably at least 16 h, even more preferably at least 20 h, most preferably at least 24 h.

In yet another embodiment of the present invention, the sustained release coating of step d), ensures a sustained release of the at least one antibody or functional fragment thereof over a time period of at least 5 h, preferably at least 8 h, more preferably at least 10 h, even more preferably at least 14 h, even more preferably at least 18 h, even more preferably at least 20 h, most preferably at least 24 h, upon continuously immersing the solid dosage form in an aqueous solution under continuous agitation of the aqueous solution In yet another embodiment of the present invention, the sustained release coating of step d), ensures a sustained release of the at least one antibody or functional fragment thereof, with a substantially constant release rate over at least 5 h, preferably at least 8 h, more preferably at least 10 h, even more preferably at least 14 h, even more preferably at least 18 h, even more preferably at least 20 h, most preferably at least 24 h, upon continuously immersing the solid dosage form in an aqueous solution under continuous agitation of the aqueous solution.

To preserve activity and stability of the antibody and functional fragment thereof used for the present invention, in accordance with the present invention, the conditions during preparation of the solid dosage form are such as to be conducive to the activity and stability of the antibodies and functional fragments thereof (e.g. by avoiding elevated temperatures, pressures, shear forces, enzymatic contaminations, etc.). Therefore, in one embodiment of the present invention at any time during steps a) and c) the temperature of the at least one antibody or functional fragment thereof is lower than the melting temperature (Tm) of the at least one antibody or functional fragment thereof. The above is understood to mean that in case more than one antibody or functional fragment are included the drug coating, the temperature is to be lower than the melting temperature (Tm) of the antibody or functional fragment thereof with the lowest Tm. In an alternative embodiment of the present invention at any time during steps a) and c) the temperature of the antibody or functional fragment thereof is lower than 65° C., preferably not higher than 60° C., more preferably not higher than 55° C. In yet another embodiment of the present invention, wherein after step c), as step d) at least one additional coating in the form of a sustained release coating is applied, the temperature of the solid dosage form comprising the at least one antibody or functional fragment thereof at any time during step d) is lower than the melting temperature (Tm) of the at least one antibody or functional fragment thereof. In yet another embodiment of the present invention, wherein after step c), as step d) at least one additional coating in the form of a sustained release coating is applied, the temperature of the solid dosage form comprising the antibody or functional fragment thereof at any time during step d) is not higher than 65° C., preferably not higher than 60° C.

The amount of the antibody or functional fragment thereof in the solid dosage form prepared by the inventive method will vary according to the pharmacological activity of the antibody or functional fragment, the indication to be treated, the targeted dosing regimen, the projected method of administration, the integrity, stability and dissolution behaviour of the final composition and other similar reasons. The amount of the at least one antibody or functional fragment thereof preferably is at least 0.01 wt.-%, more preferably at least 0.05 wt.-%, even more preferably at least 0.1 wt.-%, even more preferably at least 0.5 wt.-%, 0.7 wt.-% or 0.9 wt.-%, most preferably at least 2 wt.-%, based on the total weight of the drug coated and dried solid dosage form after step c). The amount of the antibody or functional fragment thereof preferably is generally up to 30 wt.-%, more preferably up to 25 wt.-%, even more preferably at least 15 wt.-%, even more preferably up to 10 wt.-%, based on the total weight of the drug coated and dried solid dosage form after step c).

In another embodiment of the present invention, the drug coated and dried solid dosage form after step c) comprises 0.01-25 wt.-%, preferably, 0.05-15 wt.-%, more preferably 0.1-10 wt.-%, even more preferably 0.5-5 wt.-%, even more preferably 0.7-3 wt.-%, even more preferably 0.9-2.5 wt.-%, of the at least one antibody or functional fragment thereof. In yet another embodiment of the present invention, the drug coating comprises 0.5-60 wt.-% antibody or functional fragment thereof, 1-90 wt.-% binder, 0.001-70 wt.-% buffer and 0-20 wt.-% anti-tacking agent; preferably 5-50 wt.-% antibody or functional fragment thereof, 10-90 wt.-% binder, 0.1-60 wt.-% buffer and 0-15 wt.-% anti-tacking agent; more preferably 10-50 wt.-% antibody or functional fragment thereof, 20-85 wt.-% binder, 0.1-60 wt.-% buffer and 0.5-10 wt.-% anti-tacking agent; most preferably 20-50 wt.-% antibody or functional fragment thereof, 30-80 wt.-% binder, 1-60 wt.-% buffer and 0-8 wt.-% anti-tacking agent, relative to the total weight of the dried drug coating.

The thickness of the drug coating after step c) of the inventive method, in one embodiment is not particularly limited. The thickness of the drug coating of the solid dosage form after step c) determines the amount of the antibody or functional fragment thereof in the solid dosage form prepared by the inventive method, at a given concentration of antibody or functional fragment thereof and a given formulation composition in the active agent coating liquid.

The inventive method ensures that the activity and stability of the at least one antibody or functional fragment thereof is preserved in the solid dosage form prepared according to the inventive method. The stability and activity of an antibody or fragment thereof can be estimated for example by determining the fraction of an antibody or functional fragment thereof present as dimers and other aggregates. According to one embodiment of the present invention, the fraction of total content of antibody or functional fragment thereof present in the solid dosage form as dimers and other aggregates does not exceed more than 15%, preferably 12%, more preferably 10%, even more preferably 8%, even more preferably 7%, even more preferably 5%, even more preferably 3%, 2%, or 1.5%, the fraction of total antibody or functional fragment thereof present as dimers and other aggregates at the time of adding the antibody or functional fragment thereof to the active agent coating liquid. Methods to determine the fraction of a polypeptide present as dimers and other aggregates are known in the art, and include for example Size Exclusion Chromatography (SEC).

The stability and activity of an antibody or functional fragment thereof can also be estimated for example by determining the fraction of an antibody or functional fragment thereof present as fragments of the full-length antibody or functional fragment thereof. Therefore, in another embodiment of the present invention, the fraction of total content of antibody or functional fragment thereof present in the solid dosage form as fragments of the full-length antibody or functional fragment thereof does not increase substantially compared to the time of adding the antibody or functional fragment thereof to the binding liquid. The term "substantially" as used herein refers to a deviation from a stated condition by not more than 50%, preferably not more than 20%, more preferably not more than 15%, even more preferably not more than 10%, even more preferably not more than 7%, even more preferably not more than 5%, 3%, 2%, 1.5% or 1%.

In a further embodiment of the present invention, the fraction of total content of antibody or functional fragment thereof present in the solid dosage form as fragments of the full-length antibody or fragment thereof does not exceed by more than 15%, preferably 12%, more preferably 10%, even more preferably 8%, even more preferably 7%, even more preferably 5%, even more preferably 3%, 2%, or 1.5%, the fraction of total content of antibody or functional fragment thereof present as fragments of the full-length antibody or functional fragment thereof at the time of adding the antibody or functional fragment thereof to the active agent coating liquid. Methods to determine the fraction of an antibody or functional fragment thereof present as fragments of the full-length antibody or functional fragment thereof are known in the art, and include for example microchip electrophoresis analysis.

In one embodiment of the present invention the antibody or functional fragment thereof is suitable for use in the topical treatment in the gastrointestinal tract of a patient. The term "topical treatment" in the context of the present invention, is used to describe the local application of the solid dosage form, as opposed to the systemic application of a dosage form comprising antibodies or functional fragments thereof, e.g. by infusion, injection or implantation. The term "gastrointestinal tract" as used herein describes the system of organs of the human body, that includes all structures between mouth and anus, forming a continuous passage, and is responsible for digesting ingested material, absorbing nutrients and expelling faeces. The term "patient" as used herein refers to a living organism suffering from or prone to a condition that can be treated or prevented by the administration of the at least one antibody or functional fragment thereof. In a preferred embodiment, the patient is a human.

A pharmaceutical composition in the form of one or multiple solid dosage forms allows once-daily delivery of the above classes of antibodies and functional fragments thereof. The topical treatment in the gastrointestinal tract, e.g. the ileum or the large intestine, ensures specific targeting of the gastrointestinal wall, for enhanced treatment of diseases of the ileum and large intestine, by providing high local concentration of antibody or functional fragment thereof, while minimizing side effects that occur because of release of drugs in the upper gastrointestinal tract or unnecessary systemic absorption.

Therefore in another embodiment of the present invention the solid dosage form prepared by the inventive method is for use in the treatment of a disease in the gastrointestinal tract, preferably in the ileum and the large intestine. Such diseases include e.g. IBD, cancer (such as colorectal cancer or small intestine cancer), celiac disease, infections (such as Clostridium difficile infection) of the small intestine and the colon, and diarrhea. In a preferred embodiment of the present invention the solid dosage form prepared by the inventive method is for use in the treatment of an IBD, e.g. Crohn's disease or ulcerative colitis.

In one embodiment of the present invention, the solid dosage form prepared by the method of the present invention is for oral administration. "Oral administration" in context of the present invention means the introduction of the solid dosage form into gastrointestinal tract via the mouth.

According to one embodiment of the present invention at least one additional coating in the form of a delayed release coating is applied to the solid dosage form after drying in step c), or after step d) if at least one additional coating in the form of a sustained release coating is applied as step d). A delayed release coating within the meaning of the present invention is a coating that prevents the release of the antibody or functional fragment thereof from the solid dosage form, until a specific event, e.g. in the form of a chemical or enzymatic trigger or the lapse of a defined amount of time immersed in solution, occurs.

In a preferred embodiment, the solid dosage form prepared by the method of the present invention is for oral administration, in the form of a pellet, bead, sphere, mini spheres, tablet, mini tablet, or granule coated with a delayed release coating that prevents the release of the composition before the ileum, preferably before the terminal ileum, more preferably before the ileocolonic region, alternatively before the ascending colon, before the transverse colon or before the descending colon, of the gastrointestinal tract. The ileocolonic region is the region of the gastrointestinal tract where the small intestine merges with the large intestine. The large intestine is the penultimate section of the gastrointestinal tract and can be further subdivided into cecum, colon and rectum. The colon is further subdivided into ascending, transverse and descending colon. The terminal ileum is the penultimate section of the small intestine and is directly adjacent to the cecum.

The approach for applying the delayed release coating is not particularly limited as long as it does not affect the stability and activity of the at least one antibody or functional fragment thereof in the drug coating. Methods for applying delayed release coatings are known in the art. In one embodiment of the present invention the delayed release coating is applied by spray coating, preferably fluidized-bed spray coating.

Coating materials for the delayed release of a solid dosage form, in particular for targeted release in the ileum or the large intestine, upon oral administration are known in the art. They can be subdivided into coating materials that disintegrate above a specific pH, coating materials that disintegrate after a specific residence time in the gastrointestinal tract and coating materials that disintegrate due enzymatic triggers specific to the microflora of a specific region of the intestines. Coating materials of these three different categories for targeting to the large intestine have been reviewed for example in Bansal et al. (Polim. Med. 2014, 44, 2,109-118). The uses of such coating materials have also been described for example in WO2007/122374A2, WO0176562A1, WO03068196A1 and GB2367002A. In one embodiment of the present invention the delayed release coating comprises at least one component selected from coating materials that disintegrate pH-dependently, coating materials that disintegrate time-dependently, coating materials that disintegrate due to enzymatic triggers in the intestinal environment (preferably in the intestinal environment of the ileum and the large intestine), and combinations thereof.

Preferred coating materials among coating materials that disintegrate pH-dependently are selected from poly vinyl acetate phthalate, cellulose acetate trimellitate, hydroxypropyl methylcellulose phthalate HP-50, HP-55 or HP-55S, cellulose acetate phthalate, hydroxypropyl methylcellulose acetate succinate (HPMCAS), poly(methacrylic acid, ethyl acrylate) 1:1 (Eudragit® L100-55, Eudragit® L30D-55), poly(methacrylic acid, methyl methacrylate) 1:1 (Eudragit® L-100, Eudragit® L12.5), poly(methacrylic acid, methyl methacrylate) 1:2 (Eudragit® S-100, Eudragit® S12.5, Eudragit® FS30D), and combinations thereof. Preferred coating materials among coating materials that disintegrate time-dependently are selected from Eudragit® RL, Eudragit® RS, ethylcellulose and combinations thereof. Preferred coating materials among coating materials that disintegrate due to enzymatic triggers in the large intestinal environment are selected from chondroitin sulfate, pectin, guar gum, chitosan, inulin, lactulose, raffinose, stachyose, alginate, dextran, xanthan gum, locust bean gum, arabinogalactan, cyclodextrin, pullulan, carrageenan, scleroglucan, chitin, curdulan, levan, amylopectin, starch, amylose, resistant starch, azo compounds being degraded by azo bonds splitting bacteria, and combinations thereof. The delayed release coating optionally comprises at least one further excipients as e.g. listed in one of the embodiments above.

In one embodiment of the present invention the coating material for the delayed release coating comprises one, two, three, etc., components selected from the coating materials that disintegrate pH-dependently, the coating materials that disintegrate time-dependently, and the coating materials that disintegrate due to enzymatic triggers in the intestinal environment, listed above, and combinations thereof. In another embodiment of the present invention, the delayed release coating comprises a combination of at least one coating material that disintegrates pH-dependently and at least one coating material that disintegrates due to enzymatic triggers in the large intestinal environment.

For example, a delayed release coating can be designed to focus the delivery of the antibody or functional fragment thereof entirely in the large intestine, beginning at the cecum, and continuing through the ascending, transverse, and descending colon, and ending in the sigmoid colon. Alternatively, for example, a delayed release coating can be designed to begin the delivery of the antibody or functional fragment thereof in the jejunum and end the release in the transverse colon. The possibilities and combinations are numerous.

In one embodiment of the present invention, the delayed release coating comprises a combination of at least one pH sensitive (enteric) polymer, e.g. poly(methacrylic acid, methyl methacrylate) 1:2, and at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, e.g. resistant starch. In a preferred embodiment of the present invention, the delayed release coating is a combination of poly(methacrylic acid, methyl methacrylate) 1:2 (Eudragit® S) and resistant starch (e.g. Phloral® technology). The delayed release coating comprising the at least one component, e.g. the combination of at least one enteric polymer, e.g. poly(methacrylic acid, methyl methacrylate) 1:2, and at least one polysaccharide, e.g. resistant starch, may be dispersed in an organic solvent, a mixture of organic solvents or a mixture of at least one organic solvent and water, and then applied to the solid dosage form e.g. by fluidized-bed spray coating.

In another embodiment, the delayed release coating comprises i) an inner coating comprising a partially neutralized pH sensitive (enteric) polymer adjusted to pH 8 (e.g. neutralized poly(methacrylic acid, methyl methacrylate) 1:2 adjusted to pH 8) and containing a buffer salt, and ii) an outer coating comprising a combination of at least one enteric polymer (preferably poly(methacrylic acid, methyl methacrylate) 1:2) and at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, preferably resistant starch (e.g. OPTICORE™). Other preferred embodiment for the delayed release coating can be found among the embodiments disclosed in WO2007122374A2. According to a further aspect of the present invention, in a further step a sachet/stick pack, a spheroid/sphere, a tablet, a straw device (i.e. X-Straw®) or a capsule (e.g. a hard or soft gelatin capsule) or is provided (multiparticulate drug delivery system) comprising multiple solid dosage form units prepared by the inventive method according to one of the embodiments described above. How to prepare sachets/stick packs, tablets or capsules comprising multiple solid dosage form units is known in the art. The sachet/stick pack, straw device (Xstraw®), spheroid/sphere, tablet or a capsule may comprise a total amount of the at least one antibody or functional fragment thereof suitable for oral administration to a human patient. In another embodiment, the sachet/stick pack, straw device (Xstraw®), tablet or capsule comprises a therapeutically effective dose of the at least one antibody or functional fragment thereof suitable for oral administration to a human patient.

In an alternative embodiment of the present invention, multiple solid dosage form units prepared by steps a) to c), or alternatively steps a) to d), of the inventive method, as described in one of the inventive embodiments above, may be combined into a multiparticulate drug delivery system, e.g. a tablet, spheroid/sphere, or capsule. How to prepare such tablets or capsules comprising multiple units is known in the art. The thus prepared multiparticulate drug delivery system (e.g. tablet, spheroid/sphere or capsule may then be coated with a delayed release coating as described above.

In addition to a method for preparing a solid dosage form as described in the embodiments above, the present invention further relates to solid dosage forms obtainable by the method of the present invention as defined by any one of the embodiments described above. The inventive solid dosage forms may be in the form of pellets, beads, spheres, mini spheres, granules, tablets or mini tablets. The present invention also relates to a multiparticulate drug delivery system in the form of a sachet/stick pack, straw device (XStraw®), capsule, spheroid/sphere or tablet/mini tablet comprising multiple solid dosage forms prepared by the inventive method described above. Furthermore, the present invention relates to said solid dosage forms and multiparticulate drug delivery systems for use in the treatment of a gastrointestinal disease, e.g. an IBD, colorectal cancer, small intestine cancer, celiac disease, or gastrointestinal infections (e.g. Clostridium difficile infection), preferably an IBD, e.g. Crohn's disease or ulcerative colitis. The present invention also relates to solid dosage forms and multiparticulate drug delivery systems prepared by the inventive method described above for use in the topical treatment in the gastrointestinal tract of a patient. Finally the present invention relates to said inventive solid dosage forms and multiparticulate drug delivery systems for use in the treatment of a patient suffering from a gastrointestinal disease, preferably IBD, colorectal cancer, small intestine cancer, or gastrointestinal infections, more preferably IBD.

In further aspect the present invention relates to a multiparticulate drug delivery system comprising a plurality of solid dosage form units (i.e. single solid dosage forms, for example spheroids/spheres), each solid dosage form unit comprising i) an inert core unit, and ii) a drug coating comprising at least one antibody or functional fragment thereof, a buffer and at least one polymeric binder, and optionally an anti-tacking agent and/or a surfactant, and preferably each solid dosage form unit having a predetermined axis and the same predetermined cross-sectional profile, wherein at least 80% by number of those solid dosage form units, preferably 90%, more preferably 95%, have a median aspect ratio between 0.7 and 1.7, the aspect ratio being defined as solid dosage form unit length along the predetermined axis divided by the smallest cross-sectional dimension.

According to one embodiment of the multiparticulate drug delivery system of the present invention, the median aspect ratio is above 0.8, preferably above 0.9, and below 1.6, preferably below 1.5, more preferably 1.4, even more preferably below 1.3, even more preferably below 1.2, most preferably about 1. According to another embodiment of the multiparticulate drug delivery system of the present invention, the solid dosage form units have a span of aspect ratio of less than 0.9, preferably less than 0.8, more preferably less than 0.7, even more preferably less than 0.6, most preferably less than 0.5. For further details regarding aspect ratio, predetermined axis, predetermined cross-sectional profile and span (including definitions and embodiments), it is referred to the disclosure of EP 2 512 453. It is to be understood that the above definitions and embodiments regarding aspect ratio and span of the solid dosage form units equally apply to the inventive solid dosage forms according to any one of the embodiments above and to the solid dosage forms prepared by any one of the embodiments of the inventive method described above.

According to a further embodiment of the present invention, the multiparticulate drug delivery system of the present invention, allows the recovery of at least 80%, preferably at least 85%, more preferably at least 93%, even more preferably at least 95%, even more preferably at least 97%, even more preferably at least 98%, of the at least one antibody or functional fragment thereof from the solid dosage form units.

According to yet another embodiment of the present invention, the multiparticulate drug delivery system of the present invention allows the recovery of at least 80%, preferably at least 85%, more preferably at least 93%, even more preferably at least 95%, even more preferably at least 97%, even more preferably at least 98%, of the at least one antibody or functional fragment thereof from the solid dosage form units, in an immediate release, within 30 min, or 1 h, or 2 h, or 4 h, of continuously immersing the solid dosage form in an aqueous solution under continuous agitation.

According to yet another embodiment of the present invention, the solid dosage form units comprised in the multiparticulate drug delivery system are sustained release solid dosage form units. According to yet another embodiment of the present invention, the multiparticulate drug delivery system of the present invention allows the recovery of at least 80%, preferably at least 85%, more preferably at least 93%, even more preferably at least 95%, even more preferably at least 97%, even more preferably at least 98%, of the at least one antibody or functional fragment thereof from the solid dosage form units, in a sustained release, within 4 h, or 6 h, or 8 h, or 10 h, or 12 h, or 14 h, or 16 h, or 18 h, or 20 h, or 22 h, or 24 h, or 26 h, or 28 h, or 30 h, or 32 h, or 34 h, or 36 h, etc., of continuously immersing the solid dosage form in an aqueous solution under continuous agitation.

In one embodiment of the multiparticulate drug delivery system, the solid dosage form units comprise the antibody or functional fragment thereof, the buffer and at the least one polymeric binder in a drug coating which is applied to the inert core unit by spray coating. According to a specific embodiment of the present invention, the solid dosage form units comprised in the multiparticulate drug delivery system are solid dosage forms prepared by drug layering according to the method of any one of the embodiments described above.

In a further embodiment of the present invention, the multiparticulate drug delivery system or the individual solid dosage form units comprise a delayed release coating, which is applied as a further coating. Further embodiments for the multiparticulate drug delivery system may be found in EP 2 512 453 and are applicable to the present invention independent of whether these embodiments are disclosed in EP 2 512 453 as referring to spheronized/non-spheronized solid dosage form units. According to another aspect, the present invention relates to a solid dosage form which consists of a single dosage form unit corresponding to one of the single dosage form units comprised in the multiparticulate drug delivery system defined in any of the embodiments above.

EXAMPLES

Materials and Methods Applied in the Examples

TABLE 1

| Instrumental parameter varied for process optimization using Minicoater from Caleva | |
| --- | --- |
| Instrumental parameters | Range |
| Silicon tubing diameter (mm) | 0.8 and 1.6 |
| Flow rate (rpm) | 2-4 |
| Inlet temperature (° C.) | 40-55 |
| Fan speed (m/s) | 12-15 |
| Container vibration frequency (Hz) | 10-14 |

TABLE 1-continued

| Instrumental parameter varied for process optimization using Minicoater from Caleva | |
| --- | --- |
| Instrumental parameters | Range |
| Atomizing pressure (kPa) | 20-25 |
| Nozzle position (depth), cm | 10-15 |

Preparation of Citrate-TRIS Buffer pH 7

A citrate-TRIS buffer was prepared at pH 2.0 by adjusting the pH of 200 mL of 0.1 M citric acid solution to 3.5 by adding the adequate amount of a 0.1 M sodium citrate solution. The pH of the resulting citrate buffer was then adjusted to 7.0 by adding the adequate amount of a 1M TRIS solution.

Layering

Layering onto pellets (Cellets®/Suglets®) was done using a fluidized-bed coater (Minicoater). Between 10-20 g of microcrystalline cellulose pellets (Cellets®) or sucrose pellets (Suglets®), were placed in the container and pre-heated under 10 Hz agitation of 45° C. and 12 m/s fan speed for 10 min. The nozzle was placed at the determined height above the pellet bed. The fan, agitator and heater were then turned on and the spraying was started by turning on the pump and the atomizing air. Table 1 lists the instrumental parameters varied for the layering optimization.

Microchip Electrophoresis Analysis

Microchip (labchip) electrophoresis analysis was carried out using standard conditions and settings. In short, the supernatant (2 µl) of samples containing adalimumab was tested for the presence of fragments by microchip gel electrophoresis under non-reducing conditions. In all experiments a positive control of adalimumab 1 mg/ml in citrate-TRIS buffer pH 7 was used. Samples were diluted to yield an adalimumab concentration of 1 mg/ml.

Size Exclusion Chromatography (SEC)

High performance liquid chromatography (HPLC)—SEC was carried out using standard conditions and settings. In short, the supernatant of samples containing adalimumab was tested for the presence of aggregates (dimers, oligomers) by SEC. In all experiments a positive control of adalimumab 1 mg/ml in citrate-TRIS buffer pH 7 was used.

Effect of Process Parameters on Adalimumab Stability

The effect of process parameters on adalimumab was assessed by processing a 2.5 wt.-% HPMC solution containing 0.25 wt.-% Syloid® 244FP and 5 mg/ml adalimumab. 500 µl of the coating suspension were sampled at different intermediate processing steps. The formation of dimers and other aggregates, fragments, and total protein content were measured by SEC, Microchip gel electrophoresis, and Bradford method, respectively. A 1 mg/ml adalimumab solution in citrate-TRIS buffer pH 7 was used as positive control (standard).

Determination of Relative Humidity Content

The amount of moisture (water) contained in the inert cores and layered microcrystalline cellulose/sucrose pellets and in coated pellets were gravimetrically measured using loss on drying (LOD) at 105° C. for 1 hour.

Calculation of Adalimumab Loading

The theoretical loading of adalimumab was calculated based on the amount of solid layered material and on the known adalimumab concentration in the spraying suspension. Therefore, the pellets were weighted before and after layering and drying. The exact amount of moisture contained in the initial inert cores, adalimumab layered and sustained release coated pellets must be accounted for.

Coating of Adalimumab Layered Pellets with Eudragit® RS 30D

Adalimumab layered pellets (HPMC-based formulation) were further coated with an aqueous redispersion of Eudragit® RS 30D. The formulation of Eudragit® RS 30D followed the standard recommendations from Evonik. The Eudragit® RS 30D coating suspension was prepared at 10% solids content from the 30% solids commercial dispersion. Triethyl citrate (TEC) was used as plasticizer and Syloid® 244 FP was used as anti-tacking agent, unless specified otherwise. An excess coating suspension was prepared to account for spraying losses due to the small batch size. Adalimumab layered pellets were coated until a target polymer weight gain was reached (5-25%). The coated pellets were then cured at 40° C. in a drying cabinet (oven) with air circulation up to 24 h. In selected formulations, propylenegylcol monolaureate (Lauroglycol™ 90) was used as coalescence enhancer.

Coating of Adalimulab Layered Pellets with Aquacoat® ECD

Adalimumab layered pellets (HPMC-based formulation) were further coated with an aqueous redispersion of ethylcellulose (Aquacoat® ECD). Aquacoat® ECD formulations do not require an anti-tacking agent. Triethyl citrate (TEC) and dibutyl sebacate (DBS) were used as plasticizer (20-25% based on polymer solid content). Additionally, selected formulations contained also a coalescence enhancer (Lauroglycol™ 90). Adalimumab layered pellets were coated until a target polymer weight gain was reached (5-20%). An excess coating suspension was prepared to account for spraying losses due to small batch size. The coated pellets were then cured at 60° C. in a drying cabinet (oven) with air circulation for up to 24 h with intermediate sample taking.

Adalimumab Release

Dissolution of coated pellets (Cellets®/Suglets®) was performed by agitating the coated pellets in citrate-TRIS buffer pH 7. The amount of coated pellets weighted per tube was calculated in order to yield a theoretical 1 or 1.5 mg/mL adalimumab concentration in the buffer, considering the theoretical adalimumab loading. At defined time points, 200 µl supernatant were pipetted out into an Eppendorf tube and diluted if required with citrate-TRIS buffer pH 7. The samples were then centrifuged 5 min at 3000 rcf and the supernatant was then used for further analysis.

Total Protein Determination

Total protein quantification was done by colorimetry following the Bradford method with a Coomassie Plus assay (Thermo Scientific). Briefly, 6.6 µl of sample were pipetted into to bottom of a disposable cuvette and 200 µl of Coomassie Plus reagent were added and mixed by agitation for 30 s at 500 rpm. The samples were then incubated at room temperature for 10 minutes after which the absorbance at 595 nm was recorded using a spectrophotometer and the blank was subtracted. Quantification was done using a freshly prepared standard curve.

ELISA Analysis

The binding of adalimumab to TNFα was assessed by an ELISA method. Briefly, well plates were coated with human TNFα (0.5 mg/ml) in PBS using 100 µl/well for 1 hour at room temperature. Adalimumab binding was assessed using a HRP AffiniPure Donkey anti-human IgG (H+L) of 0.05 µg/mL using tetramethylbenzidine (TMB) as substrate. Samples were centrifuged and diluted with 1% BSA in PBS to a target adalimumab concentration of 10 ng/ml.

Results

TABLE 1

Composition summary of coated pellets

| Formulation | Inert cores | Release profile |
|---|---|---|
| Example 1 | Microcrystalline cellulose pellets | Immediate release |
| Example 2 | Sucrose pellets | Immediate release |
| Example 3 | Microcrystalline cellulose pellets | Immediate release |
| Example 4 | Microcrystalline cellulose pellets | Immediate release |
| Example 5 | Microcrystalline cellulose pellets | Immediate release |
| Comparative Example 1 | Sucrose pellets | Immediate release |
| Example 6 | Sucrose pellets | Sustained release |
| Example 7 | Sucrose pellets | Sustained release |
| Example 8 | Sucrose pellets | Sustained release |
| Example 9 | Sucrose pellets | Sustained release |
| Example 10 | Sucrose pellets | Sustained release |
| Example 11 | Sucrose pellets | Sustained release |
| Example 12 | Sucrose pellets | Sustained release |
| Example 13 | Sucrose pellets | Sustained release |
| Example 14 | Sucrose pellets | Immediate release |
| Example 15 | Sucrose pellets | Immediate release |
| Example 16 | Sucrose pellets | Immediate release |
| Example 17 | Sucrose pellets | Immediate release |

Experiment 1—Immediate Release Coating of Pellets

Influence of Process Parameters on Adalimumab Stability

Figure 1B:
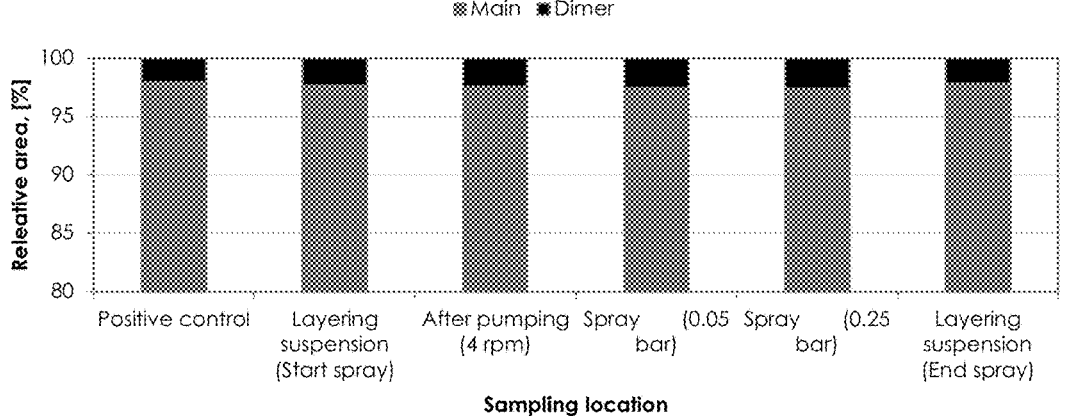
Figure 1C:
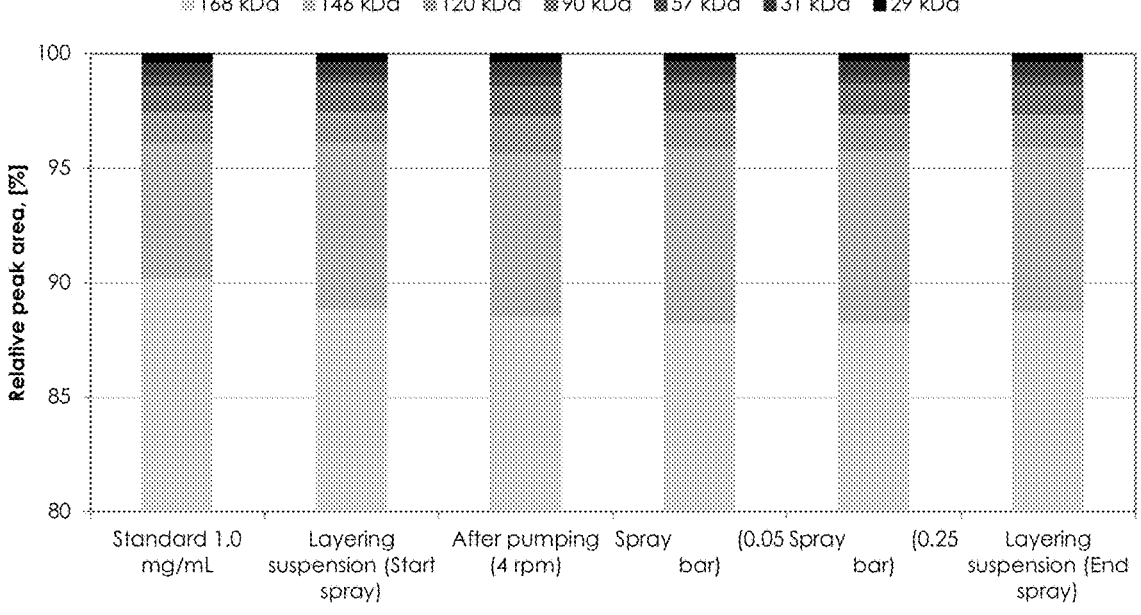

The effect of some process variables on adalimumab in an HPMC-Syloid® 244 FP suspension containing 5 mg/ml adalimumab was assessed in terms of total protein content, aggregation and fragmentation (FIG. 1A-C). Adalimumab is fully recovered from the spraying liquid after each processing step, indicating that does not adsorb to the surfaces through where the suspension is transported. Due to fast evaporation of the droplets after atomization (decreased volume), an apparent higher adalimumab recovery above 100% is observed. No significant increase in dimer content (FIG. 1B) in comparison to the positive control (1.0 mg/mL standard) was observed for the samples collected during the process. Similarly no significant increase in adalimumab fragments was seen in comparison to the positive control (FIG. 1C).

Adalimumab Layering on Inert Core Units (Pellets)

Pellets were layered using the optimized process parameters determined from preliminary placebo trials.

Figure 2:
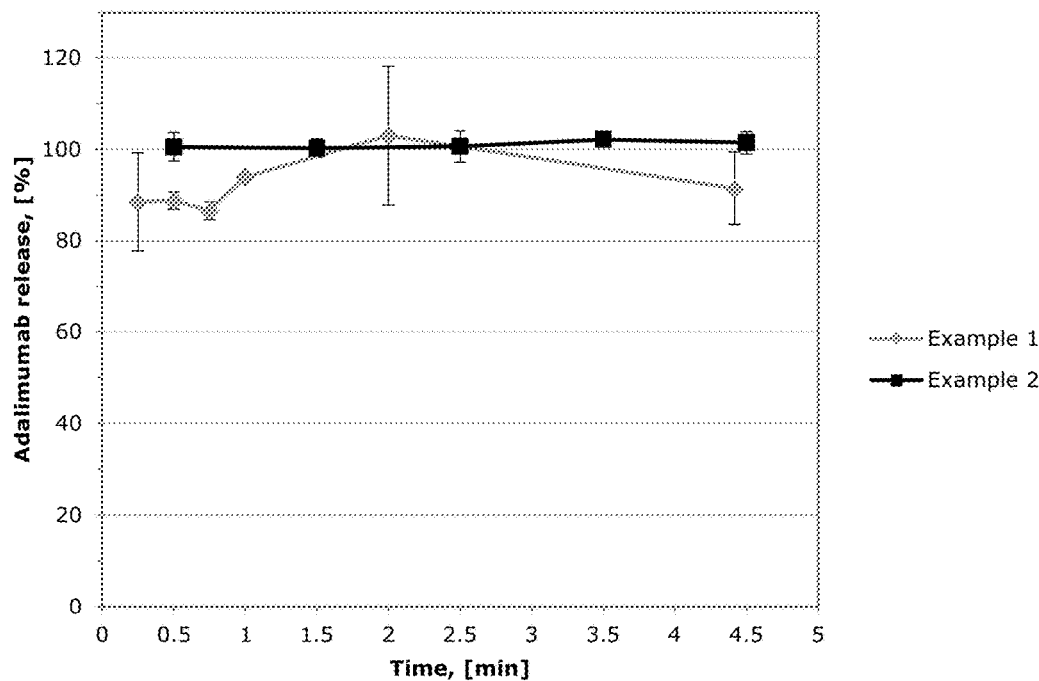
FIG. 2 shows the adalimumab release from HPMC layered microcrystalline (Example 1) and sucrose pellets (Example 2) in citrate-TRIS buffer pH 7. The protein recovered in the citrate-TRIS pH 7 dissolution buffer was quantified by total protein determination. A complete adalimumab release was reached very quickly in both cases. Average and standard deviation of 3 measurements shown.

Adalimumab Release from HPMC-Layered Microcrystalline (Cellets®) and Sucrose (Suglets®) Pellets FIG. 2 shows the release of adalimumab from HPMC-layered pellets in citrate-TRIS buffer pH 7. The adalimumab recovered in the citrate-TRIS pH 7 dissolution buffer overtime was quantified by total protein determination. A complete adalimumab release was reached very quickly in both cases. As expected, the inert core used for the layering process is irrelevant for the release of the layered antibody. Similarly, the inert core did not have any influence on the dimer to monomer content and fragmentation profile of adalimumab after formulation and recovery from dissolution samples (data not shown).

Figure 3A:
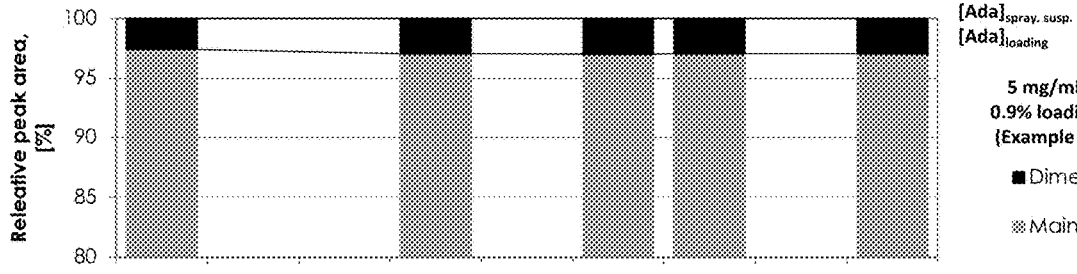
FIG. 3A shows the relative dimer to monomer content of adalimumab released from HPMC-layered pellets in citrate-TRIS buffer pH 7 over time determined by HPLC-SEC. No significant increase in dimer content in comparison to the positive control was observed upon dissolution, independent of the adalimumab loading and initial concentration (Example 3, 4 and 5). The concentration of adalimumab in the coating suspension and target loading were varied.
Figure 3A:
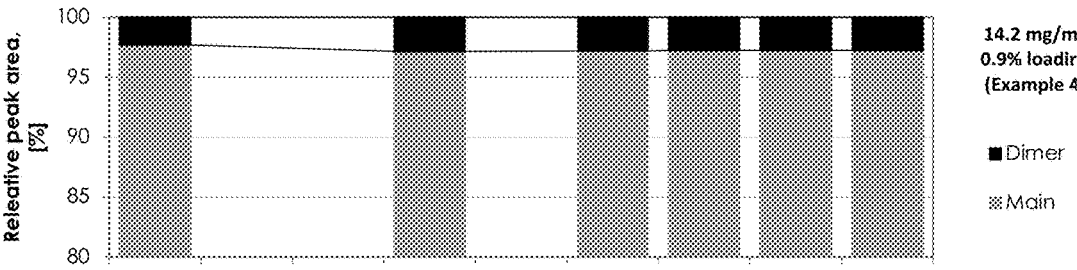
Figure 3A:
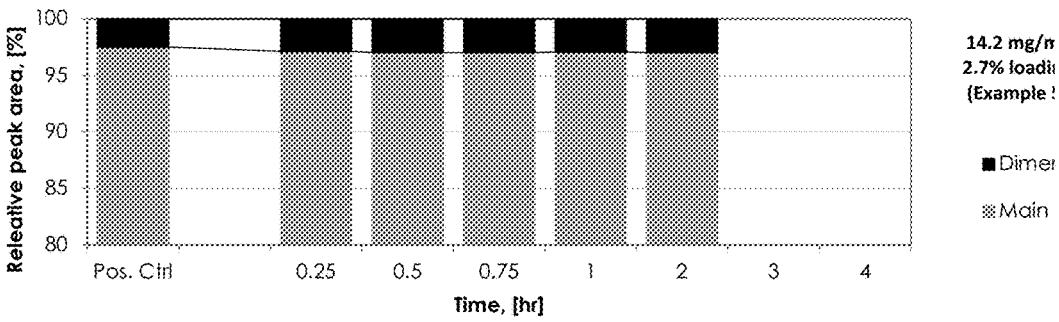
Figure 3B:
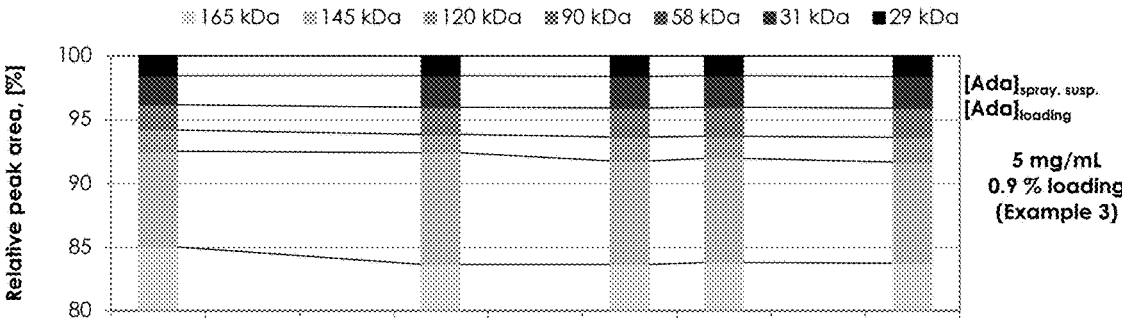
FIG. 3B shows the relative fragmentation profile of adalimumab released in citrate-TRIS buffer pH 7 over time. No significant fragmentation was observed as compared to the positive control for Example 3, 4 and 5.
Figure 3B:
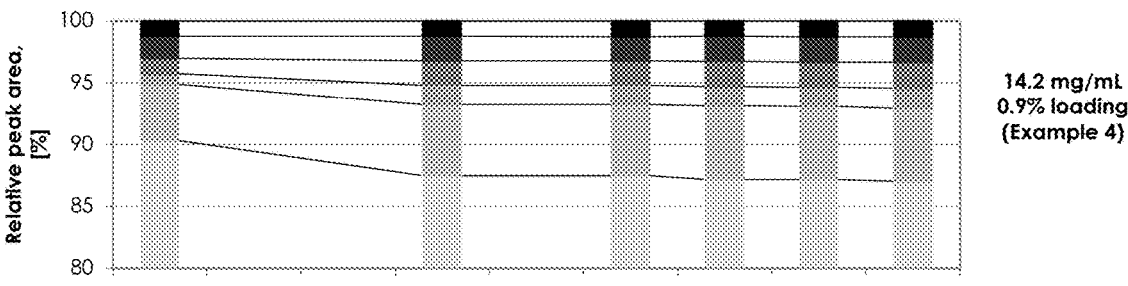
Figure 3B:
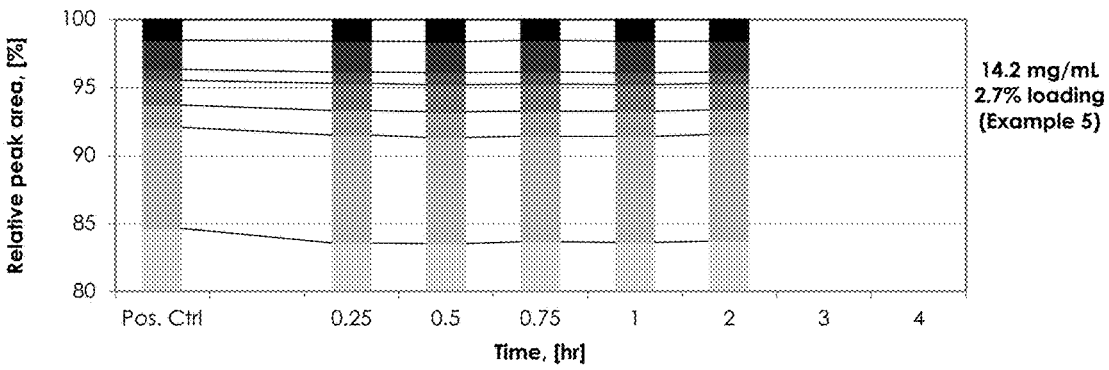

FIG. 3A shows the relative dimer to monomer content of adalimumab released from HPMC-layered pellets in citrate-TRIS buffer pH 7 over time. No significant increase in dimer content in comparison to the adalimumab standard (positive control) was observed upon dissolution, independent of the adalimumab loading and initial concentration as seen for Examples 3, 4 and 5, where the initial adalimumab concentration in the layering suspension varied between 5 mg/ml and 14.2 mg/ml and the adalimumab loading on the pellets varied between 0.9 and 2.7 wt %. FIG. 3B shows the relative fragmentation profile of adalimumab released in citrate-TRIS buffer pH 7 over time. No significant fragmentation was observed as compared to the positive control. The quality of adalimumab was also preserved in terms of acidic and basic species formation (no significant differences in protein surface charge) (data not shown). Similar results regarding aggregation, fragmentation and acidic and basic species formation after release from layered pellets were observed for methylcellulose-layered pellets (data not shown).

Figures 4A, 4B:
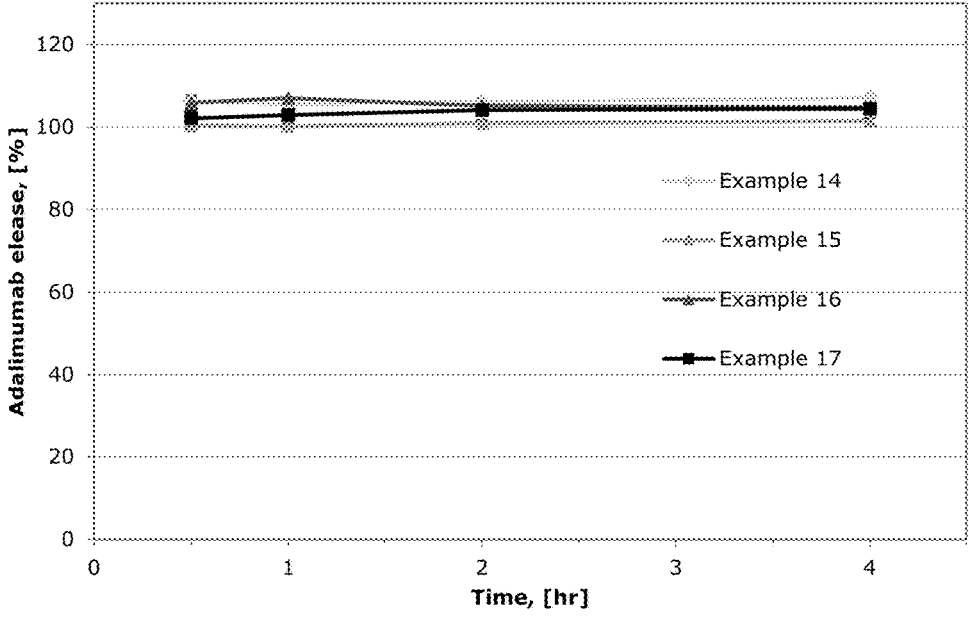
FIG. 4A shows the composition of coating suspension prepared with increased adalimumab concentration.
FIG. 4B shows the adalimumab release from coated pellets in citrate-TRIS buffer pH 7 from pellets layered with different coating suspensions (Examples 14, Example 15, Example 16 and Example 17).
Figure 4C:
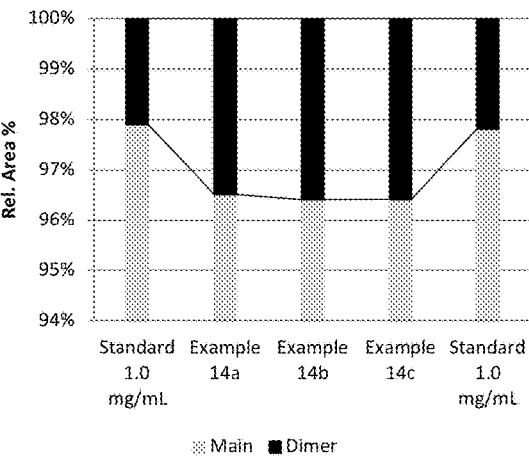
FIG. 4C shows the relative adalimumab aggregation and fragmentation profile of dissolution samples from Example 14 pellets in comparison to the adalimumab standard.
Figure 4C:
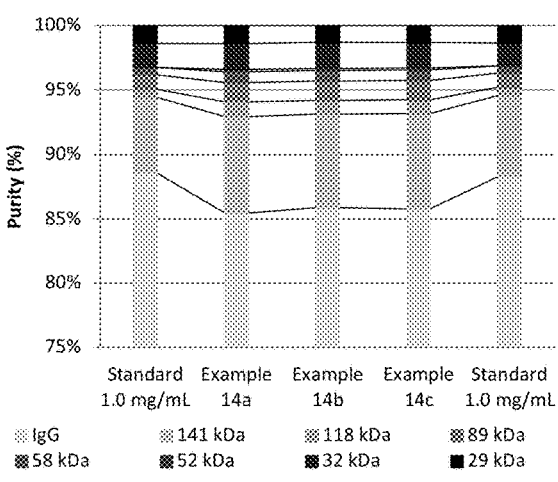

Experiment 2—Immediate Release Coating Using High Adalimumab Concentration in Coating Suspension The adalimumab concentration in the initial coating suspension was increased from 14.2 mg/mL to 25 mg/mL or 50 mg/mL, which has the potential to shorten process duration and reduce process costs (see FIG. 4A). The resulting coated pellets (Examples 14, 15, 16 and 17) all displayed a fast release profile in citrate-TRIS buffer pH 7 with complete release within 30 min (FIG. 4B). Thus there is no impact on adalimumab concentration in coating suspension on release profile. An increase in antibody concentration up to 50 mg/mL (Example 14) used in the initial suspension did not result in more than 1.5% increase in aggregates and 3% increase in fragments when compared to the 1.0 mg/mL adalimumab standard (FIG. 4C).

Experiment 3—Sustained Release Polymeric Binder in Drug Coating

Sustained release polymeric binder were tested for inclusion in the drug coating. Polymeric binders that were tested included Eudragit® NM 30D, Surelease® (ethylcellulose aqueous dispersion) and Eudragit® RS 30D. Compatibility studies as carried out for HPMC and MC in Example 1 revealed no significant increase in adalimumab aggregation and fragmentation (data not shown). Pellets were layered with coating suspension comprising at least one sustained release polymeric binder using the optimized layering parameters. The ratio of sustained release polymeric binder to adalimumab concentration was varied. It was found that by changing the ratio of polymeric binder to antibody, the antibody release from the drug coating could be modified.

Experiment 4—Sustained Release Coating of Adalimumab Immediate Release Coated Pellets

Starting Material for Sustained Release Coating

In a first step, adalimumab was layered onto pellets (Suglets®) using a HPMC-based formulation, containing 10% Syloid® 244 FP (based on polymeric binder solids) as described before. Subsequently, adalimumab layered pellets were used for coating trials with Eudragit® RS 30D or Aquacoat® ECD as sustained release polymers.

Eudragit® RS 30D Coated Pellets

Figures 5A, 5B:
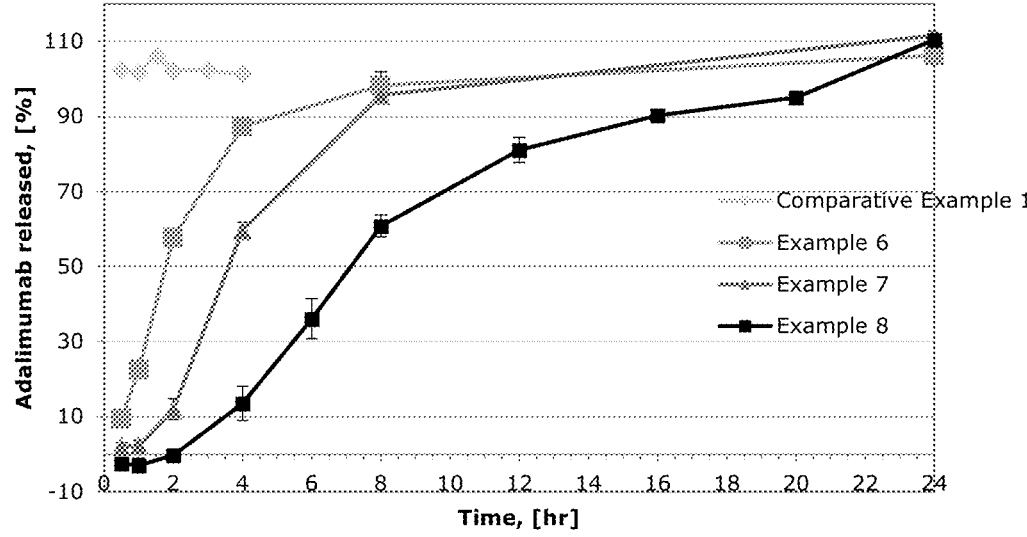
FIGS. 5A-5C describe a Eudragit® RS 30D coating of adalimumab coated pellets.
Figure 5C:
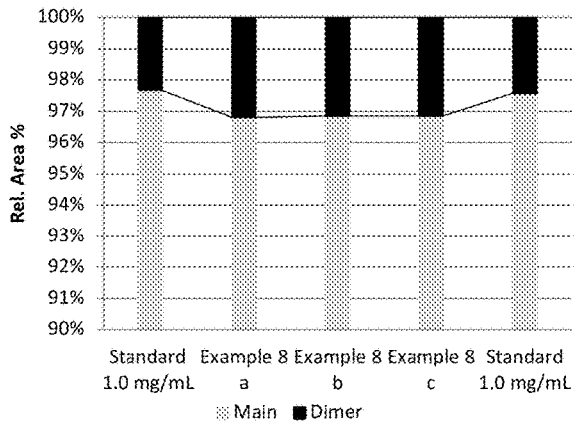
Figure 5C:
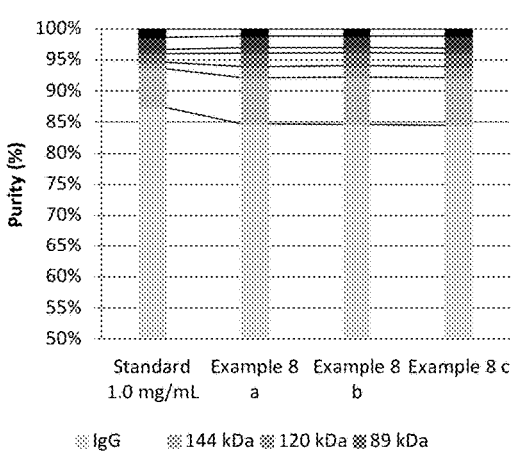

FIG. 5A shows the summary of the batches produced with Eudragit® RS 30D as sustained release polymer. Increasing the amount of Eudragit® RS 30D coating applied (from 6.89 wt.-% to 23.14 wt.-%) significantly reduced the adalimumab release rate from the coated pellets (FIG. 5B) in citrate-TRIS pH 7 buffer. The lowest coating amount (Example 6) was enough to sustain adalimumab release for 8 h. Increasing the coating amount to up to 23.14 wt.-% (Example 8) resulted in a sustained release during 24 h (FIG. 5B). The formulation itself and the process conditions and duration, including a drying step of 24 h at 40° C. did not affect the stability of adalimumab after being release from the coated pellets as described for Example 8a-c (triplicates). No significant differences were seen in terms of adalimumab aggregation profile and fragmentation profile when compared to the adalimumab standard solution (FIG. 5C).

Figures 6A, 6B:
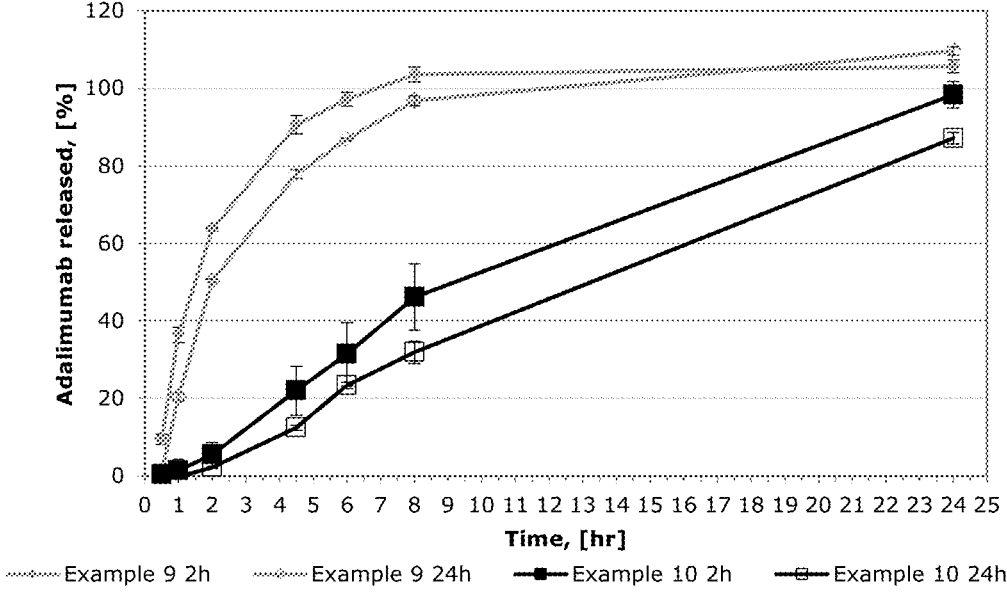
FIG. 6A presents a batch summary of ethylcellulose coated adalimumab pellets.
FIG. 6B shows DBS (hydrophobic plasticizer) coated pellets and TEC (25 wt.-%, based on polymer solids) coated pellets, both coated to about 17% polymer weight gain. The replacement of TEC (Example 9) as plasticizer by DBS (Example 10) lead to a much slower adalimumab release in citrate-TRIS buffer pH 7 for the same amount of polymer applied on the pellets.
Figure 6C:
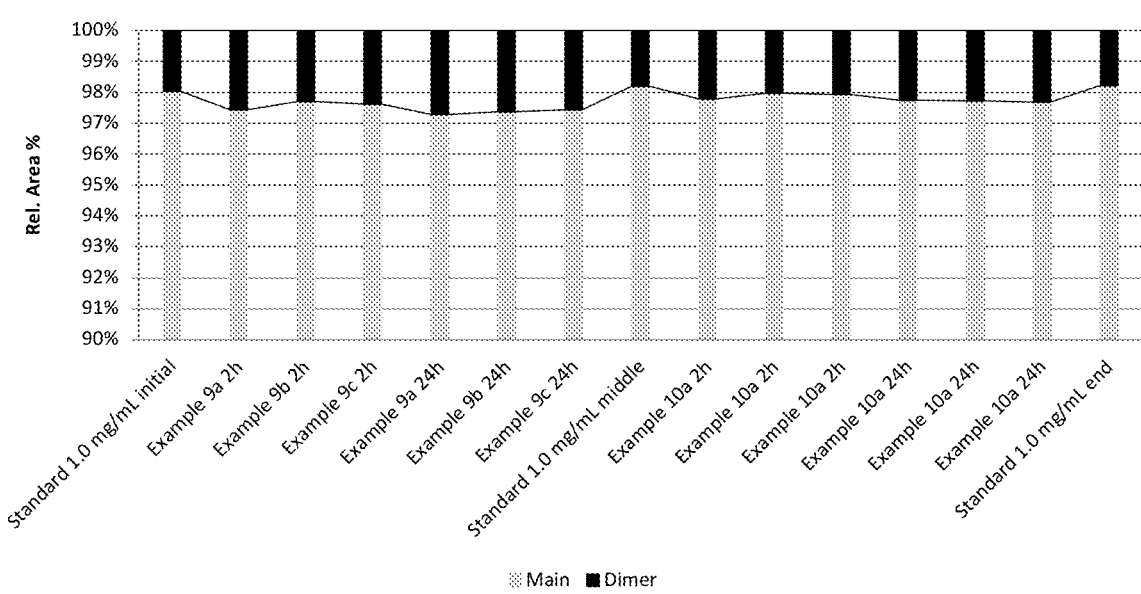
FIG. 6C shows the relative adalimumab aggregation and fragmentation profile of dissolution samples from Example 9 and Example 10 coated pellets. Independently of the plasticizer used, no significant increase in aggregates and fragments are seen in adalimumab from dissolution samples in comparison to the adalimumab standard.
Figure 6C:
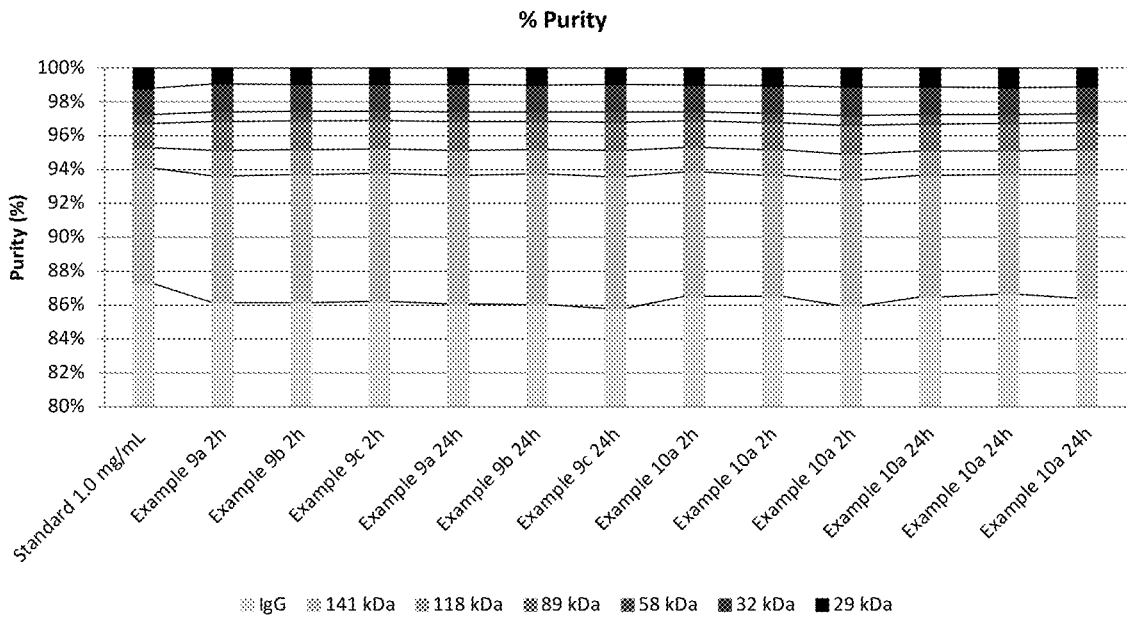

Dibutyl Sebacatec (DBS) and Triethyl Citrate (TEC) as Plasticizers in Ethylcellulose (Aquacoat ECD) Coated Pellets DBS (hydrophobic plasticizer) was used at the same concentration as TEC (25 wt.-%, based on polymer solids), both coated to about 17% polymer weight gain (FIG. 6A). The replacement of TEC (Example 9) as plasticizer by DBS (Example 10) had a significant impact on adalimumab release from the coated pellets, leading to a much slower adalimumab release for about the same amount of polymer applied on the pellets (FIG. 6B). This means that a target drug release profile (i.e. drug release for 24 h) can be achieved with the less sustained release polymer, making the coating process shorter and cheaper. For both TEC and DBS the curing time plays a role in the film formation, as pellets cured (dried) for 24 h showed a slightly slower drug release compared to pellets cured (dried) for 2 h. Independently of the plasticizer used, no significant increase in aggregates and fragments profiles are seen in adalimumab from dissolution samples in comparison to the adalimumab standard (FIG. 6C). This indicates that neither the formulation composition nor the process (including curing step at 60° C. for 24 hours) is detrimental to the stability of the antibody in these embodiments.

Figures 7A, 7B:
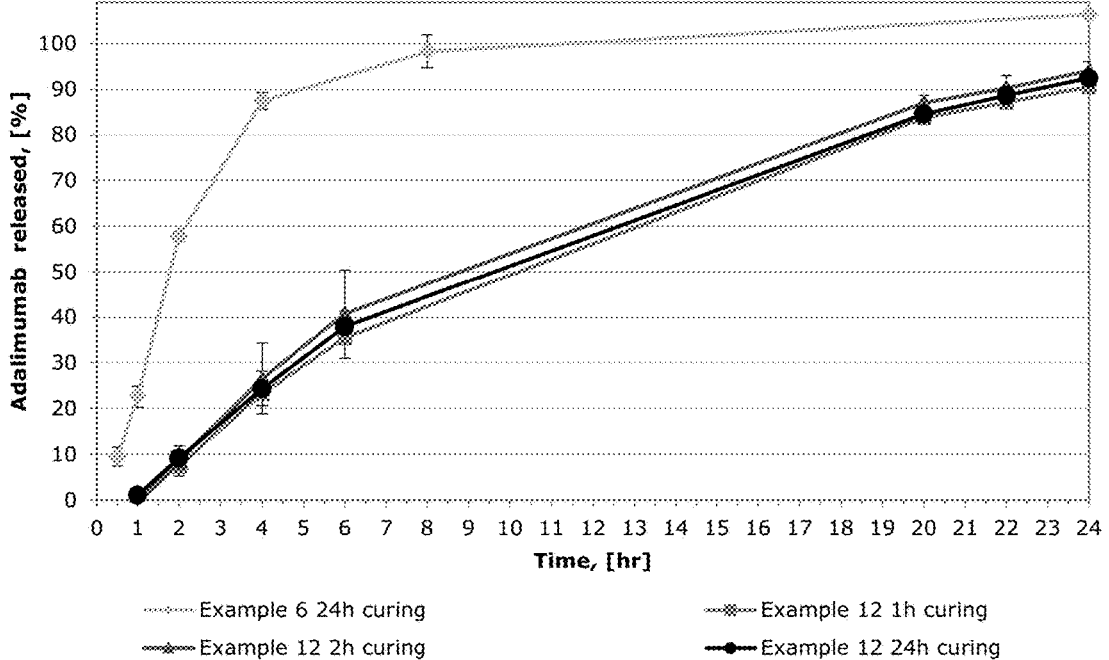
FIG. 7A presents a batch summary of Eudragit® RS 30D coated pellets with and without coalescence enhancer.
FIG. 7B shows that the addition of the coalescence enhancer Laurogylcol™ 90 (Example 12) is markedly improved the adalimumab sustained release profile compared to a coating without coalescence enhancer, even with a lower polymer weight gain (Example 6, FIG. 7B).

Experiment 5—Sustained Release Coating of Adalimumab Immediate Release Coated Pellets with Coalescence Enhancer Eudragit® RS 30D coating of adalimumab layered pellets was repeated and a coalescence enhancer Laurogylcol 90 was added (see FIG. 7A-B). As shown in FIG. 7B, addition of the coalescence enhancer Laurogylcol 90 (Example 12) markedly improved the sustained release profile compared (pellets cured for 1, 2 or 24 hours) to a coating without coalescence enhancer (Example 6, FIG. 7B) on pellets cured for 24 hours. Addition of Laurogylcol 90 to the Eudragit® RS 30D coating formulation thus improved film formation and markedly reduced the coating amount required to achieved target release profile.

Figure 8A:
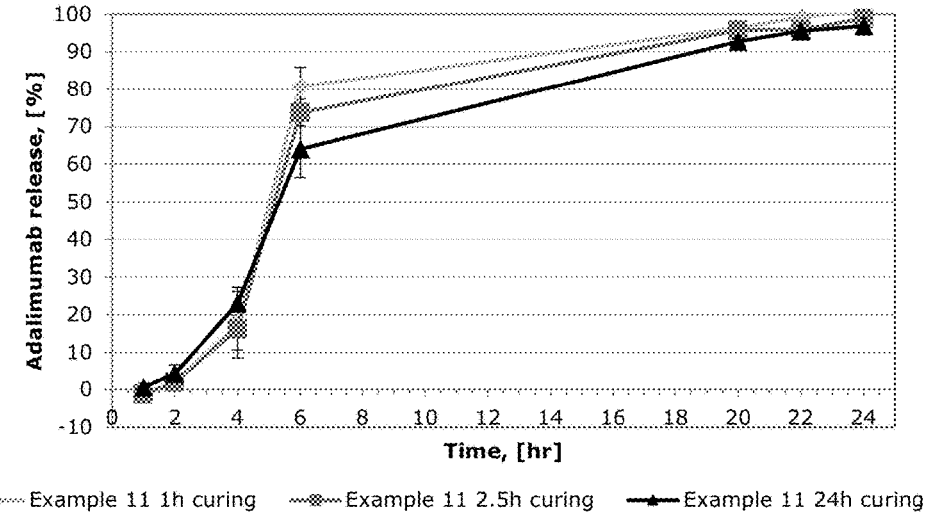
FIG. 8A graphically depicts adalimumab release from ethylcellulose coated pellets including Lauroglycol™ 90 dried/cured at 60° C. for 1, 2.5 h and 24 hours in citrate-TRIS buffer pH 7.
Figure 8B:
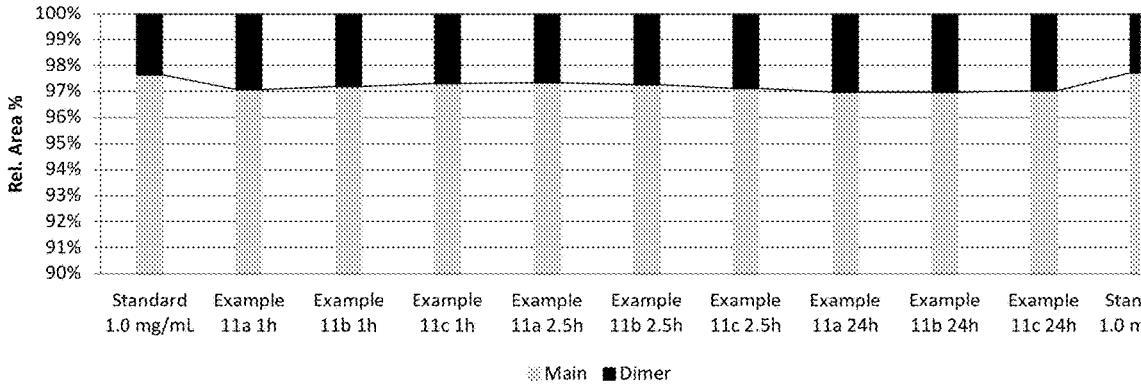
FIG. 8B depicts the relative adalimumab aggregation and fragmentation profile of dissolution samples from Example 11 coated pellets in comparison to the adalimumab standard. The addition of Lauroglycol™ to the formulation of ethylcellulose or the processing conditions, including a curing (drying) step up to 24 hours did not result in a significant increase in aggregates or fragments been formed in samples collected after dissolution (FIG. 8B).
Figure 8B:
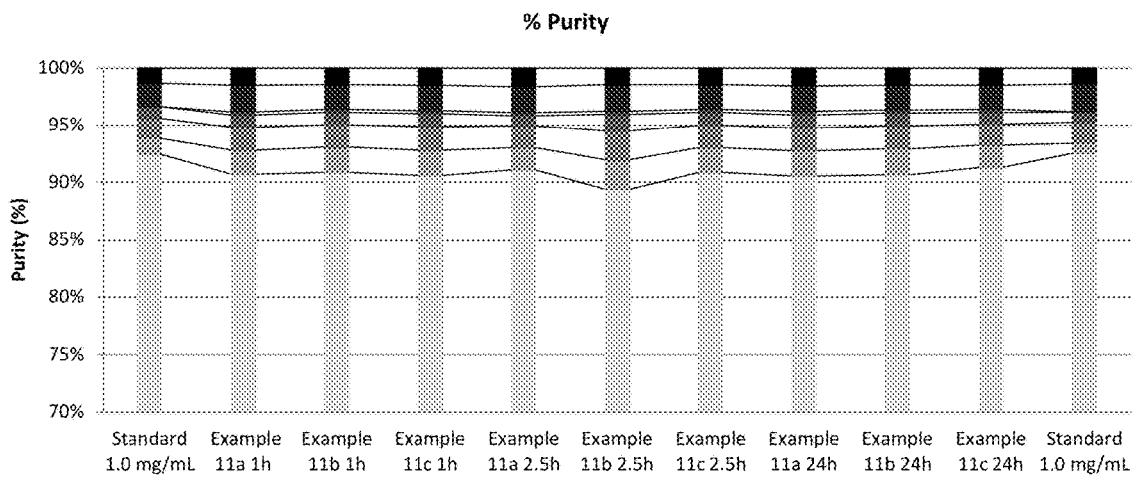

A similar effect was observed when using ethylcellulose aqueous dispersion (Aquacoat ECD) as sustained release polymer in combination with Laurogylcol 90 (FIG. 8A), compared to Aquacoat® ECD sustained release coating without Laurogylcol 90 (FIG. 6B). The addition of Laurogylcol 90 to the formulation (10% wt, based on polymer solids), clearly improved film formation demonstrated by the lack of significant different in the drug release profiles obtained for pellets cured for different periods of time (between 1 and 24 hours). Neither the addition of Laurogylcol™ 90 to the formulation of ethylcellulose, nor the processing conditions, including a curing (drying) step up to 24 hours at 60° C. in a drying cabinet resulted in a significant increase in aggregates or fragments been formed in samples collected after dissolution in citrate-TRIS buffer pH 7 (FIG. 8B).

ELISA Analysis Binding of Adalimumab to TNFα After Release From Pellets

Figure 9A:
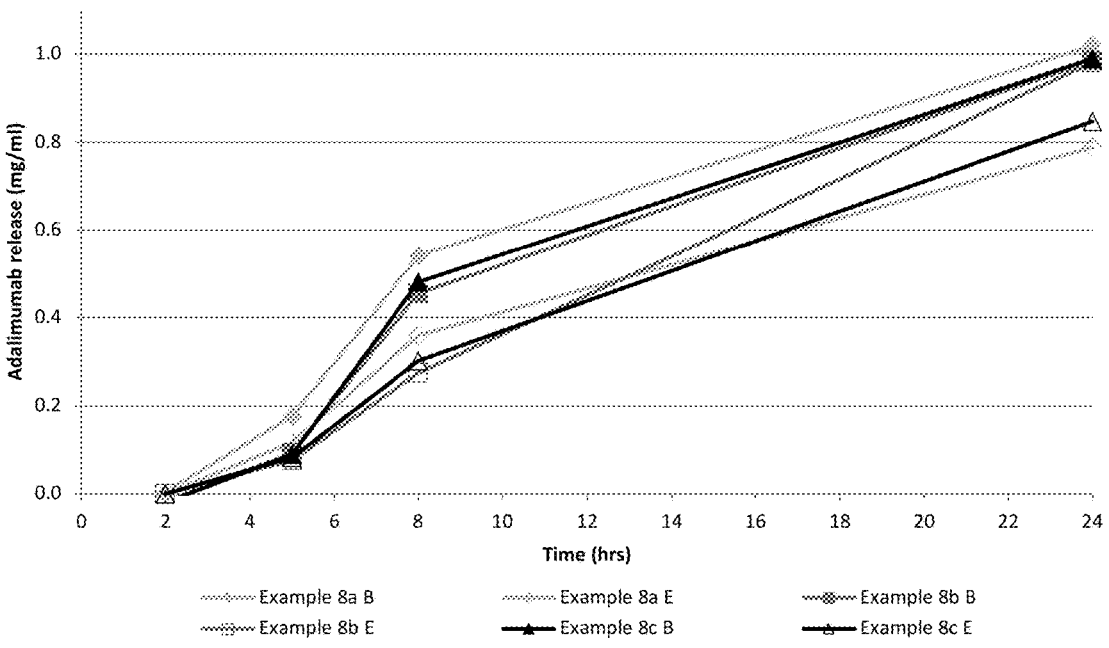
FIG. 9A presents an ELISA analysis from adalimumab recovered during dissolution of Example 8 (Eudragit® RS 30D coated pellets) in citrate-TRIS buffer pH 7.
Figure 9B:
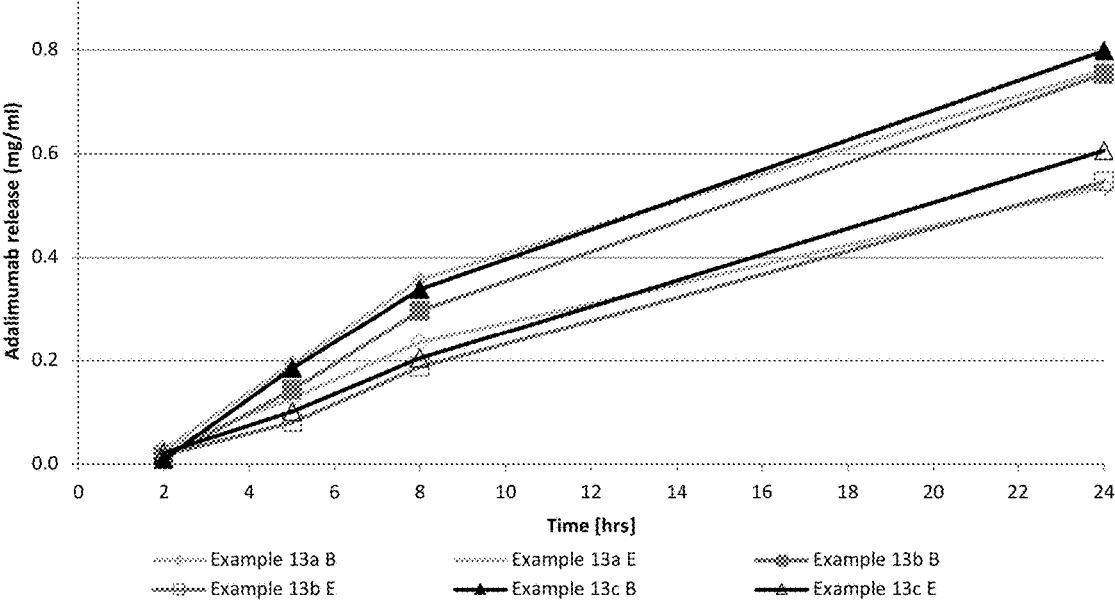
FIG. 9B presents ELISA analysis from adalimumab recovered during dissolution of Example 13 (21.67% polymer Aquacoat® ECD weight gain coated pellets) in citrate-TRIS buffer pH 7.

ELISA analysis was used to assess binding to TNFα of adalimumab released from coated pellets in citrate-TRIS buffer pH 7 (FIG. 9A-B). ELISA analysis from adalimumab recovered during dissolution of Example 8 (Eudragit® RS 30D coated pellets) in FIG. 9A and Example 13 (21.67% polymer Aquacoat® ECD weight gain coated pellets) in FIG. 9B showed that adalimumab integrity is kept and adalimumab is able to bind to TNFα. For comparison reasons the results of total protein quantification (B) and ELISA (E) are represented in FIG. 9A-B.

What is claimed:

1. A method for preparing a solid dosage form comprising i) an inert core unit; and ii) a drug coating, said drug coating comprising at least one antibody or functional fragment thereof as active agent, a buffer and at least one polymeric binder deposited on the inert core unit by drug layering; said method comprising the steps of:
    a) preparing an active agent coating liquid, comprising 1-50 mg/ml of the at least one antibody or functional fragment thereof, the buffer and the at least one polymeric binder, as an aqueous solution or suspension;
    b) layering the inert core unit with the active agent coating liquid of step (a) using spray coating; and
    c) drying the wet drug layered inert core unit, simultaneously with step b), or after step b) has been completed, to give rise to a dried solid dosage form.

2. The method according to claim 1, wherein the active agent coating liquid comprises:

i) 0.5-5 wt.-% antibody or functional fragment thereof;

ii) 1-20 wt.-% polymeric binder; and iii) 0-2 wt.-% anti-tacking agent.

3. The method according to claim 1, wherein the spray coating is a fluidized-bed spray coating during which the atomizing air pressure at a spray nozzle is lower than 200 kPa.

4. The method according to claim 1, wherein at any time during steps a) and c) the temperature of the at least one antibody or functional fragment thereof is lower than the melting temperature (Tm) of the at least one antibody or functional fragment thereof.

5. The method according to claim 1, wherein the polymeric binder in the drug coating is selected from the group consisting of hydroxypropyl methylcellulose (HPMC), methylcellulose (MC), hydroxypropyl cellulose (HPC), macrogol poly(vinylalcohol) grafted copolymer, polyvinylpyrrolidone (PVP) and combinations thereof.

6. The method according to claim 1, wherein the drug coating is suitable for immediate release of the active agent and wherein the wet drug layered inert core unit is dried simultaneously with step b) using the inlet air flow of a fluidized bed, and wherein the inlet air has a temperature of up to 60° C.

7. The method according to claim 1, wherein the polymeric binder in the drug coating comprises at least one sustained release polymeric binder, and wherein the wet drug layered inert core unit is dried after step b) has been completed, at a temperature of not higher than 65° C.

8. The method according to claim 7, wherein the at least one sustained release polymeric binder(S) and the at least one antibody or functional fragment thereof (A) are present in the active agent coating liquid in a ratio S/A (w/w) of 0.5 to 100.

9. The method according to claim 1, further comprising, after step c), the step of:

d) applying at least one additional coating in the form of a sustained release coating, by layering the solid dosage form of step c) with a sustained release coating liquid using spray coating, and then drying the wet layered solid dosage form using a fluidized bed or an oven.

10. The method according to claim 9, wherein the sustained release coating liquid comprises 5-20 wt.-% sustained release polymer, relative to the total weight of the sustained release coating liquid, and wherein the solid dosage form after step d) comprises a polymer weight gain of 2.5-25 wt.-% relative to the solid dosage form before step d).

11. The method according to claim 7, wherein the at least one sustained release polymeric binder is selected from the group consisting of poly(ethyl acrylate, methyl methacrylate) 2:1; poly(ethyl acrylate, methyl methacrylate, trimethylammonioethyl methacrylate chloride) 1:2:0.1; poly(ethyl acrylate, methyl methacrylate, trimethylammonioethyl methacrylate chloride) 1:2:0.2; ethylcellulose; polyvinyl acetate; and combinations thereof.

12. The method according to claim 1, wherein the active agent coating liquid further comprise(s) an anti-tacking agent, a surfactant, a filler, a plasticizer and/or a coalescence agent.

13. The method according to claim 12, wherein the active agent coating liquid comprise(s) 5-50 wt.-% anti-tacking agent, 10-30 wt.-% plasticizer, and/or 2-15 wt.-% coalescence enhancer, relative to the total weight of the polymeric binder solids in the active agent coating liquid and/or the polymer solids in the sustained release coating liquid, and/or 0.01-2 wt. % surfactant relative to the total weight of the active agent coating liquid and/or the sustained release coating liquid.

14. The method according to claim 1, wherein the at least one antibody or functional fragment thereof is selected from the group consisting of antibodies specific to tumor necrosis factor alpha (TNFα) and functional fragments thereof, antibodies specific to α4β7 integrin and functional fragments thereof, antibodies specific to CD3, CD4 or CD20 and functional fragments thereof, antibodies specific to interleukin 6 (IL-6), interleukin 12 (IL-12), interleukin 13 (IL-13), interleukin 23 (IL-23) or to their receptors and functional fragments thereof, antibodies specific to CXCL10/IP-10 and functional fragments thereof, and antibodies specific to p40 protein subunit and functional fragments thereof.

15. The method according to claim 1, further comprising, after step c), or after step d) if at least one additional coating in the form of a sustained release coating is applied as step d), the step of applying at least one additional coating in the form of a delayed release coating, and wherein the solid dosage form is for oral administration.

16. The method according to claim 15, wherein the delayed release coating comprises at least one component selected from the group consisting of poly vinyl acetate phthalate, cellulose acetate trimellitate, hydroxypropyl methylcellulose phthalate, cellulose acetate phthalate, hydroxypropyl methylcellulose acetate succinate (HPMCAS), poly(methacrylic acid, ethyl acrylate) 1:1, poly (methacrylic acid, methyl methacrylate) 1:1, poly(methacrylic acid, methyl methacrylate) 1:2, chondroitin sulfate, pectin, guar gum, chitosan, inulin, lactulose, raffinose, stachyose, alginate, dextran, xanthan gum, locust bean gum, arabinogalactan, amylose, cyclodextrin, pullulan, carrageenan, scleroglucan, chitin, curdulan, levan, amylopectin, starch, resistant starch, azo compounds being degraded by azo bonds splitting bacteria, and combinations thereof.

17. The method according to claim 15, wherein, upon oral administration of the solid dosage form, the release of the antibody or functional fragment thereof starts in the terminal ileum, the ileocolonic region, the ascending colon, transverse colon or the descending colon.

18. A solid dosage form prepared by the method of claim 1.

19. The solid dosage form according to claim 18 formulated for use in the treatment of a patient suffering from a gastrointestinal disease.

20. The method according to claim 3, wherein during the fluidized-bed spray coating the atomizing air pressure at the spray nozzle ranges from 10 to 100 kPa.

21. The method according to claim 7, wherein the wet drug layered inert core unit is dried at a temperature of not higher than 60° C.

22. The method according to claim 1, wherein the active agent coating liquid comprises 1-5 wt.-% buffer.

23. The method according to claim 22, wherein the buffer is operable at physiological pH and is selected from the group consisting of acetate buffer, citrate buffer, histidine buffer, succinate buffer, phosphate buffer, hydroxymethylaminomethane (TRIS) buffer, and combinations thereof.

24. The method according to claim 22, wherein the buffer is a citrate-TRIS buffer operable at pH 7.

\* \* \* \* \*